(12) United States Patent
Mazitschek et al.

(10) Patent No.: US 9,988,343 B2
(45) Date of Patent: Jun. 5, 2018

(54) INHIBITORS OF HISTONE DEACETYLASE

(71) Applicants: Dana-Farber Cancer Institute, Inc., Boston, MA (US); The General Hospital Corporation, Boston, MA (US)

(72) Inventors: Ralph Mazitschek, Belmont, MA (US); Teru Hideshima, Brookline, MA (US); Kenneth C. Anderson, Wellesley, MA (US); Stephen J. Haggarty, Gloucester, MA (US); Balaram Ghosh, Hyderabad (IN)

(73) Assignees: Dana-Farber Cancer Institute, Inc., Boston, MA (US); The General Hospital Corporation, Boston, MA (US)

( * ) Notice: Subject to any disclaimer, the term of this patent is extended or adjusted under 35 U.S.C. 154(b) by 0 days. days.

(21) Appl. No.: 15/034,276

(22) PCT Filed: Nov. 5, 2014

(86) PCT No.: PCT/US2014/064016
§ 371 (c)(1),
(2) Date: May 4, 2016

(87) PCT Pub. No.: WO2015/069693
PCT Pub. Date: May 14, 2015

(65) Prior Publication Data
US 2016/0272579 A1    Sep. 22, 2016

Related U.S. Application Data

(60) Provisional application No. 61/900,033, filed on Nov. 5, 2013.

(51) Int. Cl.
| | |
|---|---|
| *A61K 31/4406* | (2006.01) |
| *A61K 31/167* | (2006.01) |
| *A61K 31/69* | (2006.01) |
| *C07C 237/40* | (2006.01) |
| *C07D 213/82* | (2006.01) |
| *C07D 241/24* | (2006.01) |
| *A61K 38/05* | (2006.01) |
| *A61K 45/06* | (2006.01) |
| *A61K 31/4402* | (2006.01) |
| *A61K 31/4409* | (2006.01) |
| *A61K 31/455* | (2006.01) |
| *A61K 31/4965* | (2006.01) |
| *A61K 31/505* | (2006.01) |
| *C07D 213/81* | (2006.01) |
| *C07D 239/42* | (2006.01) |
| *C07C 237/42* | (2006.01) |

(52) U.S. Cl.
CPC ......... *C07C 237/40* (2013.01); *A61K 31/167* (2013.01); *A61K 31/4402* (2013.01); *A61K 31/4406* (2013.01); *A61K 31/4409* (2013.01); *A61K 31/455* (2013.01); *A61K 31/4965* (2013.01); *A61K 31/505* (2013.01); *A61K 31/69* (2013.01); *A61K 38/05* (2013.01); *A61K 45/06* (2013.01); *C07C 237/42* (2013.01); *C07D 213/81* (2013.01); *C07D 213/82* (2013.01); *C07D 239/42* (2013.01); *C07D 241/24* (2013.01)

(58) Field of Classification Search
CPC .. A61K 31/4406; A61K 31/167; A61K 31/69; C07C 237/40; C07D 213/82; C07D 241/24
See application file for complete search history.

(56) References Cited

U.S. PATENT DOCUMENTS

2008/0039509 A1   2/2008   Lu et al.
2009/0247549 A1   10/2009  Frankel et al.

FOREIGN PATENT DOCUMENTS

WO   WO-2009/137503 A1   11/2009
WO   WO-2013/005049 A1   1/2013

OTHER PUBLICATIONS

Patanini et al.. Chemical Reviews (Patani et al. 1996), 3147-3176).*
Minami et al Leukemia 2014) 28, 680-689, first published on line on Sep. 6, 2013.*
Hamblett et al., "The discovery of 6-amino nicotinamides as potent and selective histone deacetylase inhibitors," Bioorg Med Chem Lett, 17:5300-9 (2007).
International Search Report issued by the International Searching Authority, dated Jan. 14, 2015, in corresponding International Application No. PCT/US2014/064016.
Written Opinion issued by the International Searching Authority, dated Jan. 14, 2015, in corresponding International Application No. PCT/US2014/064016.
Alas et al., "Inhibition of constitutive STAT3 activity sensitizes resistant non-Hodgkin's lymphoma and multiple myeloma to chemotherapeutic drug-mediated apoptosis," Clin Cancer Res, 9(1): 316-326 (2003).
Bhutani et al., "Capsaicin is a novel blocker of constitutive and interleukin-6-inducible STAT3 activation," Clin Cancer Res, 13(10): 3024-3032 (2007).
Bradner et al., Chemical phylogenetics of histone deacetylases. Nat Chem Biol, 6(3): 238-243 (2010).

(Continued)

*Primary Examiner* — Shirley V Gembeh
(74) *Attorney, Agent, or Firm* — Foley Hoag LLP

(57) ABSTRACT

The present invention relates to compounds which inhibit histone deacetylase activity and methods of synthesizing these compounds. The present invention also relates to pharmaceutical compositions containing these compounds. The present invention also relates to methods of treating and preventing hematological cell proliferative disorders, such as multiple myeloma, by administering these compounds and pharmaceutical compositions to subjects in need thereof.

22 Claims, 22 Drawing Sheets

(56) References Cited

OTHER PUBLICATIONS

Burger et al., "Janus kinase inhibitor INCB20 has antiproliferative and apoptotic effects on human myeloma cells in vitro and in vivo," Mol Cancer Ther 8(1): 26-35 (2009).
Catley et al., "Aggresome induction by proteasome inhibitor bortezomib and alpha-tubulin hyperacetylation by tubulin deacetylase (TDAC) inhibitor LBH589 are synergistic in myeloma cells," Blood, 108(10): 3441-3449 (2006).
Catley et al., "NVP-LAQ824 is a potent novel histone deacetylase inhibitor with significant activity against multiple myeloma," Blood, 102(7): 2615-2622 (2003).
Cirstea et al., Small molecule Multi-Targeted kinase inhibitor RGB-286638 Triggers P53-Dependent and -Independent Anti-Multiple myeloma activity through inhibition of transcriptional CDKs, Leukemia (2013).
Deangelo et al., "Phase Ia/II, two-arm, open-label, dose-escalation study of oral panobinostat administered via two dosing schedules in patients with advanced hematologic malignancies," Leukemia, 27(8): 1628-1636 (2013).
Dimopoulos et al., "Vantage 088: Vorinostat in combination with bortezomib in patients with relapsed refractory multiple myeloma: results of a global randomized phase 3 trial," Blood, 118: 368-369 (2011).
Gupta et al., "Regulation of STAT3 by histone deacetylase-3 in diffuse large B-cell lymphoma: implications for therapy," Leukemia, 26(6): 1356-1364 (2012).
Hideshima et al., "A proto-oncogene BCL6 is up-regulated in the bone marrow microenvironment in multiple myeloma cells," Blood, 115(18): 3772-3775 (2010).
Hideshima et al., "Induction of differential apoptotic pathways in multiple; myeloma cells by class-selective histone deacetylase inhibitors," Leukemia, 28(2): 457-460 (2014).
Hideshima et al., "Molecular mechanisms of novel therapeutic approaches for multiple myeloma," Nat Rev Cancer, 2(12): 927-937 (2002).
Hideshima et al., "Perifosine, an oral bioactive novel alkylphospholipid, inhibits Akt and induces in vitro and in vivo cytotoxicity in human multiple myeloma cells.," Blood, 107(10): 4053-4062 (2006).
Hideshima et al., "Proteasome inhibitor PS-341 abrogates IL-6 triggered signaling cascades via caspase-dependent downregulation of gp130 in multiple myeloma," Oncogene, 22(52): 8386-8393 (2003).
Hideshima et al., "Small-molecule inhibition of proteasome and aggresome function induces synergistic antitumor activity in multiple myeloma," Proc Natl Acad Sci U S A, 102(24): 8567-8572 (2005).
Hideshima et al., "Understanding multiple myeloma pathogenesis in the bone marrow to identify new therapeutic targets," Nat Rev Cancer, 7(8): 585-598 (2007).
Lane et al., "Histone deacetylase inhibitors in cancer therapy," J Clin Oncol, 27(32): 5459-5468 (2009).
Lee et al., "Acetylation and activation of STAT3 mediated by nuclear translocation of CD44," J Cell Biol, 185(6): 949-957 (2009).
Li et al., "Bortezomib up-regulates activated signal transducer and activator of transcription-3 and synergizes with inhibitors of signal transducer and activator of transcription-3 to promote head and neck squamous cell carcinoma cell death," Mol Cancer Ther, 8(8): 2211-2220 (2009).
Malvaez et al., "HDAC3-selective inhibitor enhances extinction of; cocaine-seeking behavior in a persistent manner," PNAS 110(7): 2647-2652 (2013).
McQuown et al., "HDAC3 and the molecular brake pad hypothesis," Neurobiol Learn Mem, 96(1): 27-34 (2011).
McQuown et al., "HDAC3 is a critical negative regulator of long-term memory; formation," J Neurosci, 31(2): 764-774 (2011).
Mitsiades et al., "Molecular sequelae of histone deacetylase inhibition in human malignant B cells," Blood, 101(10): 4055-4062 (2003).
Nelson et al., "Nifuroxazide inhibits survival of multiple myeloma cells by directly inhibiting STAT3," Blood,112(13): 5095-5102 (2008).
Quintas-Cardama et al., "Histone deacetylase inhibitors for the treatment of myelodysplastic syndrome and acute myeloid leukemia," Leukemia, 25(2): 226-235 (2011).
Raje et al., "New drug partner for combination therapy in multiple myeloma (MM): development of ACY-1215, a selective histone deacetylase 6 inhibitor alone and in combination with bortezomib or lenalidomide," Haematologica, 98(S1): 320 (2013).
Raje et al., "Seliciclib (CYC202 or R-roscovitine), a small-molecule cyclin-dependent kinase inhibitor, mediates activity via downregulation of Mcl-1 in multiple myeloma," Blood, 106(3): 1042-1047 (2005).
Rogge et al., "HDAC3 is a negative regulator of cocaine-context associated; memory formation," J Neurosci, 33(15): 6623-6632 (2013).
Santo et al., "Anti-myeloma activity of a multitargeted kinase inhibitor, AT9283, via potent Aurora kinase and STAT3 inhibition either alone or in combination with lenalidomide," Clin Cancer Res, 17(10): 3259-3271 (2011).
Santo et al., "Preclinical activity, pharmacodynamic, and pharmacokinetic properties of a selective HDAC6 inhibitor, ACY-1215, in combination with bortezomib in multiple myeloma," Blood, 119(11): 2579-2589 (2012).
Schrump, "Cytotoxicity mediated by histone deacetylase inhibitors in cancer cells: mechanisms and potential clinical implications," Clin Cancer Res, 15(12): 3947-3957 (2009).
Singh et al., "Nonhistone protein acetylation as cancer therapy targets," Expert Rev Anticancer Ther, 10(6): 935-954 (2010).
Stubbs et al., "Selective inhibition of HDAC1 and HDAC2 Is a potential therapeutic option for B-ALL," Blood, 116: 1194-1194 (2010).
Tai et al., "CRM1 inhibition induces tumor cell cytotoxicity and impairs osteoclastogenesis in multiple myeloma: molecular mechanisms and therapeutic implications," Leukemia, 28(1): 155-165 (2014).
Togi et al., "HDAC3 influences phosphorylation of STAT3 at serine 727 by interacting with PP2A," Biochem Biophys Res Commun, 379(2): 616-620 (2009).
Yuan et al., "Stat3 dimerization regulated by reversible acetylation of a single lysine residue," Science, 307(5707): 269-273 (2005).
Zhang et al., "The proteasome inhibitor bortezomib interacts synergistically with the histone deacetylase inhibitor suberoylanilide hydroxamic acid to induce T-leukemia/lymphoma cells apoptosis," Leukemia, 23(8): 1507-1514 (2009).

* cited by examiner

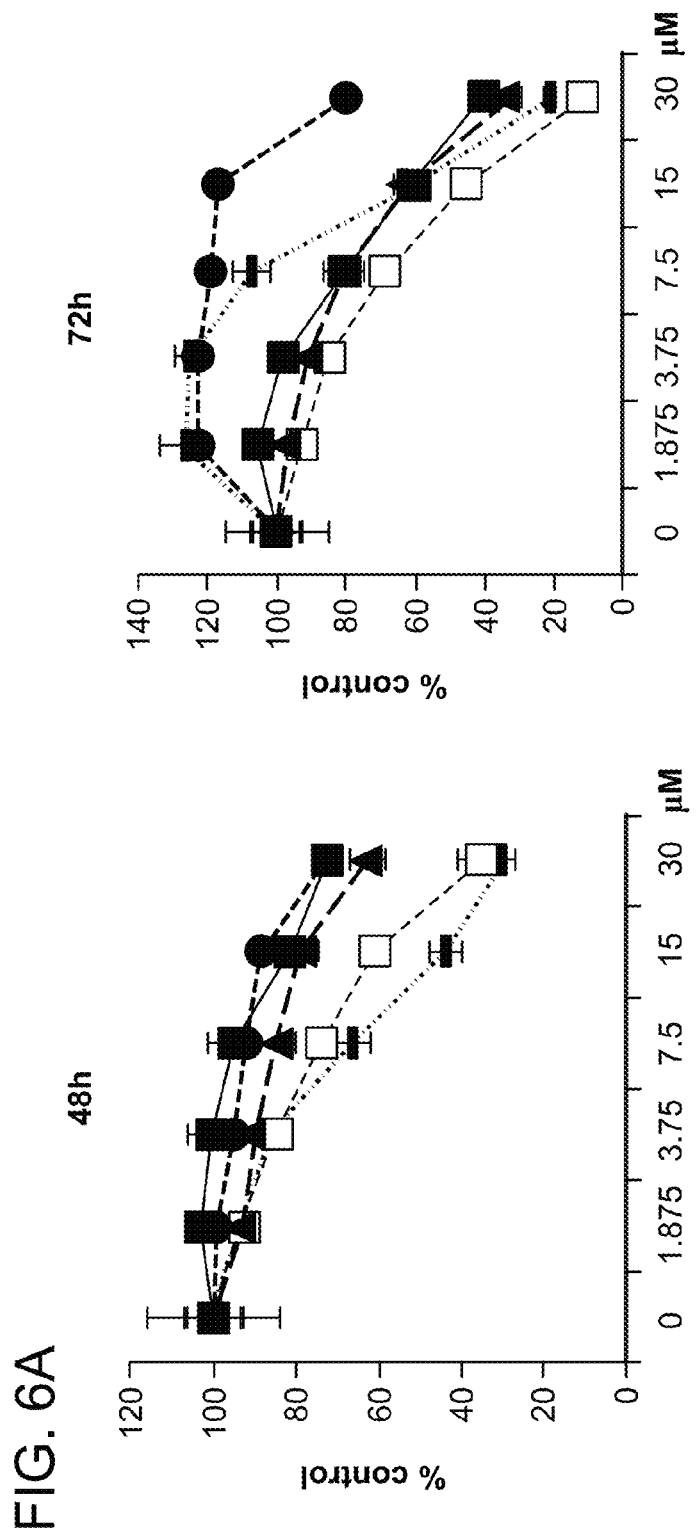

INHIBITORS OF HISTONE DEACETYLASE

RELATED APPLICATIONS

This application is the U.S. national phase of International Patent Application No. PCT/US2014/064016, filed Nov. 5, 2014, which claims the benefit of priority to U.S. Provisional Patent Application Ser. No. 61/900,033, filed Nov. 5, 2013, which are hereby incorporated by reference.

GOVERNMENT SUPPORT

This invention was made with government support under Grant Nos. SPORE-P50100707, P01 CA78378, R01 CA50947, R01 DA02830, and P50CA086355, awarded by the National Institutes of Health. The U.S. government has certain rights in the invention. This statement is included solely to comply with 37 C.F.R. § 401.14(a)(f)(4) and should not be taken as an assertion or admission that the application discloses and/or claims only one invention.

BACKGROUND OF THE INVENTION

Multiple myeloma (MM) is the second most common hematological malignancy. MM remains incurable despite that various therapeutic agents, including proteasome inhibitors (e.g., bortezomib) and immunomodulatory drugs (e.g., thalidomide and lenalidomide), are available. A major challenge for molecular targeted therapy in MM is its genetic complexity and molecular heterogeneity. Gene transcription within the tumor cell and its microenvironment can also be altered by epigenetic modulation (e.g., acetylation and methylation). Thus, inhibition of histone deacetylases (HDACs) has emerged as a novel targeted treatment strategy in MM.

Historic deacetylases are divided into 4 classes: class-I (HDAC1, 2, 3, 8), class-IIa (HDAC4, 5, 7, 9), class-IIb (HDAC6,10), class-III (SIRT1-7), and class-IV (HDAC11). These classes differ in their subcellular localization (class-1 DACs are present in nucleus and class-II enzymes are cytoplasmic) and their intracellular targets. Although HDAC is based on histone target proteins, recent studies reveal at least 3,600 acetylation sites on 1,750 non histone proteins in cancer cells associated with various functions including gene expression, DNA replication and repair, cell cycle progression, cytoskeletal reorganization, and protein chaperone activity. Clinical trials with non-selective HDAC inhibitors (HDACi) have shown efficacy, but are limited due to side effects, such as fatigue, diarrhea, and thrombocytopenia.

Thus, there is currently a need to develop HDAC inhibitors to treat hematological cell proliferative disorders, such as MM, that have minimal adverse side effects. The present invention addresses the need.

SUMMARY OF THE INVENTION

The present invention provides, in part, compounds of formula I and methods of preparing the compounds of formula I:

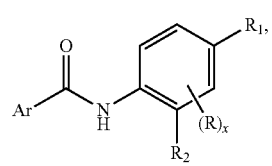

(I)

wherein:
Ar is unsubstituted or substituted phenyl, unsubstituted or substituted pyrazinyl, unsubstituted or substituted pyrimidinyl, unsubstituted or substituted pyridinyl, unsubstituted or substituted quinolinyl, unsubstituted or substituted isoquinolinyl, unsubstituted or substituted quinazolinyl, or unsubstituted or substituted quinoxalinyl;

$R_1$ and $R_2$ are each independently H, hydroxyl, cyano, halogen, unsubstituted or substituted amino, unsubstituted or substituted $C_1$-$C_6$ alkyl, or unsubstituted or substituted $C_1$-$C_6$ alkoxy;

each R is independently hydroxyl, cyano, halogen, unsubstituted or substituted amino, unsubstituted or substituted $C_1$-$C_6$ alkyl, unsubstituted or substituted $C_1$-$C_6$ alkoxy, or unsubstituted or substituted $C_6$-$C_{10}$ aryl; and x is 0, 1, 2, or 3;

provided that when Ar is unsubstituted pyrazinyl, x is not 0, or a pharmaceutically acceptable salt, ester, solvate, or prodrug thereof.

The present invention also provides pharmaceutical compositions comprising one or more compounds of each of the formulae described herein and one or more pharmaceutically acceptable carriers.

The present invention also provides methods of treating a hematological cell proliferative disorder by administering to a subject in need thereof, a therapeutically effective amount of a compound of each of the formulae described herein, or a pharmaceutically acceptable salt, ester, solvate, or prodrug thereof, in combination with a pharmaceutically acceptable carrier, such that the disorder is treated.

The present invention also provides methods of treating a multiple myeloma by administering to a subject in need thereof, a therapeutically effective amount of a compound of each of the formulae described herein, or a pharmaceutically acceptable salt, ester, solvate, or prodrug thereof, in combination with a pharmaceutically acceptable carrier, such that the multiple myeloma is treated.

The present invention also provides methods of selectively inducing cell death in precancerous or cancerous cells by contacting the cells with an effective amount of a compound of each of the formulae described herein, or a pharmaceutically acceptable salt, ester, solvate, or prodrug thereof, in combination with a pharmaceutically acceptable carrier, such that contacting the cell results in selective induction of cell death in the precancerous or cancer cells.

Unless otherwise defined, all technical and scientific terms used herein have the same meaning as commonly understood by one of ordinary skill in the art to which this invention belongs. In this case of conflict, the present specification, including definitions, will control. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the claimed invention. In addition, the materials, methods, and examples are illustrative only and are not intended to be limiting.

Other features and advantages of the invention will be apparent from the following detailed description and claims.

BRIEF DESCRIPTION OF THE DRAWINGS

FIG. 6A is a set of graphs showing growth of MM cell lines by the MTT assay in various concentrations of Compound 10 (MM.1S (□), RPMI8226 (●), U266 (▲), OPM1 (−), and H929 (■)).

DETAILED DESCRIPTION OF THE INVENTION

1. Compounds of the Invention

Figure 1A:
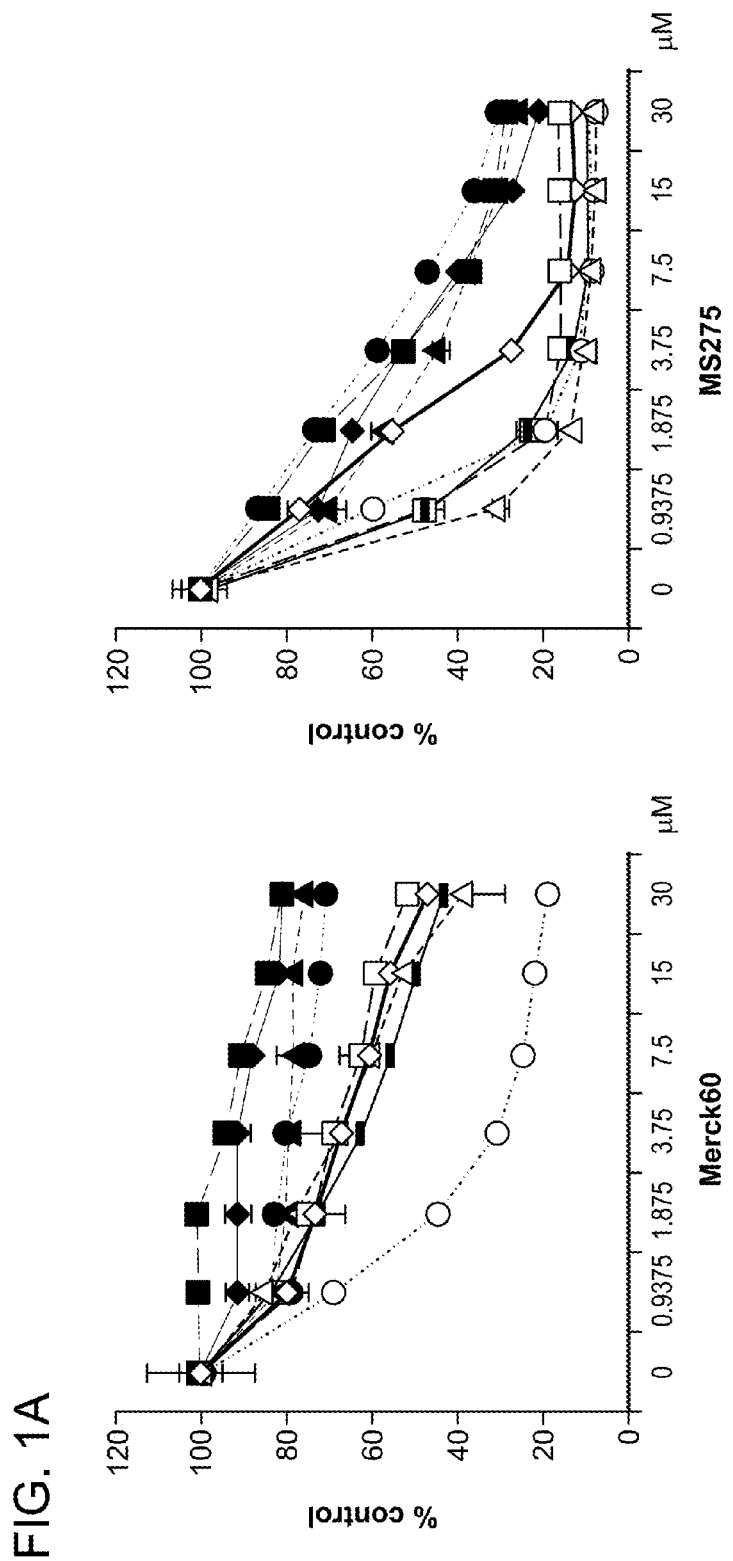
FIG. 1A is a graph of viability of MM cell lines treated with Merck60 or MS275 by the MTT assay (MM.1S (□), RPMI8226 (●), U266 (▲), H929 (■), MM.1R (Δ), RPMI-LR5 (♦), OPM1 (−), OPM2 (○), and RPMI-DOX40 (◇)).

The present invention provides novel compounds, synthetic methods for making the compounds, pharmaceutical compositions containing them and various uses of the disclosed compounds.

The present invention provides the compounds of formulae I:

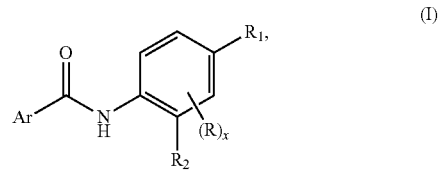

(I)

wherein:
Ar is unsubstituted or substituted phenyl, unsubstituted or substituted pyrazinyl, unsubstituted or substituted pyrimidinyl, unsubstituted or substituted pyridinyl, unsubstituted or substituted quinolinyl, unsubstituted or substituted isoquinolinyl, unsubstituted or substituted quinazolinyl, or unsubstituted or substituted quinoxalinyl;

$R_1$ and $R_2$ are each independently H, hydroxyl, cyano, halogen, unsubstituted or substituted amino, unsubstituted or substituted $C_1$-$C_6$ alkyl, or unsubstituted or substituted $C_1$-$C_6$ alkoxy;

each R is independently hydroxyl, cyano, halogen, unsubstituted or substituted amino, unsubstituted or substituted $C_1$-$C_6$ alkyl, unsubstituted or substituted $C_1$-$C_6$ alkoxy, or unsubstituted or substituted $C_6$-$C_{10}$ aryl; and x is 0, 1, 2, or 3;

provided that when Ar is unsubstituted pyrazinyl, x is not 0, or a pharmaceutically acceptable salt, ester, solvate, or prodrug thereof.

In one embodiment, only one of $R_1$ and $R_2$ is H.

In one embodiment, $R_1$ and/or $R_2$ are hydroxyl.

In one embodiment, $R_1$ and/or $R_2$ are cyano.

In one embodiment, $R_1$ and/or $R_2$ are each independently halogen (e.g., fluorine, chlorine, bromine, and iodine).

In one embodiment, $R_1$ and/or $R_2$ are each independently unsubstituted amino or amino mono- or di-substituted with $C_1$-$C_6$ alkyl (e.g., methyl, ethyl, propyl, and butyl).

In one embodiment, $R_1$ and/or $R_2$ are unsubstituted amino.

In one embodiment, $R_1$ and/or $R_2$ are each independently unsubstituted or substituted $C_1$-$C_6$ alkyl, e.g., straight chain $C_1$-$C_6$ alkyl or branched $C_3$-$C_6$ alkyl, including but not limited to, methyl, ethyl, n-propyl, i-propyl, n-butyl, i-butyl, s-butyl, t-butyl, n-pentyl, s-pentyl, and n-hexyl, each of which is optionally substituted with one or more groups independently selected from a) hydroxyl, halogen (e.g., fluorine, chlorine, bromine and iodine), b) unsubstituted or substituted $C_1$-$C_6$ alkoxy (e.g., methoxy, ethoxy, propyloxy, i-propyloxy, butoxy, and t-butoxy), c) unsubstituted or substituted amino (e.g., amino, unsubstituted or substituted $C_1$-$C_6$ alkylamino (e.g., methylamino, ethylamino, propylamino, and i-propylamino), and unsubstituted or substituted di-$C_1$-$C_6$ alkylamino (e.g., dimethylamino, diethylamino, dipropylamino, and di-i-propylamino)), d) unsubstituted or substituted $C_6$-$C_{10}$ aryl (e.g., phenyl and naphthyl), unsubstituted or substituted heteroaryl comprising one or two 5- or 6-member rings and 1-4 heteroatoms selected from N, O and S, unsubstituted or substituted $C_3$-$C_{10}$ carbocycle, and unsubstituted or substituted heterocycle comprising one or two 5- or 6-member rings and 1-4 heteroatoms selected from N, O and S.

In one embodiment, $R_1$ and/or $R_2$ are each independently unsubstituted methyl, ethyl, trifluoromethyl, or trichloromethyl.

In one embodiment, $R_1$ and/or $R_2$ are each independently unsubstituted or substituted $C_1$-$C_6$ alkoxy (e.g., methoxy, ethoxy, propyloxy, i-propyloxy, butoxy, and t-butoxy).

In one embodiment, $R_1$ and/or $R_2$ are each independently methoxy, ethoxy, trifluoromethoxy, or trichloromethoxy.

In one embodiment, $R_1$ is H and $R_2$ is H, hydroxyl, cyano, halogen, unsubstituted or substituted amino, unsubstituted or substituted $C_1$-$C_6$ alkyl, or unsubstituted or substituted $C_1$-$C_6$ alkoxy.

In one embodiment, $R_1$ is H and $R_2$ is hydroxyl, cyano, halogen, unsubstituted or substituted amino, unsubstituted or substituted $C_1$-$C_6$ alkyl, or unsubstituted or substituted $C_1$-$C_6$ alkoxy.

In one embodiment, $R_1$ is H and $R_2$ is hydroxyl.

In one embodiment, $R_1$ is H and $R_2$ is amino.

In one embodiment, $R_1$ is H and $R_2$ is amino mono- or di-substituted with $C_1$-$C_6$ alkyl (e.g., methyl, ethyl, propyl, and butyl).

In one embodiment, $R_2$ is H and $R_1$ is H, hydroxyl, cyano, halogen, unsubstituted or substituted amino, unsubstituted or substituted $C_1$-$C_6$ alkyl, or unsubstituted or substituted $C_1$-$C_6$ alkoxy.

In one embodiment, $R_2$ is H and $R_1$ is H, hydroxyl, cyano, halogen, unsubstituted or substituted amino, unsubstituted or substituted $C_1$-$C_6$ alkyl, or unsubstituted or substituted $C_1$-$C_6$ alkoxy.

In one embodiment, $R_2$ is H and $R_1$ is halogen.

In one embodiment, $R_2$ is H and $R_1$ is fluorine.

In one embodiment, $R_1$ is halogen and $R_2$ is hydroxyl, cyano, halogen, unsubstituted or substituted amino, unsubstituted or substituted $C_1$-$C_6$ alkyl, or unsubstituted or substituted alkoxy.

In one embodiment, $R_1$ is fluorine and $R_2$ is hydroxyl or unsubstituted or substituted amino.

In one embodiment, $R_1$ is fluorine and $R_2$ is unsubstituted amino.

In one embodiment, x is 0.

In one embodiment, x is 1.

In one embodiment, x is 2.

In one embodiment, at least one R is hydroxyl.

In one embodiment, at least one R is cyano.

In one embodiment, each R is independently fluorine, chlorine, bromine, or iodine.

In one embodiment, at least one R is fluorine, chlorine, bromine, or iodine.

In one embodiment, at least one R is fluorine.

In one embodiment, each R is independently unsubstituted amino or amino mono- or di-substituted with $C_1$-$C_6$ alkyl (e.g., methyl, ethyl, propyl, and butyl).

In one embodiment, at least one R is unsubstituted amino.

In one embodiment, each R is independently unsubstituted or substituted $C_1$-$C_6$ alkyl, e.g., straight chain $C_1$-$C_6$ alkyl or branched $C_3$-$C_6$ alkyl, including but not limited to, methyl, ethyl, n-propyl, i-propyl, n-butyl, i-butyl, s-butyl, t-butyl, n-pentyl, s-pentyl, and n-hexyl, each of which is optionally substituted with one or more groups independently selected from:

a) hydroxyl, halogen (e.g., fluorine, chlorine, bromine and iodine), b) unsubstituted or substituted $C_1$-$C_6$ alkoxy (e.g., methoxy, ethoxy, propyloxy, i-propyloxy, butoxy, and t-butoxy), c) unsubstituted or substituted amino (e.g., amino, unsubstituted or substituted $C_1$-$C_6$ alkylamino (e.g., methylamino, ethylamino, propylamino, and i-propylamino), and unsubstituted or substituted di-$C_1$-$C_6$ alkylamino (e.g., dimethylamino, diethylamino, dipropylamino, and di-i-propylamino)), d) unsubstituted or substituted $C_6$-$C_{10}$ aryl (e.g., phenyl and naphthyl), unsubstituted or substituted heteroaryl comprising one or two 5- or 6-member rings and 1-4 heteroatoms selected from N, O and S, unsubstituted or substituted $C_3$-$C_{10}$ carbocycle, and unsubstituted or substituted heterocycle comprising one or two 5- or 6-member rings and 1-4 heteroatoms selected from N, O and S.

In one embodiment, each R is independently unsubstituted methyl, ethyl, trifluoromethyl, or trichloromethyl.

In one embodiment, at least one R is unsubstituted methyl, ethyl, trifluoromethyl, or trichloromethyl.

In one embodiment, each R is independently unsubstituted or substituted $C_1$-$C_6$ alkoxy (e.g., methoxy, ethoxy, propyloxy, i-propyloxy, butoxy, and t-butoxy).

In one embodiment, each R is independently methoxy, ethoxy, trifluoromethoxy, or trichloromethoxy.

In one embodiment, at least one R is methoxy, ethoxy, trifluoromethoxy, or trichloromethoxy.

In one embodiment, each R is independently unsubstituted phenyl or naphthyl.

In one embodiment, at least one R is unsubstituted phenyl.

In one embodiment, each R is independently phenyl substituted with one or more groups independently selected from:
  a) hydroxyl, cyano, halogen (e.g., fluorine, chlorine, bromine, or iodine),
  b) unsubstituted or substituted $C_1$-$C_6$ alkyl (e.g., methyl, ethyl, n-propyl, i-propyl, n-butyl, i-butyl, s-butyl, t-butyl, n-pentyl, s-pentyl, and n-hexyl), and
  c) unsubstituted or substituted amino (e.g., amino, unsubstituted or substituted $C_1$-$C_6$ alkylamino (e.g., methylamino, ethylamino, propylamino, and i-propylamino), and unsubstituted or substituted di-$C_1$-$C_6$ alkylamino (e.g., dimethylamino, diethylamino, dipropylamino, and di-i-propylamino)).

In one embodiment, Ar is unsubstituted or substituted phenyl, unsubstituted or substituted pyrazinyl, unsubstituted or substituted pyrimidinyl, or unsubstituted or substituted pyridinyl.

In one embodiment, Ar is unsubstituted phenyl.

In one embodiment, Ar is phenyl substituted with one or more groups independently selected from:
  a) hydroxyl, cyano, halogen (e.g., fluorine, chlorine, bromine, or iodine),
  b) unsubstituted or substituted $C_1$-$C_6$ alkyl (e.g., methyl, ethyl, n-propyl, i-propyl, n-butyl, i-butyl, s-butyl, t-butyl, n-pentyl, s-pentyl, and n-hexyl),
  c) unsubstituted or substituted amino (e.g., amino, unsubstituted or substituted $C_1$-$C_6$ alkylamino (e.g., methylamino, ethylamino, propylamino, and i-propylamino), and unsubstituted or substituted di-$C_1$-$C_6$ alkylamino (e.g., dimethylamino, diethylamino, dipropylamino, and di-i-propylamino)), and
  d) $NT_{n1}T_{n2}$,
  wherein:
    $T_{n1}$ and $T_{n2}$ are each independently H, unsubstituted or substituted $C_1$-$C_6$ alkyl (e.g., methyl, ethyl, n-propyl, i-propyl, n-butyl, i-butyl, s-butyl, t-butyl, n-pentyl, s-pentyl, and n-hexyl), or $C(O)X_1$; and
    $X_1$ is unsubstituted or substituted $C_1$-$C_6$ alkyl (e.g., methyl, ethyl, n-propyl, i-propyl, n-butyl, i-butyl, s-butyl, t-butyl, n-pentyl, s-pentyl, and n-hexyl).

In one embodiment, Ar is phenyl substituted at the para-position of the phenyl ring.

In one embodiment, Ar is phenyl substituted at the para-position of the phenyl ring with $NHC(O)X_1$.

In one embodiment, Ar is unsubstituted pyridinyl (e.g., pyridin-2-yl, pyridin-3-yl, and pyridin-4-yl).

In one embodiment, Ar is pyridinyl substituted with one or more groups independently selected from:
  a) hydroxyl, cyano, halogen (e.g., fluorine, chlorine, bromine, or iodine),
  b) unsubstituted or substituted $C_1$-$C_6$ alkyl (e.g., methyl, ethyl, n-propyl, i-propyl, n-butyl, i-butyl, s-butyl, t-butyl, n-pentyl, s-pentyl, and n-hexyl),
  c) unsubstituted or substituted amino (e.g., amino, unsubstituted or substituted $C_1$-$C_6$ alkylamino (e.g., methylamino, ethylamino, propylamino, and i-propylamino), and unsubstituted or substituted di-$C_1$-$C_6$ alkylamino (e.g., dimethylamino, diethylamino, dipropylamino, and di-i-propylamino)), and
  d) $NT_{n3}T_{n4}$,
  wherein:
    $T_{n3}$ and $T_{n4}$ are each independently H, unsubstituted or substituted $C_1$-$C_6$ alkyl (e.g., methyl, ethyl, n-propyl, i-propyl, n-butyl, i-butyl, s-butyl, t-butyl, n-pentyl, s-pentyl, and n-hexyl), unsubstituted or substituted $C_6$-$C_{10}$ aryl (e.g., phenyl and naphthyl), or $C(O)X_i$; and
    $X_1$ is unsubstituted or substituted $C_1$-$C_6$ alkyl (e.g., methyl, ethyl, n-propyl, i-propyl, n-butyl, i-butyl, s-butyl, t-butyl, n-pentyl, s-pentyl, and n-hexyl).

In one embodiment, Ar is pyridinyl substituted with halogen or unsubstituted or substituted $C_1$-$C_6$ alkyl.

In one embodiment, Ar is unsubstituted pyrimidinyl (e.g., pyrimidin-4-yl and pyrimidin-5-yl).

In one embodiment, Ar is pyrimidinyl substituted with one or more groups independently selected from:
  a) hydroxyl, cyano, halogen (e.g., fluorine, chlorine, bromine, or iodine),
  b) unsubstituted or substituted $C_1$-$C_6$ alkyl (e.g., methyl, ethyl, n-propyl, i-propyl, n-butyl, i-butyl, s-butyl, t-butyl, n-pentyl, s-pentyl, and n-hexyl),
  c) unsubstituted or substituted amino (e.g., amino, unsubstituted or substituted $C_1$-$C_6$ alkylamino (e.g., methylamino, ethylamino, propylamino, and i-propylamino), and unsubstituted or substituted di-$C_1$-$C_6$ alkylamino (e.g., dimethylamino, diethylamino, dipropylamino, and di-i-propylamino)), and
  d) $NT_{n3}T_{n4}$,
  wherein;
    $T_{n3}$ and $T_{n4}$ are each independently H, unsubstituted or substituted $C_1$-$C_6$ alkyl (e.g., methyl, ethyl, n-propyl, i-propyl n-butyl, i-butyl, s-butyl, t-butyl, n-pentyl, s-pentyl, and n-hexyl), unsubstituted or substituted $C_6$-$C_{10}$ aryl (e.g., phenyl and naphthyl), or $C(O)X_1$; and
    $X_1$ is unsubstituted or substituted $C_1$-$C_6$ alkyl (e.g., methyl, ethyl, n-propyl, i-propyl, n-butyl, i-butyl, s-butyl, t-butyl, n-pentyl, s-pentyl, and n-hexyl).

In one embodiment, Ar is pyrimidinyl substituted with $NT_{n3}T_{n4}$, and $T_{n3}$ and $T_{n4}$ are each independently H or phenyl.

In one embodiment, Ar is unsubstituted pyrazinyl.

In one embodiment, Ar is pyrazinyl substituted with one or more groups independently selected from:
  a) hydroxyl, cyano, halogen (e.g., fluorine, chlorine, bromine, or iodine),
  b) unsubstituted or substituted $C_1$-$C_6$ alkyl (e.g., methyl, ethyl, n-propyl, i-propyl, n-butyl, i-butyl, s-butyl, t-butyl, n-pentyl, s-pentyl, and n-hexyl),
  c) unsubstituted or substituted amino (e.g., amino, unsubstituted or substituted $C_1$-$C_6$ alkylamino (e.g., methylamino, ethylamino, propylamino, and i-propylamino), and unsubstituted or substituted di-$C_1$-$C_6$ alkylamino (e.g., dimethylamino, diethylamino, dipropylamino, and di-i-propylamino)), and
  d) $NT_{n3}T_{n4}$,
  wherein:
    $T_{n3}$ and $T_{n4}$ are each independently H, unsubstituted or substituted $C_1$-$C_6$ alkyl (e.g., methyl, ethyl, n-propyl, i-propyl, n-butyl, i-butyl, s-butyl, t-butyl, n-pentyl, s-pentyl, and n-hexyl), unsubstituted or substituted $C_6$-$C_{10}$ aryl (e.g., phenyl and naphthyl), or $C(O)X_1$; and
    $X_1$ is unsubstituted or substituted $C_1$-$C_6$ alkyl (e.g., methyl, ethyl, n-propyl, i-propyl, n-butyl, i-butyl, s-butyl, t-butyl, n-pentyl, s-pentyl, and n-hexyl).

The present invention also provides compounds of formula Ia, Ib, or Ic:

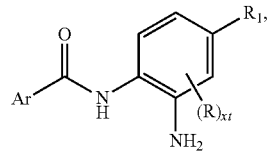

(Ia)

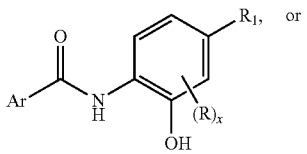

(Ib)

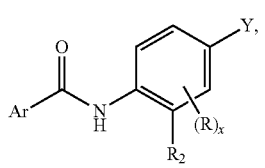

(Ic)

wherein:
Ar is unsubstituted or substituted phenyl, unsubstituted or substituted pyrazinyl, unsubstituted or substituted pyrimidinyl, unsubstituted or substituted pyridinyl, unsubstituted or substituted quinolinyl, unsubstituted or substituted isoquinolinyl, unsubstituted or substituted quinazolinyl, or unsubstituted or substituted quinoxalinyl;

$R_1$ and $R_2$ are each independently H, hydroxyl, cyano, halogen, unsubstituted or substituted amino, unsubstituted or substituted $C_1$-$C_6$ alkyl, or unsubstituted or substituted $C_1$-$C_6$ alkoxy;

each R is independently hydroxyl, cyano, halogen, unsubstituted or substituted amino, unsubstituted or substituted $C_1$-$C_6$ alkyl, unsubstituted or substituted $C_1$-$C_6$ alkoxy, or unsubstituted or substituted $C_6$-$C_{10}$ aryl;

Y is halogen;
x is 0, 1, 2, or 3; and
xt is 0, 1, 2, or 3,
provided that when Ar is unsubstituted pyrazinyl, xt is not 0,
or a pharmaceutically acceptable salt, ester, solvate, or prodrug thereof.

In various embodiments, Ar, $R_1$, $R_2$, R, and x are each, alone or in combination with one another, substituent groups listed in the embodiments for Ar, $R_1$, $R_2$, R, and x for the compounds of formula 1.

In one embodiment, Y is fluorine, chlorine, bromine, or iodine.

In one embodiment, Y is fluorine.
In one embodiment, xt is 0.
In one embodiment, xt is 1.
In one embodiment, xt is 2.

The present invention also provides compounds of one of formulae I1-I6, Ia1-Ia6, Ib1-Ib6, and Ic1-Ic6:

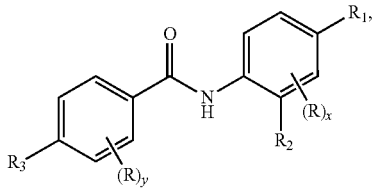

(I1)

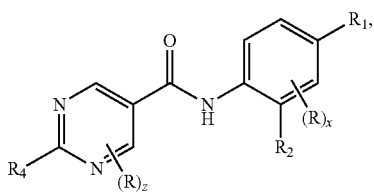

(I2)

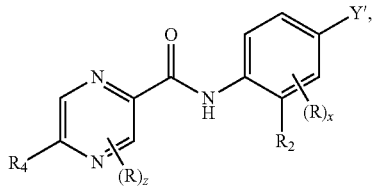

(I3)

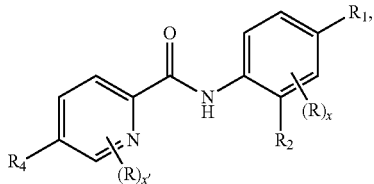

(I4)

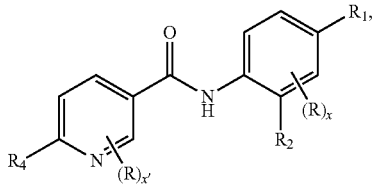

(I5)

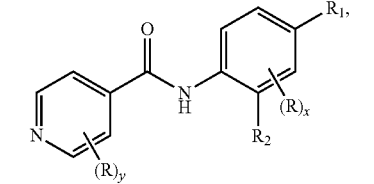

(I6)

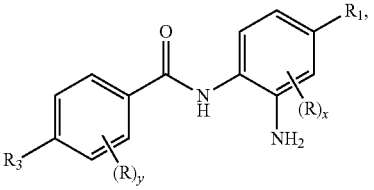

(Ia1)

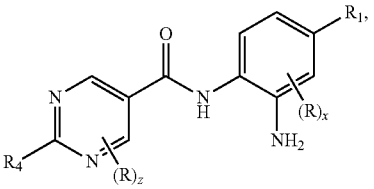

(Ia2)

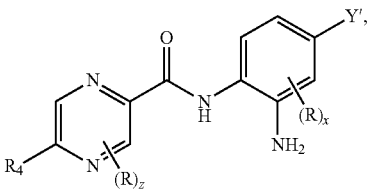

(Ia3)

(Ia4) 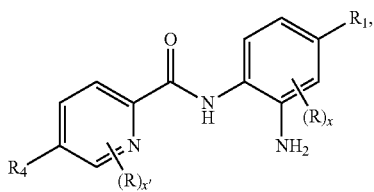

(Ia5) 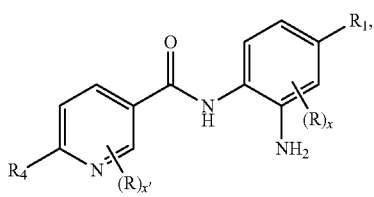

(Ia6) 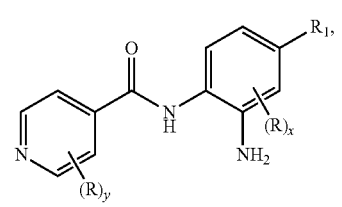

(Ib1) 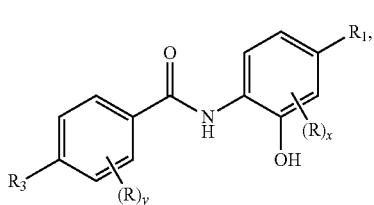

(Ib2) 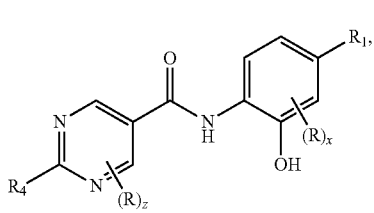

(Ib3) 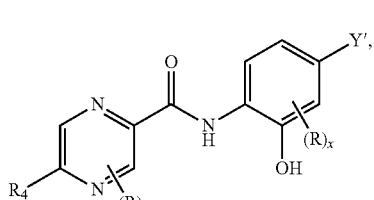

(Ib4) 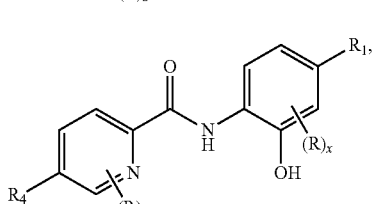

(Ib4) 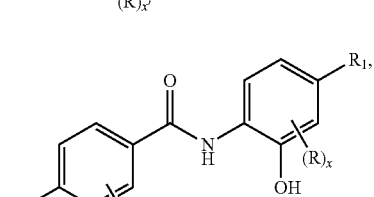

(Ib5) 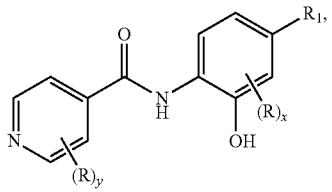

(Ic1) 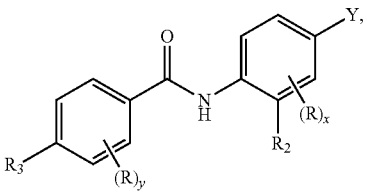

(Ic2) 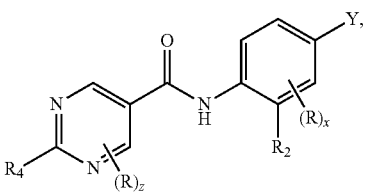

(Ic3) 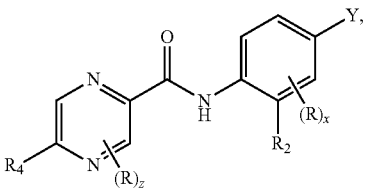

(Ic4) 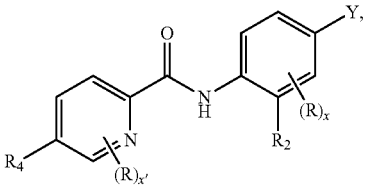

(Ic5) 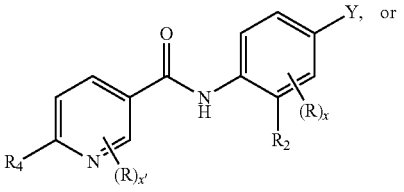

(Ic6) 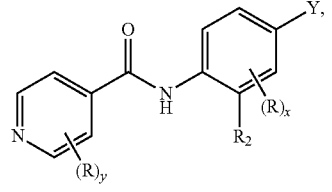

wherein:

$R_1$ and $R_2$ are each independently H, hydroxyl, cyano, halogen, unsubstituted or substituted amino, unsubstituted or substituted $C_1$-$C_6$ alkyl, or unsubstituted or substituted $C_1$-$C_6$ alkoxy;

each R is independently hydroxyl, cyano, halogen, unsubstituted or substituted amino, unsubstituted or substituted $C_1$-$C_6$ alkyl, unsubstituted or substituted $C_1$-$C_6$ alkoxy, or unsubstituted or substituted $C_6$-$C_{10}$ aryl;

Y' is hydroxyl, cyano, halogen, unsubstituted or substituted amino, unsubstituted or substituted $C_1$-$C_6$ alkyl, or unsubstituted or substituted $C_1$-$C_6$ alkoxy;

Y is halogen;

x is 0, 1, 2, or 3;

x' is 0, 1, 2, or 3;

y is 0, 1, 2, 3, or 4;

z is 0, 1, or 2;

$R_3$ is H, unsubstituted or substituted $C_1$-$C_6$ alkyl, halogen, or $NT_{n1}T_{n2}$;

$T_{n1}$ and $T_{n2}$ are each independently H, unsubstituted or substituted $C_1$-$C_6$ alkyl, or $C(O)X_1$;

$R_4$ is H, unsubstituted or substituted $C_1$-$C_6$ alkyl, halogen, or $NT_{n3}T_{n4}$;

$T_{n3}$ and $T_{n4}$ are each independently H, unsubstituted or substituted $C_1$-$C_6$ alkyl, unsubstituted or substituted $C_6$-$C_{10}$ aryl, or $C(O)X_1$; and $X_1$ is unsubstituted or substituted $C_1$-$C_6$ alkyl, or a pharmaceutically acceptable salt, ester, solvate, or prodrug thereof.

In various embodiments, Ar, $R_1$, $R_2$, R, Y, and x are each, alone or in combination with one another, substituent groups listed in the embodiments for Ar, $R_1$, $R_2$, R, Y, and x for the compounds of any one of formulae I, Ia, Ib, and Ic.

In one embodiment, x' is 0.
In one embodiment, x' is 1.
In one embodiment, x' is 2.
In one embodiment, y is 0.
In one embodiment, y is 1.
In one embodiment, y is 2.
In one embodiment, z is 0.
In one embodiment, z is 1.
In one embodiment, $R_3$ is H.
In one embodiment, $R_3$ is unsubstituted or substituted $C_1$-$C_6$ alkyl, e.g., straight chain $C_1$-$C_6$ alkyl or branched $C_3$-$C_6$ alkyl, including but not limited to, methyl, ethyl, n-propyl, i-propyl n-butyl i-butyl, s-butyl, t-butyl n-pentyl, s-pentyl, and n-hexyl, each of which is optionally substituted.

In one embodiment, $R_3$ is unsubstituted methyl or ethyl.
In one embodiment, $R_3$ is halogen (e.g., fluorine, chlorine, bromine, and iodine).
In one embodiment, $R_3$ is fluorine or chlorine.
In one embodiment, $R_3$ is $NT_{n1}T_{n2}$, wherein $T_{n1}$ is H or unsubstituted or substituted $C_1$-$C_6$ alkyl (e.g., methyl, ethyl, n-propyl, i-propyl n-butyl, i-butyl, s-butyl, t-butyl, n-pentyl, s-pentyl, and n-hexyl), and is $C(O)X_1$.

In one embodiment, $X_1$ is unsubstituted or substituted $C_1$-$C_6$ alkyl, e.g., straight chain $C_1$-$C_6$ alkyl or branched $C_3$-$C_6$ alkyl, including but not limited to, methyl, ethyl, n-propyl, i-propyl, n-butyl, i-butyl, s-butyl, t-butyl, n-pentyl, s-pentyl, and n-hexyl, each of which is optionally substituted.

In one embodiment, $X_1$ is unsubstituted methyl or ethyl.
In one embodiment, $R_4$ is H.
In one embodiment, $R_4$ is unsubstituted or substituted $C_1$-$C_6$ alkyl, e.g., straight chain $C_1$-$C_6$ alkyl or branched $C_3$-$C_6$ alkyl, including but not limited to, methyl, ethyl, n-propyl, i-propyl, n-butyl, i-butyl, s-butyl t-butyl, n-pentyl, s-pentyl, and n-hexyl, each of which is optionally substituted.

In one embodiment, $R_4$ is unsubstituted methyl or ethyl.
In one embodiment, $R_4$ is halogen (e.g., fluorine, chlorine, bromine, and iodine).
In one embodiment, $R_4$ is fluorine or chlorine.
In one embodiment, $R_4$ is $NT_{n3}T_{n4}$, wherein $T_{n3}$ is H or unsubstituted or substituted $C_1$-$C_6$ alkyl (e.g., methyl, ethyl, n-propyl, i-propyl, n-butyl, i-butyl, s-butyl, t-butyl, n-pentyl, s-pentyl, and n-hexyl), and $T_{n4}$ is unsubstituted or substituted $C_6$-$C_{10}$ aryl (e.g., phenyl or naphthyl).

In one embodiment, Y' is halogen (e.g., fluorine, chlorine, bromine, and iodine).

In one embodiment, Y' is fluorine.

In one embodiment, Y' is unsubstituted amino or amino mono- or di-substituted with $C_1$-$C_6$ alkyl (e.g., methyl, ethyl, propyl, and butyl).

In one embodiment, Y' is unsubstituted or substituted $C_1$-$C_6$ alkyl, e.g., straight chain $C_1$-$C_6$ alkyl or branched $C_3$-$C_6$ alkyl, including but not limited to, methyl, ethyl, n-propyl, i-propyl, n-butyl, i-butyl, s-butyl, t-butyl, n-pentyl, s-pentyl, and n-hexyl, each of which is optionally substituted.

In one embodiment, Y' is unsubstituted or substituted $C_1$-$C_6$ alkoxy (e.g., methoxy, ethoxy, propyloxy, i-propyloxy, butoxy, and t-butoxy).

Representative compounds of the invention include those listed in Table 1.

TABLE 1

| # | Chemical Structure |
|---|---|
| 1 | 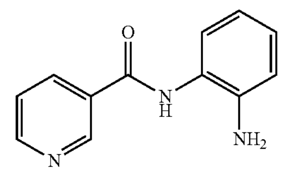 [SMILES: Nc1ccccc1NC(=O)c1cccnc1] |
| 2 | 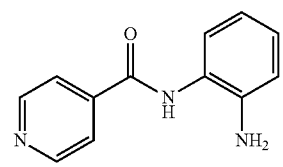 [SMILES: Nc1ccccc1NC(=O)c1ccncc1] |
| 3 | 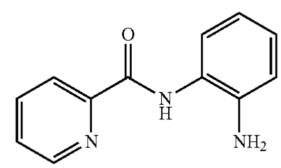 [SMILES: Nc1ccccc1NC(=O)c1ccccn1] |
| 17 | 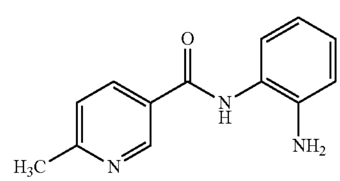 [SMILES: Cc1ccc(C(=O)Nc2ccccc2N)cn1] |
| 5 | 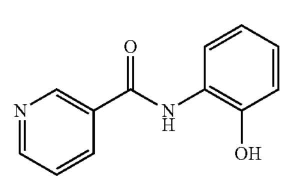 [SMILES: O=C(Nc1ccccc1O)c1cccnc1] |
| 6 | 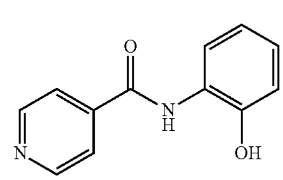 [SMILES: O=C(Nc1ccccc1O)c1ccncc1] |

TABLE 1-continued

| # | Chemical Structure |
|---|---|
| 7 | (2-pyridinecarboxamide with 2-hydroxyphenyl) |
| 8 | (2-phenylamino-pyrimidine-5-carboxamide with 2-aminophenyl) |
| 9 | (6-chloro-pyridine-3-carboxamide with 2-aminophenyl) |
| 10 | (pyrazine-2-carboxamide with 2-aminophenyl) |
| 11 | (4-acetamido-benzamide with biphenyl-2-amine) |
| 12 | (4-acetamido-benzamide with 4-fluoro-2-aminophenyl) |
| 13 | (pyridine-3-carboxamide with 4-fluoro-2-aminophenyl) |
| 14 | (pyrazine-2-carboxamide with 4-fluoro-2-aminophenyl) |
| 15 | (pyridine-3-carboxamide with 4-fluoro-2-hydroxyphenyl) |
| 16 | (4-acetamido-benzamide with 2-aminophenyl) |

In one embodiment, a compound of the present invention is an inhibitor of an HDAC. In one embodiment, a compound of the present invention is a selective inhibitor of a specific class of HDAC. For example, a compound of the present invention is an inhibitor of class-1 HDACs (e.g., HDAC1, 2, 3, or 8). For example, a compound of the present invention is an inhibitor of HDAC3.

In one embodiment, a compound of the present invention is an inhibitor of HDACs1, 2, 3, or 8. Preferably, a compound of the present invention is a selective inhibitor of HDACs1, 2, or 3. More preferably, a compound of the present invention is a selective inhibitor of HDAC3.

As used herein, "specific", "specificity", or "selective" or "selectivity" as used when describing a compound as an inhibitor, means that the compound preferably interacts with (e.g., binds to, modulates, and inhibits) a particular target (e.g., a protein and an enzyme) than a non-target. For example, the compound has a higher affinity, a higher avidity, a higher binding coefficient, or a lower dissociating coefficient for a particular target. The specificity or selectivity of a compound for a particular target can be measured, determined, or assessed by using various methods well known in the art. For example, the specificity or selectivity can be measured, determined, or assessed by measuring the $IC_{50}$ of a compound for a target. A compound is specific or selective for a target when the $IC_{50}$ of the compound for the target is 2-fold, 4-fold, 6-fold, 8-fold, 10-fold, 20-fold, 50-fold, 100-fold, 500-fold, 1000-fold, or more lower than the $IC_{50}$ of the same compound for a non-target. For example, the $IC_{50}$ of a compound of the present invention for HDACs is 2-fold, 4-fold, 6-fold, 8-fold, 10-fold, 20-fold, 50-fold, 100-fold, 500-fold, 1000-fold, or more lower than the $IC_{50}$ of the same compound for non-HDACs. For example, the $IC_{50}$ of a compound of the present invention for class-I HDACs is 2-fold, 4-fold, 6-fold, 8-fold, 10-fold, 20-fold, 50-fold, 100-fold, 500-fold, 1000-fold, or more lower than the $IC_{50}$ of the same compound, for other HDACs (e.g., class-II HDACs). For example, the $IC_{50}$ of a compound of the present invention for HDAC3 is 2-fold, 4-fold, 6-fold, 8-fold, 10-fold, 20-fold, 50-fold, 100-fold, 500-fold, 1000-fold, or more lower than the $IC_{50}$ of the same compound for other HDACs (e.g., HDAC1, 2, or 6). $IC_{50}$ can be determined by commonly known methods in the art, such as those described herein.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ or $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

The term "substituted alkyl" refers to alkyl moieties having substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonate, sulfamoyl, sulfonamide, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

Unless the number of carbons is otherwise specified, "lower alkyl" includes an alkyl group, as defined above, having from one to six, or in another embodiment from one to four, carbon atoms in its backbone structure.

"Aryl" includes groups with aromaticity, including "conjugated", or multicyclic, systems with at least one aromatic ring. Examples include phenyl, benzyl, etc.

"Heteroaryl" groups are aryl groups, as defined above, having from one to four heteroatoms in the ring structure, and may also be referred to as "aryl heterocycles" or "heteroaromatics". As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthridine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The aryl or heteroaryl aromatic ring can be substituted at one or more ring positions with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonate, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" includes any ring structure (saturated or partially unsaturated) which contains at least one ring heteroatom (e.g., N, O or S). Examples of heterocycles include, but are not limited to, morpholine, pyrrolidine, tetrahydrothiophene, piperidine, piperazine and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolmyl, benzthiazolyl, benztriazolyl, benztatrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinly, naphthyridinyl, octahydroisoquinolinyl, oxadiazolyl, 1,2,3-oxadiazolyl, 1,2,4-oxadiazolyl, 1,2,5-oxadizaolyl, 1,3,4-oxadiazolyl, 1,2,4-oxadiazol5(4H)-one, oxazolindinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothtazole, pyridinyl, pyridyl, pyrimidinyl, pyrrolidinyl, pyrrolinyl, 2H-pyrrolyl, pyrrolyl, quinzaolinyl, quinolinyl, 4H-quinolizinyl, quinoxalinyl, quinuclidinyl, tetrahydrofuranyl, tetrahydroisoquinolinly, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienoozazolyl, thienoimidazolyl, thiophenyl, triazinyl, 1,2,3-triazolyl, 1,2, 4-triazolyl, 1,2,5-triazolyl, 1,3,4-triazolyl and xanthenyl.

The term "substituted", as used herein, means that any one or more hydrogen atoms on the designated atom is replaced with a selection from the indicated groups, provided that the designated atom's normal valency is not exceeded, and that the substitution results in a stable compound. When a substituent is keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$. Also, combinations of substituents and/or variables are permissible, but only if such combinations result in stable compounds.

The term "hydroxy" or "hydroxyl" includes groups with an —OH or —O⁻.

As used herein, "halo" or "halogen" refers to fluoro, chloro, bromo and iodo. The term "perhalogenated" generally refers to a moiety wherein all hydrogen atoms are replaced by halogen atoms.

The term "carbonyl" or "carboxy" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

"Acyl" includes moieties that contain the acyl radical (—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl; or an aromatic or heteroaromatic moiety.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen bonded to two carbon atoms or heteroatoms. For example, the term includes "alkoxyalkyl", which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

As used herein, "amine" or "amino" includes moieties where a nitrogen atom is covalently bonded to at least one carbon or heteroatom. "Alkylamino" includes groups of compounds wherein nitrogen is bound to at least one alkyl group. Examples of alkylamino groups include benzylamino, methylamino, ethylamino, phenethylamino, etc. "Dialkylamino" includes groups wherein the nitrogen atom is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively. "Alkylarylamino", "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

Compounds of the present invention that contain nitrogens can be converted to N-oxides by treatment with an oxidizing agent (e.g., 3-chloroperoxybenzoic acid (m-CPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present invention. Furthermore, so-called metabolite which is produced by degradation of the present compound in vivo is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four nonidentical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Calm et. al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this invention include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine.

It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula I have Formula I as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, Chem. Rev. 96, 3147-3176, 1996.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

In certain embodiments, the invention relates to any one of the aforementioned compounds, provided the compound is not 4-(acetylamino)-N-(2-aminophenyl)benzamide, 4-acetamido-N2-amino-5-(thiophen-2-yl)phenyl)benzamide, entinostat, rocilinostat (ACY-1215), or pyridin-3-ylmethyl N-[[4-[(2-aminophenyl)carbamoyl]phenyl]methyl]carbamate.

In certain embodiments, the invention relates to any one of the aforementioned compounds, provided the compound is not

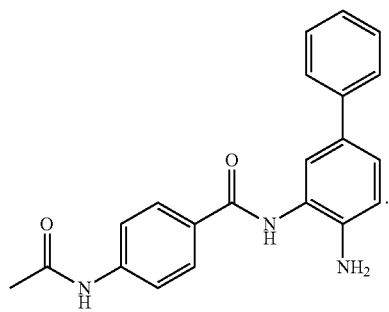 [SMILES: CC(=O)Nc1ccc(C(=O)Nc2cc(-c3ccccc3)ccc2N)cc1]

2. Synthesis of the Compounds of the Invention

The present invention provides methods for the synthesis of the compounds of each of the formulae described herein. The present invention also provides detailed methods for the synthesis of various disclosed compounds of the present invention according to the following schemes as shown in the examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester or prodrug thereof.

Compounds of fee present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., March's Advanced Organic Chemistry: Reactions, Mechanisms, and Structure, $5^{th}$ edition, John Wiley & Sons: New York, 2001; and Greene, T. W., Wuts, P. G. M., Protective Groups in Organic Synthesis, $3^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present invention.

Compounds of the present invention can be conveniently prepared by a variety of methods familiar to those skilled in the art. The compounds each of the formulae described herein may be prepared according to the following procedures from commercially available starting materials or starting materials which can be prepared using literature procedures. These procedures show the preparation of representative compounds of this invention.

General Procedure A

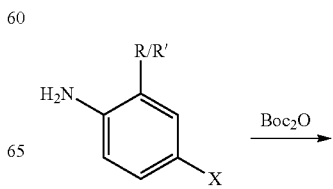

-continued

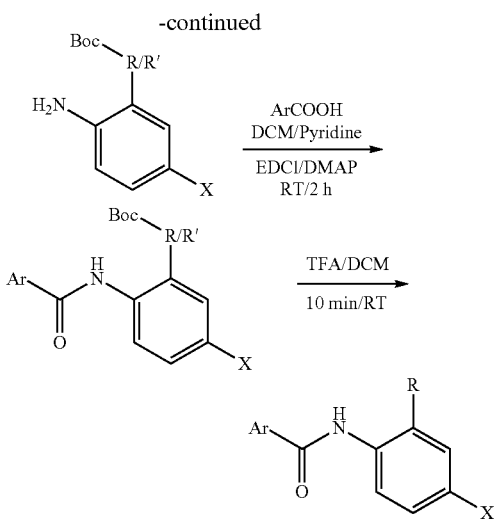

General Procedure B

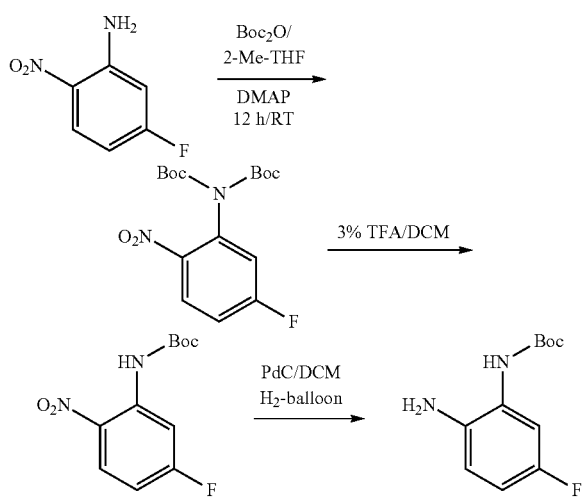

3. Methods of Treatment

The present invention provides methods for the treatment of a hematological cell proliferative disorder in a subject in need thereof by administering to a subject in need of such treatment, a therapeutically effective amount of a compound of the present invention, or a pharmaceutical acceptable salt, ester, solvate, or prodrug thereof. The hematological cell proliferative disorder can be cancer or a precancerous condition. The present invention further provides the use of a compound of the present invention, or a pharmaceutically acceptable salt, ester, solvate, or prodrug thereof, for the preparation of a medicament useful for the treatment of a hematological cell proliferative disorder. In one embodiment, the compound of the present invention administered to the subject is a selective HDAC inhibitor. In a preferred embodiment, the compound of the present invention administered to the subject is a selective class-I HDAC inhibitor. In a more preferred embodiment, the compound of the present invention administered to the subject is a selective HDAC3 inhibitor.

The present invention also provides methods of protecting against a hematological cell proliferative disorder in a subject in need thereof by administering a therapeutically effective amount of compound of the present invention, or a pharmaceutically acceptable salt, ester, solvate, or prodrug thereof, to a subject in need of such treatment. The hematological cell proliferative disorder can be cancer or a precancerous condition. The present invention also provides the use of compound of the present invention, or a pharmaceutically acceptable salt, ester, solvate, or prodrug thereof, for the preparation of a medicament useful for the prevention of a hematological cell proliferative disorder. In one embodiment, the compound of the present invention administered to the subject is a selective HDAC inhibitor. In a preferred embodiment, the compound of the present invention administered to the subject is a selective class-I HDAC inhibitor. In a more preferred embodiment, the compound of the present invention administered to the subject is a selective HDAC3 inhibitor.

The present invention provides methods for the treatment of a multiple myeloma in a subject in need thereof by administering to a subject in need of such treatment, a therapeutically effective amount of a compound of the present invention, or a pharmaceutically acceptable salt, ester, solvate, or prodrug thereof. The present invention further provides the use of a compound of the present invention, or a pharmaceutically acceptable salt, ester, solvate, or prodrug thereof, for the preparation of a medicament useful for the treatment of a multiple myeloma. In one embodiment, the multiple myeloma is a relapsed and/or refractory multiple myeloma. In one embodiment, the compound of the present invention administered to the subject is a selective HDAC inhibitor. In a preferred embodiment, the compound of the present invention administered to the subject is a selective class-I HDAC inhibitor. In a more preferred embodiment, the compound of the present invention administered to the subject is a selective HDAC3 inhibitor.

The present invention also provides methods of protecting against a multiple myeloma in a subject in need thereof by administering a therapeutically effective amount of compound of the present invention, or a pharmaceutically acceptable salt, ester, solvate, or prodrug thereof to a subject in need of such treatment. The present invention also provides the use of compound of the present invention, or a pharmaceutically acceptable salt, ester, solvate, or prodrug thereof, for the preparation of a medicament useful for the prevention of a multiple myeloma. In one embodiment, the multiple myeloma is a relapsed and/or refractory multiple myeloma. In one embodiment, the compound of the present invention administered to the subject is a selective HDAC inhibitor. In a preferred embodiment, the compound of the present invention administered to the subject is a selective class-I HDAC inhibitor. In a more preferred embodiment, the compound of the present invention administered to the subject is a selective HDAC3 inhibitor.

In certain embodiments, the invention relates to a method of enhancing long-term memory in a subject in need thereof by administering a therapeutically effective amount of compound of the present invention, or a pharmaceutically acceptable salt, ester, solvate, or prodrug thereof, to a subject in need of such treatment. In certain embodiments, the invention relates to any one of the aforementioned methods, wherein, long-term memory is enhanced in a persistent manner, in certain embodiments, the invention relates to any one of the aforementioned methods, wherein synaptic plasticity is enhanced. In certain embodiments, the invention relates to any one of the aforementioned methods, wherein the method transforms a learning event that does not lead to long-term memory into a learning event that does result in significant long-term memory. In certain embodiments, the invention relates to any one of the aforementioned methods, wherein the method generates a form of long-term memory that persists beyond the point at which normal memory fails.

In certain embodiments, the invention relates to a method of treating or preventing a cognitive disorder in a subject in need thereof by administering a therapeutically effective amount of compound of the present invention, or a pharmaceutically acceptable salt, ester, solvate, or prodrug thereof, to a subject in need of such treatment. In certain embodiments, the invention relates to any one of the aforementioned methods, wherein the cognitive disorder is post-traumatic stress disorder or an anxiety disorder.

In certain embodiments, the invention relates to a method of treating or preventing a cognitive deficit in a subject in need thereof by administering a therapeutically effective amount of compound of the present invention, or a pharmaceutically acceptable salt, ester, solvate, or prodrug thereof, to a subject in need of such treatment. In certain embodiments, the invention relates to any one of the aforementioned methods, wherein the cognitive deficit is a result of Alzheimer's disease.

In certain embodiments, the invention relates to a method of facilitating the extinction, of drug-seeking behavior in a subject in need thereof by administering a therapeutically effective amount of compound of the present invention, or a pharmaceutically acceptable salt, ester, solvate, or prodrug thereof, to a subject in need of such treatment. In certain embodiments, the invention relates to any one of the aforementioned methods, wherein the drug-seeking behavior is extinguished in a manner resistant to reinstatement.

In certain embodiments, the invention relates to any one of the aforementioned methods, further comprising administering to the subject a second therapeutic agent. The second therapeutic agent can be any agent used for treating a hematological cell proliferative disorder, including, but not limited to, HDAC inhibitors, proteasomal inhibitors, deubiquitinase inhibitors, demethylase inhibitors, endoplasmic reticulum (ER) stressors, JNK inhibitors, and caspase inhibitors.

The methods of protecting against a hematological, cell proliferative disorder of the present invention can further comprise administering to the subject a second therapeutic agent. The second therapeutic agent can be any agent used for protecting against a hematological cell proliferative disorder, including, but not limited to, HDAC inhibitors, proteasomal inhibitors, deubiquitinase inhibitors, demethylase inhibitors, endoplasmic reticulum (ER) stressors, JNK inhibitors, and caspase inhibitors.

In some embodiments, a compound of the invention is administered in combination with a proteasomal inhibitor.

Examples of proteasomal inhibitors include but are not limited to bortezomib, carfilzomib, MLN9708, MLN2238, PR-924, NP10052, nucleotide-based inhibitors, and protein or peptide-based inhibitors.

For example, bortezomib (e.g., VELCADE, Millennium Pharmaceuticals, Inc., Cambridge, Mass.) is a modified dipeptidyl boronic acid. Bortezomib is a reversible inhibitor of the 26S proteasome in mammalian cells. Inhibition of the 26S proteasome prevents targeted proteolysis, which can affect multiple signaling cascades within the cell. This disruption of normal homeostatic mechanisms can lead to cell death. Experiments have demonstrated that bortezomib is cytotoxic in vitro and causes a delay in cell growth in vivo. Although Bortezomib has been shown to be effective for the treatment of MM, dose-limiting toxicities and the development of resistance limit its long-term use. See, e.g., Chauhan D. et al. *Clin. Cancer Res.* 2011. 17(16):5311-21. The chemical name for bortezomib, the monomeric boronic acid, is [(1R)-3-methyl-1-[[(2S)-1-oxo-3-phenyl-2-[(pyrazinylcarbonyl)amino]propyl]amino]butyl]boronic acid, as represented by the following structure:

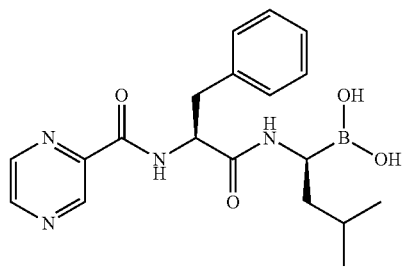 [SMILES: CC(C)C[C@@H](NC(=O)[C@H](Cc1ccccc1)NC(=O)c1cnccn1)B(O)O]

For example, carfilzomib (marketed under the trade name KYPROLIS is a tetrapeptide epoxyketone and a selective proteasome inhibitor. It is an analog of epoxomicin. Carfilzomib has been approved by the US FDA for use in patients with multiple myeloma who have received at least two prior therapies, including treatment with bortezomib and an immunomodulatory therapy and have demonstrated disease progression on or within 60 days of completion of the last therapy. See, e.g., "Highlights of Prescribing Information: Kyprolis." FDA ID: 3161927 (July 2012). The structure of carfilzomib is shown below:

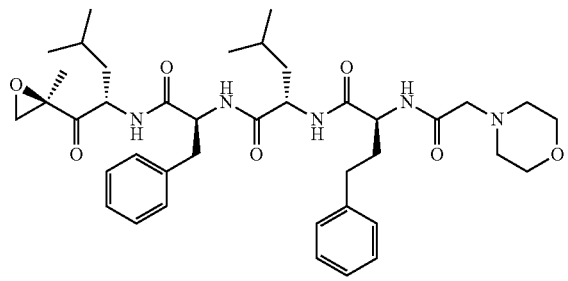 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

For example, MLN9708 (Ixazomib, Millennium Pharmaceuticals, Inc.) is also a proteasome inhibitor, and it has a shorter proteasome dissociation half-life than bortezomib. MLN9708 also has improved pharmacokinetics, pharmacodynamics, and antitumor activity in xenograft models compared to bortezomib. See, e.g., Kupperman E. et al. *Cancer Res.* 2010. 70; 1970-1980. Upon exposure to aqueous solutions and/or plasma, MLN9708 rapidly hydrolyzes to its biologically active form—MLN2238.

MLN2238 is a boronic acid analog that inhibits the proteasome. MLN2238 predominantly inhibits the chymotrypsin-like activity of the proteasome, causing accumulation of ubiquitinated proteins. MLN2238 has been shown to inhibit growth and induce apoptosis in MM cells that are resistant to conventional and bortezomib therapies without having an effect on the viability of normal cells. In animal tumor model studies, MLN2238 has been shown to be well-tolerated and inhibits tumor growth with significantly decreased tumor recurrence. See, e.g., Chauhan D, et al. *Clin. Cancer Res.* 2011. 17(16):5311-21. The structure of MLN2238 is shown below:

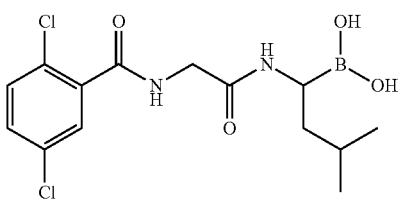 [SMILES: CC(C)CC(NC(=O)CNC(=O)c1cc(Cl)ccc1Cl)B(O)O]

For example, NPI-0052 (Salinosporamide A) is a potent proteasome inhibitor that induces apoptosis in multiple myeloma cells. Salinosporamide A inhibits proteasome activity by covalently modifying the active site threonine residues of the 20S proteasome. See, e.g., Chauhan, D. et al. *British J. Cancer* 2006. 95:961-965. Salinosporamide A is member of the family of compounds, known collectively as salinosporamides, which have a densely functionalized γ-lactam-β-lactone bicyclic core. See, e.g., Feling R. et al. 2003. *Angew. Chem. Inl. Ed. Engl.* 42 (3): 355-7; and Chauhan, D. et al. 2005. *Cancer Cell* 8(5):407-19. The structure of NPI-0052 is shown below:

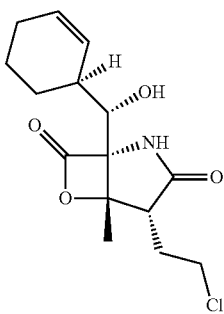 [SMILES: C[C@@]12OC(=O)[C@]1([C@@H](O)[C@@H]1C=CCCC1)NC(=O)[C@@H]2CCCl]

Nucleotide based inhibitors of a proteasome can include but are not limited to short hairpin RNA (shRNA), RNA interference (RNAi), short interfering RNA (siRNA), microRNA (miRNA), locked nucleic acids (LNA), DMA, peptide-nucleic acids (PNA), morpholinos, and aptamers. In some embodiments, nucleotide based inhibitors are composed of at least one modified base. In some embodiments, nucleotide based inhibitors bind to the mRNA of a proteasomal protein and decrease or inhibit its translation, or increase its degradation. In some embodiments, nucleotide based inhibitors decrease the expression (e.g., at the mRNA transcript and/or protein level) of a proteasome or subunit thereof in cells and/or in a subject. In some embodiments, nucleotide based inhibitors bind to a proteasomal protein or subunit thereof and decrease its proteasomal activity.

Protein or peptide based inhibitors of a proteasome can include but are not limited to peptides, recombinant proteins, and antibodies or fragments thereof. Protein or peptide based inhibitors can be composed of at least one non-natural amino acid. In some embodiments protein or peptide based inhibitors decrease the expression (e.g., at the mRNA transcript and/or protein level) of a proteasome or subunit thereof in cells and/or in a subject. In some embodiments, protein or peptide based inhibitors bind to a proteasomal protein or subunit thereof and decrease its proteasomal activity.

In some embodiments, a compound of the invention is administered in combination with a demethylase inhibitor. Examples of demethylase inhibitors include but are not limited to LSD-1, JMJD3, daminozide, GSK J1, GSK J4, IOX 1, 2,4-pyridinedicarboxylic acid, nucleotide-based inhibitors, and protein or peptide-based inhibitors.

The histone H3 lysine 27 (H3K27) demethylase JMJD3 plays important roles in the transcriptional regulation of cell differentiation, development, the inflammatory response, and cancer. See, e.g., Agger et al. *Nat. Letters.* 2011. 499(7163):731-4.

For example, daminozide (CAS 1596-84-5) has the chemical name, 1-(2,2-dimethylhydrazide)-butanedioic acid. Daminozide is a highly selective inhibitor of the human 2-oxoglutarate (JmjC) histone demethylases KDM2A, PHF8, and KDM7A with $IC_{50}$ values of 1.5, 0.55, and 2.1 µM, respectively. See, e.g., Rose et al. *J. Med Chem.* 2012. 55:6639-6643.

For example, GSK J1 is a potent H3K27 histone demethylase inhibitor that is highly selective for human JMJD3 ($IC_{50}$=60 nM in vitro). GSK J1 is inactive against a panel of additional JMJ family demethylases, including several variants of JMJD2 and JMJD1 and has no effect on more than 100 different kinases or other unrelated proteins, including other chromatin-modifying enzymes such as histone deacetylases at concentrations of up to 30 µM. See, e.g., Kruidenier et al. *Nature.* 2012. 488:404-408. The chemical name of GSK J1 is 3-((6-(4,5-dihydro-1H-benzo[d]azepin-3(2H)-yl)-2-(pyridin-2-yl)pyrimidin-4-yl)amino)propanoate, monosodium salt.

For example, GSK-J4 (hydrochloride) is an ethyl ester derivative of the JMJD3 selective histone demethylase inhibitor GSK-J1. GSK-J4 has an IC50 value greater than 50 µM in vitro. As a prodrug, GSK-J4 is rapidly hydrolyzed in cells to the otherwise cell impermeable GSK-J1, which exhibits an IC50 value of 60 nM for the purified enzyme. When administered to human primary macrophages, GSK-J4 can reduce LPS-induced proinflammatory cytokine production, including that of TNFα. See, e.g., Kruidenier et. al. *Nature.* 2012. 488:404-408. The chemical name of GSK-J4 is ethyl 3-((6-(4,5-dihydro-1H-benzo[d]azepin-3(2H)-yl)-2-(pyridin-2-yl)pyrimidin-4-yl)amino)propanoate, monohydrochloride.

For example, IOX1 is a broad-spectrum inhibitor of 2OG oxygenases that does not require application in a pro-drug formulation 2-oxoglutarate (2OG) and other Fe(II)-dependent oxygenases are a family of enzymes with roles in collagen biosynthesis, lipid metabolism, nucleic acid repair and modification, histone demethylation, and hypoxic sensing. Impaired 2OG oxygenase activity is linked to the cellular hypoxic response and various diseases including cancer. IOX1 inhibits JMJD2A, JMJD2E and the 2OG oxygenases PHF8, PHD2, and FIH with $IC_{50}$ values of 1.7, 2.4, 13.3, 14.3, and 20.5 µM, respectively. IOX1 inhibits H3K9me3 demethylation by JMJD2A in HeLa cells with an $IC_{50}$ value of 87 µM. See, e.g., King et al. PLos One. 2010, 5(11):1-12. The chemical name of IOX1 is 8-hydroxy-5-quinolinecarboxylic acid.

Nucleotide based inhibitors of a demethylase enzyme can include but are not limited to short hairpin RNA (shRNA), RNA interference (RNAi), short interfering RNA (siRNA), microRNA (miRNA), locked nucleic acids (LNA), DNA, peptide-nucleic acids (PNA), morpholinos, and aptamers. In some embodiments, nucleotide based inhibitors are composed of at least one modified base. In some embodiments, nucleotide based inhibitors bind to the mRNA of a demethylase and decrease or inhibit its translation, or increase its degradation. In some embodiments, nucleotide based inhibitors decrease the expression (e.g., at the mRNA transcript and/or protein level) of a demethylase in cells and/or in a subject. In some embodiments, nucleotide based inhibitors bind to a demethylase and decrease its enzymatic activity.

Protein or peptide based inhibitors of a demethylase can include but are not limited to peptides, recombinant proteins, and antibodies or fragments thereof. Protein or peptide based inhibitors can be composed of at least one non-natural amino acid. In some embodiments protein or peptide based inhibitors decrease the expression (e.g., at the mRNA transcript and/or protein level) of a demethylase in cells and/or in a subject. In some embodiments, protein or peptide based inhibitors bind to a demethylase and decrease its enzymatic activity.

In some embodiments, a compound of the invention is administered in combination with a second HDAC inhibitor.

The second HDAC inhibitor can be a selective inhibitor of a specific HDAC or a specific class of HDACs. The second HDAC inhibitor can include an inhibitor of class-I (HDAC1, 2, 3, 8), class-IIa (HDAC4, 5, 7, 9), class-IIb (HDAC6,10), class-III (SIR1-7), or class-IV (HDAC11) HDAC. The second HDAC inhibitor can be an inhibitor of more than more HDACs or more than one classes of HDACs (i.e., non-specific).

For example, the second HDAC inhibitors include but are not limited to vorinostat (SAHA), panobinostat (LBH589), belinostat (PXD101, CAS 414864-00-9), 4-(dimethyl-amino)-N-[6-(hydroxyamino)-6-oxohexyl]-benzamide (HDAC1 inhibitor), 4-Iodo suberoylanilide hydroxamic acid (HDAC1 and HDAC6 inhibitor), romidepsin (a cyclic tetrapeptide with HDAC inhibitory activity primarily towards class-I HDACs), 1-naphthohydroxamic acid (HDAC1 and HDAC6 inhibitor), HDAC inhibitors based on amino-ben-zamide biasing elements (e.g., mocetinostat (MGCD103) and entinostat (MS275), which are highly selective for HDAC1, 2 and 3), AN-9 (CAS 122110-53-6), APHA Compound 8 (CAS 676599-90-9), apicidin (CAS 183506-66-3), BML-210 (CAS 537034-17-6), salermide (CAS 1105698-15-4), suberoyl bis-hydroxamic Acid (CAS 38937-66-5) (HDAC1 and HDAC3 inhibitor), butyrylhydroxamic acid (CAS 4312-91-8), CAY10603 (CAS 1045792-66-2) (HDAC6 inhibitor), CBHA (CAS 174664-65-4), CI 994 (CAS 112522-64-2), JNJ-26481585 (CAS 875320-29-9), ACY1215, trichostatin-A, WT161, tubacin, rocilinostat, and Merck60.

In some embodiments, a compound of the invention is administered in combination with a selective HDAC6 inhibitor, e.g., tubacin or ACY-1215. See, e.g., Hideshirma et al. *Proc Natl Acad Sci USA* 2005. 102:8567-8572; and Santo et al. *Blood* 2012. 119:2579-2589.

In some embodiments, a compound of the invention is administered in combination with an inhibitor of class-I HDAC. In some embodiments, a compound of the invention is administered in combination with a selective HDAC3 inhibitor.

In some embodiments, a compound of the invention is administered in combination with a nucleotide based or protein/peptide based inhibitor of an HDAC.

For example, nucleotide based inhibitors of an HDAC can include but are not limited to short hairpin RNA (shRNA), RNA interference (RNAi), short interfering RNA (siRNA), microRNA (miRNA), locked nucleic acids (LNA), DNA, peptide-nucleic acids (PNA), morpholinos, and aptamers. In some embodiments, nucleotide based inhibitors are composed of at least one modified base. In some embodiments, nucleotide based inhibitors bind to the mRNA of a HDAC and decrease or inhibit its translation, or increase its degradation. In some embodiments, nucleotide based inhibitors decrease the expression (e.g., at the mRNA transcript and/or protein level) of a HDAC in cells and/or in a subject. In some embodiments, nucleotide based inhibitors bind to a HDAC decrease its enzymatic activity.

Protein or peptide based inhibitors of a HDAC can include but are not limited to peptides, recombinant proteins, and antibodies or fragments thereof. Protein or peptide based inhibitors can be composed of at least one non-natural amino acid. In some embodiments protein or peptide based inhibitors decrease the expression (e.g., at the mRNA transcript and/or protein level) of a HDAC in cells and/or in a subject. In some embodiments, protein or peptide based inhibitors bind to a HDAC and decrease its enzymatic activity.

Methods for identifying and/or generating nucleotide based or protein/peptide based inhibitors for a protein described herein are commonly known in the art.

In some embodiments, a compound of the present invention is administered in combination with an ER stressor, e.g., an HSP90 inhibitor. Exemplary HSP90 inhibitors include but are not limited to 17-AAG (17-Demethoxy-17-(2-pro-penylamino) ge-ldanamycin), BIIB 021 (6-Chloro-9-[(4-methoxy-3,5-dimethyl-2-pyridinyl)methyl]-9H-purin-2-amine), CCT 018159 (4-[(4-(2,3-Dihydro-1,4-benzodioxin-6-yl)-5-methyl-1H-pyrazol-3-yl]-6-ethyl-1,3-benzene-diol), 17-DMAG hydrochloride (17-Demethoxy-17-[[2-(dimeth-ylamino)-ethyl]amino]geldanamycin hydrochloride), Gedunin ((1S,3aS,4aR,4bS,5R,6aR,10aR,10bR,12-aS)-5-(Acetyloxy)-1-(3-furanyl)-1,5,6,6a,7,10a,10b-,11,12,12a, decahydro-4b,7,7,10a,12a, pentamethylox-ireno[c]phenan-thro[1,2-d]pyran-3,8(3H,4H)-dione), Geldanamycin (9,13-Dihydroxy-8,14,19-trimethoxy-4-,10,12,16-tetramethyl-2-azabicyclo[16.3.1]docosa-4-,6,10,18,21-pentaene-3,20,22-trione, 9-carbamate), Herbimycin A ((15R)-17-demethoxy-15-methoxy-11-O-methyl-geldanamycin), Macbecin I ((15R)-6,17-Didemethoxy-15-methoxy-6-methyl-11-O-methyl-geldanamycin), PU H71 (6-Amino-8-[(6-iodo-1,3-benzodioxol-5-yl)thio]-N-(1-methylethyl)-9H-purine-9-propanami-ne), and Radicicol ((1aR,2Z,4E,14R,15aR)-8-Chloro-1a,14-,15,15a-tetrahydro-9,11-dihydroxy-14-methyl-6H-oxi-reno[e][2]benzoxacyclotetradecin-6,12 (7H)-dione).

In some embodiments, a compound of the present invention is administered in combination with a caspase inhibitor, e.g., Z-VAD-FMK, Ac-IETD-CHO, LEHD-CHO.

In some embodiments a compound of the invention is administered in combination with one or more, two or more, three or more, four or more, or greater, of an HDAC inhibitor, a proteasomal inhibitor, a deubiquitinase inhibitor, a demethylase inhibitor, an endoplasmic reticulum (ER) stressor (e.g., HSP90 inhibitor), a JNK inhibitor, and a caspase inhibitor.

A multiple myeloma (MM) is a type of cancer formed by malignant plasma cells, which are cells that are found in the bone marrow. Plasma cells that have dysregulated growth can form a tumor in bone. If there is only one plasma cell tumor, the type of cancer is an isolated (or solitary) plasmacytoma. A MM occurs when there is more than one plasma cell tumor. In a MM, abnormal plasma cells accumulate in the bone marrow where they interfere with the production of normal blood cells. Instead of making normal antibodies as normal plasma cells do, MM cells make many copies of the same antibody.

Some symptoms of MM include kidney problems, bone lesions, low blood counts, and hypercalcemia (high calcium levels). For example, low red blood cells (anemia) can manifest as weakness, pale skin, not being able to exercise, shortness of breath, or dizziness. Low white blood cells can manifest as a weaker ability to fight infections, and low platelet count can manifest as heavy bleeding from minor scrapes or cuts, or easy bruising. Bone dissolution due to MM can lead to high levels of calcium in the blood, which can lead to kidney problems. High calcium levels can also cause symptoms like thirst, frequent urination, loss of appetite, constipation, stomach pain, drowsiness and confusion. MM can cause damage to the kidneys, which can manifest as a difficulty for the body to get rid of excess salt, fluid, and body waste products. For example, subjects with kidney damage can feel weak and have shortness of breath, itching, and leg swelling.

Laboratory tests for MM include a determination of blood count. The complete blood count (CBC) is a test that measures the levels of red cells, white cells, and platelets in the blood. If myeloma cells take up too much of the bone marrow, some of these blood levels will be low. The most common finding in MM is a low red blood cell count (anemia). MM can also be detected by measuring the level of immunoglobulins. In MM, the level of one type of immunoglobulin may be high while the others are low. In addition, MM can be detected using SPEP (serum protein electrophoresis), which examines different proteins in the blood to detect any abnormal myeloma proteins. For example, the level of the beta-2 microglobulin protein is commonly elevated in MM. In addition, MM can be detected by the present of abnormal levels of electrolytes (e.g., calcium, potassium, and sodium) in the blood or the presence of myeloma protein in the urine. Also, bone marrow biopsy can be performed to determine the plasma cell count in the bone marrow. Subjects suffering from MM often have higher levels of plasma cells in their bone marrow. In addition, other biopsy tests can be performed to extract tissue from a tumor or lymph node to check for abnormal areas.

In addition to laboratory tests, imaging tests can also be performed to diagnose MM. For example, bone damage caused by the myeloma cells can be seen with x-rays, CT scans, MRI (magnetic resonance imaging), or PET (positron emission tomography) scans. For example, in PET scans, a radioactive labeled sugar (e.g., glucose) is injected into the subject. Since cancer cells absorb high amounts of sugar, areas of radioactivity can indicate cancer.

As used herein, a "subject in need thereof" is a subject having a cell proliferative disorder, or a subject having an increased risk of developing a cell proliferative disorder relative to the population at large. A subject in need thereof can have a precancerous condition. Preferably, a subject in need thereof has cancer. A "subject" includes a mammal. The mammal can be e.g., any mammal, e.g., a human, primate, bird, mouse, rat, fowl, dog, eat, cow, horse, goat, camel, sheep or a pig. Preferably, the mammal is a human.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the invention encompass a variety of conditions wherein cell division is deregulated. Exemplary cell proliferative disorder include, but are not limited to, neoplasms, benign tumors, malignant tumors, precancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. Preferably, the methods provided herein are used to treat or alleviate a symptom of cancer. Preferably, a hematological cell proliferative is hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through die use of appropriate molecular markers.

A "cell proliferative disorder of the hematologic system" is a cell proliferative disorder involving ceils of the hematologic system. A cell proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. Preferably, compounds and/or pharmaceutical compositions of the present invention may be used to treat a cancer selected from the group consisting of a hematologic cancer of the present invention or a hematologic cell proliferative disorder of the present invention.

A hematologic cancer of the present invention can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphoblastic leukemia, acute lymphocytic leukemia, acute myelocytic leukemia, acute myeloid leukemia, chronic lymphocytic leukemia, chronic myelocytic leukemia, chronic myelogenous leukemia, and mast cell leukemia), lymphoid neoplasm, myeloid neoplasms, AIDS-related lymphoma, mast cell neoplasms.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4e, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (1−), PN0 (I+). PN0 (mol−), PN0 (mol+), PN1, PN1(mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, diploid, tetraploid, or as having an altered ploidy. A cancer that is to be treated can be classified as having a chromosomal trans location, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result, in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably; the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention, or a pharmaceutically acceptable salt, ester, solvate, or prodrug. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation, of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt, ester, solvate, or prodrug thereof. Preferably, the mortality rate is decreased by more than 2%: more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more prefer-ably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA*. 100(5):2674-8, 2003. In an aspect, cell death occurs by apoptosis.

As used herein, "treating" or "treat" describes the management and care of a patient for the purpose of combating a disease, condition, or disorder and includes the administration of a compound of the present invention, or a pharmaceutically acceptable salt, ester, solvate, or prodrug thereof to alleviate the symptoms or complications of a disease, condition or disorder, or to eliminate the disease, condition or disorder.

As used herein, the term "alleviate" is meant to describe a process by which the severity of a sign or symptom of a disorder is decreased, importantly, a sign or symptom can be alleviated without being eliminated, in a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

A compound of the present invention, or a pharmaceutically acceptable salt, ester, solvate, or prodrug thereof, can also be used to prevent a disease, condition or disorder. As used herein, "preventing" or "prevent" describes reducing or eliminating the onset of the symptoms or complications of the disease, condition or disorder.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the international Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods. Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type. Furthermore, severity describes a nuclear grade, which refers to the size and shape of the nucleus in tumor cells and the percentage of tumor cells that are dividing.

In another aspect of the invention, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

A cancer may cause symptoms such as fever, fatigue, or weight loss. This may be because cancer cells use up much of the body's energy supply or release substances that change the body's metabolism. Or the cancer may cause the immune system to react in ways that produce these symptoms.

Fever is very common with cancer, but is more often seen in advanced disease. Almost, ail patients with cancer will have fever at some time, especially if the cancer or its treatment affects the immune system and makes it harder for the body to fight infection. Less often, fever may be an early sign of cancer, such as with leukemia or lymphoma.

Fatigue may be an important symptom as cancer progresses. It may happen early, though, in cancers such as with leukemia, or if the cancer is causing an ongoing loss of blood, as in some colon or stomach cancers.

Cancer presents several general signs or symptoms that occur when a variety of subtypes of cancer cells are present. Most people with cancer will lose weight at some time with their disease.

Pain may be an early symptom with some cancers such as bone cancers or testicular cancer. But most often pain is a symptom of advanced disease.

Sometimes, cancer cells release substances into the bloodstream that cause symptoms not usually thought to result from cancers. Some lung cancers make hormone-like substances that, affect blood calcium levels, affecting nerves and muscles and causing weakness and dizziness Along with cancers of the skin (see next section), some internal cancers can cause skin signs that can be seen. These changes include the skin looking darker (hyperpigmentation), yellow (jaundice), or red (erythema); itching; or excessive hair growth.

While the signs and symptoms listed above are the more common ones seen with cancer, there are many others that are less common and are not listed here. However, all art-recognized signs and symptoms of cancer are contemplated and encompassed by the instant invention.

As used herein, a "normal cell" is a cell that cannot be classified as part of a "cell proliferative disorder". A normal cell lacks unregulated or abnormal, growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the present invention, or a pharmaceutically acceptable salt, ester, solvate, or prodrug thereof that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the present invention, or a pharmaceutically acceptable salt, eseter, solvate, or prodrug thereof. The biological or medical response can be the treatment of cancer. The biological or medical response can be treatment or prevention of a cell proliferative disorder. In vitro or in vivo biological assays can include, but are not limited to, enzymatic activity assays, electrophoretic mobility shift assays, reporter gene assays, in vitro cell viability assays, and the assays described herein.

As used herein, "monotherapy" refers to the administration of a single active or therapeutic compound to a subject in need thereof. Preferably, monotherapy will involve administration of a therapeutically effective amount of an active compound. For example, cancer monotherapy with one of the compound of the present invention, or a pharmaceutically acceptable salt, ester, solvate, or prodrug thereof to a subject in need of treatment of cancer. Monotherapy may be contrasted with combination therapy, in which a combination of multiple active compounds is administered, preferably with each component of fee combination present in a therapeutically effective amount. In one aspect, monotherapy with a compound of the present invention, or a pharmaceutically acceptable salt, ester, solvate, or prodrug thereof, is more effective than combination therapy in inducing a desired biological effect.

As used herein, "combination therapy" or "co-therapy" includes the administration of a compound of the present invention, or a pharmaceutically acceptable salt, ester, solvate, or prodrug thereof and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A compound of the present invention, or a pharmaceutically acceptable salt, ester, solvate, or prodrug thereof, may be administered in combination with a second chemo therapeutic agent. The second chemotherapeutic agent (also referred to as an anti-neoplastic agent or anti-proliferative agent) can be an alkylating agent: an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracyeline, a microtubule targeting drug, a topoisomerase poison drug, an inhibitor of a molecular target or enzyme (e.g., a kinase inhibitor), a cytidine analogue drug or any chemotherapeutic, anti-neoplastic or anti-proliferative agent listed in www.cancer.org/docroot/cdg/cdg_0.asp.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); eladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodine[131] tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary MTOR inhibitors include, but are not limited to, everolimus (Afinitor) or temsirolimus (Torisel); rapamune, ridaforolimus; or AP23573.

Exemplary multi-kinase inhibitors include, but are not limited to, sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; seliciclib (CYC202; Roscovitrine); SNS-032 (BMS-387032); Pkc412; bryostatin; KAI-9803; SF1126; VX-680; Azd1152; Arry-142886 (AZD-6244); SCIO-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vineristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacarine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexalen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur –0.4 M 5-chloro-2,4-dihydroxypyrimidine –1 M potassium oxonate) or lovastatin.

In another aspect, the second chemotherapeutic agent can be a cytokine such as G-CSF (granulocyte colony stimulating factor). In another aspect, a compound of the present invention, or a pharmaceutically acceptable salt, ester, solvate, or prodrug thereof, may be administered in combination with radiation therapy. Radiation therapy can also be administered in combination with a compound of the present invention and another chemotherapeutic agent described herein as part of a multiple agent therapy. In yet another aspect, a compound of the present invention, or a pharmaceutically acceptable salt, ester, solvate, or prodrug thereof, may be administered in combination with standard chemotherapy combinations such as, but not restricted to, CMF (cyclophosphamide, methotrexate and 5-fluorouracil), CAF (cyclophosphamide, adriamycin and 5-fluoroufacil), AC (adriamycin and cyclophosphamide), FEC (5-fluorouracil, epirubicin, and cyclophosphamide), ACT or ATC (adriamycin, cyclophosphamide, and paclitaxel), rituximab, Xeloda (capecitabine), Cisplatin (CDDP), Carboplatin, TS-1 (tegafur, gimestat and otastat potassium at a molar ratio of 1:0.4:1), Camptothecin-11 (CPT-11, Irinotecan or Camptosar™) or CMFP (cyclophosphamide, methotrexate, 5-fluorouracil and prednisone).

Exemplary kinase inhibitors include, but are not limited to, Bevacizumab (targets VEGF), BIBW 2992 (targets EGFR and Erb2), Cetuximab/Erbitux (targets Erb1), Imatinib/Gleevic (targets Bcr-Ab1), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Ab1), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PK1-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), sorafenib/Nexavar (targets RAF kinase, VEGFR-1, VEGFR-2, VEGFR-3, PDGFR-β, KIT, FLT-3, and RET), Dasatnib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including Flt3).

Exemplary serine/threonine kinase inhibitors include, but are not limited to, Rapamune (targets mTOR/FRAP1), Deforolimus (targets mTOR), Certican/Everolimus (targets mTOR/FRAP1), AP23573 (targets mTOR/FRAP1), Eril/Fasudil hydrochloride (targets RHO), Flavopiridol (targets CDK), Seliciclib/CYC202/Roseovitrine (targets CDK), SNS-032/BMS-387032 (targets CDK). Ruboxistaurin (targets PKC), Pkc412 (targets PKC), Bryostatin (targets PKC), KAI-9803 (targets PKC), SF1126 (targets PI3K), VX-680 (targets Aurora kinase), Azd1152 (targets Aurora kinase), Arry-142886/AZD-6244 (targets MAP/MEK), SCIO-469

(targets MAP/MEK), GW681323 (targets MAP/MEK), CC-401 (targets JNK), CEP-1347 (targets JNK), and PD 332991 (targets CDK).

As used herein, the term "selectively" means tending to occur at a higher frequency in one population than in another population. The compared populations can be cell populations. Preferably, a compound of the present invention, or a pharmaceutically acceptable salt, ester, solvate, or prodrug thereof, acts selectively on a cancer or precancerous cell but not on a normal cell. Preferably, a compound of the present invention, or a pharmaceutically acceptable salt, ester, solvate, or prodrug, acts selectively to modulate one molecular target (e.g., a target deacetylase) but does not significantly modulate another molecular target (e.g., a non-target deacetylase). Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

The invention also provides a method for selectively inhibiting the activity of an enzyme, such as a histone deacetylase, by contacting a cell having the enzyme with a compound of the present invention.

A compound of the present invention, or a pharmaceutically acceptable salt, ester, solvate, or prodrug thereof, can modulate the activity of a molecular target (e.g., a histone deacetylase). Modulating refers to stimulating or inhibiting an activity of a molecular target. Preferably, a compound of the present invention, or a pharmaceutically acceptable salt, ester, solvate, or prodrug thereof, modulates the activity of a molecular target if it stimulates or inhibits the activity of the molecular target by at least 2-fold relative to the activity of the molecular target under the same conditions but lacking only the presence of said compound. More preferably, a compound of the present invention, or a pharmaceutically acceptable salt, ester, solvate, or prodrug thereof, modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

A compound of the present invention, or a pharmaceutically acceptable salt, ester, solvate, or prodrug thereof, does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" or "isozyme specific" means preferential inhibition or stimulation of a first isoform of an enzyme in comparison to a second isoform of an enzyme (e.g., preferential inhibition or stimulation of a deacetylase isozyme alpha in comparison to a deacetylase isozyme beta). Preferably, a compound of the present invention, or a pharmaceutically acceptable salt, ester, solvate, or prodrug thereof demonstrates a minimum of a four fold differential, preferably a ten fold differential, more preferably a fifty fold differential, in the dosage required to achieve a biological effect. Preferably, a compound of the present invention, or a pharmaceutically acceptable salt, ester, solvate, or prodrug thereof, demonstrates this differential across the range of inhibition, and the differential is exemplified at the $IC_{50}$, i.e., a 50% inhibition, for a molecular target of interest.

Administering a compound of the present, invention, or a pharmaceutically acceptable salt, ester, solvate, or prodrug thereof, to a cell or a subject in need thereof can result in modulation (i.e., stimulation or inhibition) of an activity of an enzyme (e.g., deacetylase) of interest.

The present invention provides methods to assess biological activity of a compound of the present invention, or a pharmaceutically acceptable salt, ester, solvate, or prodrug thereof. In one method, an assay based on enzymatic activity can be utilized. In one specific enzymatic activity assay, the enzymatic activity is from a deacetylase.

A change in enzymatic activity caused by a compound of the present invention, or a pharmaceutically acceptable salt, ester, solvate, or prodrug thereof, can be measured in the disclosed assays. The change in enzymatic activity can be characterized by the change in the extent of phosphorylation of certain substrates. The substrate can be a peptide or protein.

In some assays, immunological reagents, e.g., antibodies and antigens, are employed. Fluorescence can be utilized in the measurement of enzymatic activity in some assays. As used herein, "fluorescence" refers to a process through which a molecule emits a photon as a result of absorbing an incoming photon of higher energy by the same molecule. Specific methods for assessing the biological activity of the disclosed compounds are described in the examples.

Preferably, an effective amount of a compound of the present, invention, or a pharmaceutically acceptable salt, ester, solvate, or prodrug thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a compound of the present invention, or a pharmaceutically acceptable salt, ester, solvate, or prodrug thereof, can induce or activate cell death selectively in cancer cells. Administering to a subject in need thereof a compound of the present invention, or a pharmaceutically acceptable salt, ester, solvate, or prodrug thereof, can induce or activate cell death selectively in cancer cells. Contacting a cell with a compound of the present invention, or a pharmaceutically acceptable salt, ester, solvate, or prodrug thereof, can induce cell death selectively in one or more cells affected by a cell proliferative disorder. Preferably, administering to a subject in need thereof a compound of the present invention, or a pharmaceutically acceptable salt, ester, solvate, or prodrug thereof, induces cell death selectively in one or more cells affected by a cell proliferative disorder.

The present invention relates to a method of treating or preventing cancer by administering a compound of the present invention, or a pharmaceutically acceptable salt, ester, solvate, or prodrug thereof, to a subject in need thereof, where administration of the compound of the present invention, or a pharmaceutically acceptable salt, ester, solvate, or prodrug thereof, results in one or more of the following: accumulation of cells in G1 and/or S phase of the cell cycle, cytotoxicity via cell death in cancer cells without a significant amount of cell death in normal cells, antitumor activity in animals with a therapeutic index of at least 2, and activation of a cell cycle checkpoint. As used herein, "therapeutic index" is the maximum tolerated dose divided by the efficacious dose.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3$^{rd}$ edition). Cold Spring Harbor Press, Cold Spring Harbor, N.Y. (2000); Coligan et al, *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), Remington's *Pharmaceutical Sciences*, Mack Publishing Co., Easton, Pa., 18$^{th}$ edition (1990). These texts can, of course, also be referred to in making or using an aspect of the invention.

4. Pharmaceutical Compositions

The present invention also provides pharmaceutical compositions comprising a compound of each of the formulae described herein in combination with at least one pharmaceutical acceptable excipient or carrier.

A "pharmaceutical composition" is a formulation containing the compounds of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for die adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not as high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitor effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilzing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders tor the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound, can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature; a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in m², and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment, has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, argimine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., an acetate, propionate or other ester.

The compounds of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p1-92, Elesevier, New York-Oxford (1985).

The compounds, or pharmaceutically acceptable salts, esters or prodrugs thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Techniques for formulation and administration of the disclosed compounds of the invention can be found in *Remington: the Science and Practice of Pharmacy*, 19th edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

5. EXAMPLES

Example 1: Experimental Methods

Various methods known in the art can be used for carrying out the present invention. Without limiting the present invention, several experimental methods are described below.

Reagents

HDAC inhibitors LBH589 (panobinostat), MS275 (entinostat), and tubastatin-A were purchased from Selleck Chemicals (Houston, Tex.). Bortezomib was also obtained from Selleck Chemicals. Compound 10 (N-(2-aminophenyl) pyrazine-2-carboxamide) and Merck60 (4-acetamido-N-(2-amino-5-(thiophen-2-yl)phenyl)benzamide) (see, e.g., Methot et al. Bioorg. Med. Chem. Lett. 2008. 18(3):973-8) were synthesized in house (Massachusetts General Hospital, Cambridge, Mass.). Human recombinant Interleukin (IL)-6 was purchased from R&D Systems (Minneapolis, Minn.).

Cells

RPMI8226 and U266 human MM cell lines, as well as human embryonic kidney 293T cells, were obtained from American Type Culture Collection (ATCC, Manassas, Md.). MM.1S cells were provided by Dr. Steven Rosen (Northwestern University). Interleukin-6 dependent INA-6 cell line was obtained from Dr. Renate Burger (Univ. of Kiel, Kiel, Germany). Melphalan-resistant (LR5) and doxorubicin-resistant (RPMI-DOX40) cells were provided by Dr. William Dalton (Lee Moffitt Cancer Center), OPM1 and OPM2 cells were obtained from Dr. Edward Thompson (University of Texas Medical Branch, Galveston, Tex.). MM cell lines were maintained in RPMI 1640 medium (Sigma-Aldrich) supplemented with 10% fetal bovine serum, 2 mM L-glutamine (Invitrogen), 100 units/mL penicillin, and 100 units/mL streptomycin (Invitrogen). 293T cells were maintained in Dulbecco Modified Eagle Medium (Sigma-Aldich) supplemented with 10% fetal bovine serum, 100 units/mL penicillin, and 100 mg/mL streptomycin (Invitrogen).

BM specimens were obtained from patients with MM, and mononuclear cells (MNCs) were separated by Ficoll-Hipaque density sedimentation. Primary CD138+ plasma cells from MM patients were obtained using negative selection, as in previous studies. See, e.g., Hideshima et al. Blood 2006, 107:4053-4062. CD138-BMMNCs were used to establish long-term BMSC cultures, as previously described. See, e.g., Hideshima et al. Blood 2006, 107:4053-4062. Peripheral blood mononuclear cells were collected from healthy volunteers to obtain mononuclear cells (PBMCs). All procedures were performed with IRB-approved (Dana-Farber Cancer Institute) protocols and informed consent, and in accordance with the Declaration of Helsinki protocol.

Cell Growth Inhibition Assay

The growth inhibitory effects of Merck60, MS275, Compound 10, bortezomib and HDAC3 knockdown in MM cell lines were assessed by measuring 3-(4,5-dimethylthiazol-2-yl)-2,5-diphenyl tetrasodium bromide (MTT; Sigma-Aldrich) dye absorbance. To measure proliferation of MM cells, the rate of DNA synthesis was measured by $^3$[H]-thymidine (Perkin-Elmer) uptake.

Immunoblotting and Immunoprecipitation

MM cells were harvested and lysed using sodium dodecyl sulfate-polyacrylamide gel electrophoresis (SDS-PAGE) sample buffer containing 60 mM Tris-HCl, pH 6.8, 2% SDS, 10% glycerol, 0.005% bromophenol blue, 5 mM ethylenediaminetetraacetic acid, 5 mM NaF, 2 mM $Na_3VO_x$, 1 mM phenylmethylsulfonyl fluoride (PMSF), 5 μg/mL leupeptin, and 5 μg/mL aprotinin; and then heated at 100° C. for 5 min. After the determination of protein concentration using DC protein assay (Bio-Rad, Hercules, Calif.), β-mercaptoethanol (β-ME) was added to the whole-cell lysates to a 2% final β-ME concentration. The whole-cell lysates were subjected to SDS-PAGE, transferred to nitrocellulose membranes (Bio-Rad, Hercules, Calif.) or polyvinylidene fluoride membranes (Millipore, Billerica, Mass.), and immunoblotted with anti-histone H3, -HDAC1, -HDAC2, -HDAC3, -Acetyl-histone H2A (Lysine 5) (Ac-H2AK5), -Acetyl-histone H2B (lysine 5) (Ac-H2 BK5), -Acetyl-histone H3 (lysine 9) (Ac-H3K9), -Acetyl-histone H4 (lysine 8) (Ac-H4K8), -glyceraldehyde-3-phosphate dehydrogenase (GAPDH), -poly (ADP-ribose) polymerase (PARP), -caspase-3, -caspase-8, -caspase-9, -Signal transducers and activators of transcription 3 (STAT3), -phospho-STAT3 (pSTAT3) (tyrosine 705), -pSTAT3 (serine 727), -p21, -Janus kinase 2 (JAK2), -acetylated-Lysine (Ac-K), and anti-phosphorylated-tyrosine antibodies (Abs; Cell Signaling Technology, Beverly, Mass.).

For immunoprecipitation, MM cells were lysed with Nonidet P-40 (NP-40) buffer (50 mM Tris-HCl [pH 7.4], 150 mM NaCl, 1% NP-40, 5 mM ethylenediaminetatraacetic acid, 5 mM NaF, 2 mM $Na_3VO_4$, 1 mM PMSF, 5 μg/mL leupeptin, and 5 μg/mL aprotinin). Whole-cell lysates were incubated with anti-STAT3, -JAK2, and -green fluorescent protein (GFP) Abs for 2 hours at 4° C., and then incubated with Protein A/G PLUS-Agarose® (Santa Cruz Biotechnology) overnight at 4° C. Anti-GFP Ab served as a control. Immune complexes were analyzed by immunoblotting with anti-STAT3, -JAK2, -acetylated-Lysine, and -phosphorylated-tyrosine Abs.

Transfection of Short Hairpin RNA (shRNA)

HDAC1, HDAC2 and HDAC3 pLKO.1 shRNA vectors were obtained from the RNA Interference Screening Facility at the Dana-Farber Cancer institute. Recombinant lentivirus was produced and infection of MM cells was performed using standard methods in the art.

Murine Xenograft Models

CB17 SCID mice (48-54 days old) were purchased from Charles River Laboratories (Wilmington, Mass.). All animal studies were conducted according to protocols approved by the Animal Ethics Committee of the Dana-Farber Cancer Institute. After irradiation (200cGy), mice were subcutaneously injected with 5×10⁶ MM.1S cells in the right flank. Compound 10 and bortezomib were dissolved in 10% Dimethylacetamide (DMSA; Sigma-Aldrich) in 10% Kolliphor® HS15 (Sigma-Aldrich) in phosphate buffered saline (PBS) and 0.9% saline solution, respectively. When tumors were measurable, mice were treated with intraperitoneal injection (IP) of vehicle control, Compound 10 (15 mg/kg), or Compound 10 (50 mg/kg) 5 days a week for 3 weeks (n=6/group). Additionally, mice were also treated with 50 mg/kg Compound 10 in combination with 0.5 mg/kg (subcutaneous injection) bortezomib twice a week. Tumor size was measured every three days, and tumor volume was calculated with the formula: $V=0.5 (a \times b^2)$, where "a" is the long diameter of the tumor and "b" is the short diameter of the tumor. Mice were sacrificed when the tumor reached 2 cm in length or 2 cm³ volume, or if mice appeared moribund to prevent unnecessary morbidity. Survival was evaluated from the first day of the treatment until death.

Statistical Analysis

The combined effect of drugs was analyzed by isobologram analysis using the Compusyn software program (ComboSyn, Inc.); a combination index (CI)<1 is indicative of a synergistic effect. In the murine xenograft studies, statistical significance was determined by Student t test. The minimal level of significance was p<0.05.

Example 2: Toxicity of MS275 and Merck60 in MM Cells

Non-selective HDAC inhibitors have demonstrated variable anti-MM activity in preclinical studies. The growth inhibitory effect of Merck60 (HDAC1, 2 inhibitor previously reported as compound #60 by Method et al. Bioorg. Med. Chem. Lett. 2008. 18(3):973-8) versus MS275 (HDAC1, 2, 3 inhibitor) was examined in MM cell lines using MTT assay. MM cells were cultured with Merck60 (left panel) or MS275 (right panel) for 48 hours. Cell growth was assessed by MTT assay. All experiments were performed 3 times in quadruplicate. Data represent mean±SD. MS275 triggered significant MM cell growth inhibition, whereas Merck60 induced only a modest growth inhibition effect (FIG. 1A).

Figure 1B:
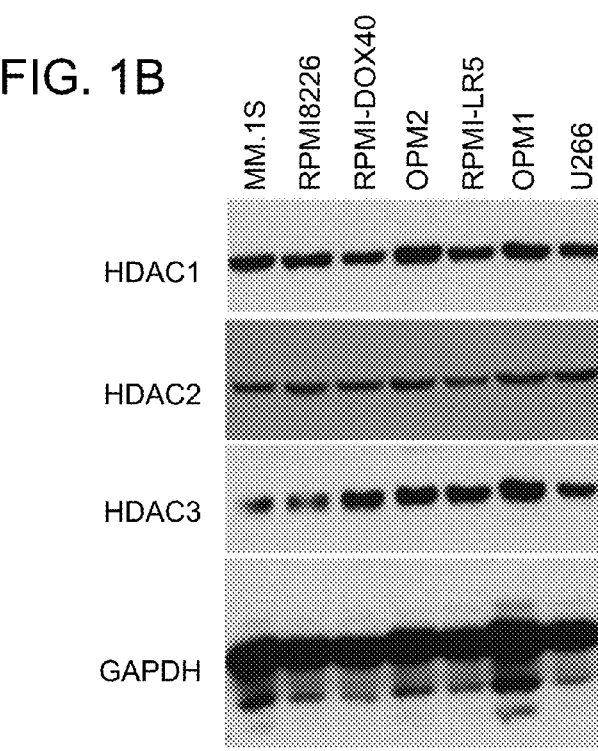
FIG. 1B is a Western blot of whole cell lysates from MM cells lines to determine HDAC1, 2 and 3 expression.

Immunoblotting confirmed that all MM cell lines express HDAC1, 2, and 3 proteins (FIG. 1B). Specifically, whole cell lysates from MM cells lines were subjected to immunoblotting to assess HDAC1, 2 and 3 expression. GAPDH served as a loading control. In addition, the effects of these agents on acetylation of histones in RPMI8226 MM cells were determined. Whole cell lysates from RPMI8226 cells treated with Merck60 or MS275 for 12 h were subjected to immunoblotting with anti-Ac-H2AK5, -Ac-H2 BK5, -Ac-H3K9, -Ac-H4K8, -p21$^{WAF1}$, and -histone H3 antibodies (Abs).

Figure 1C:
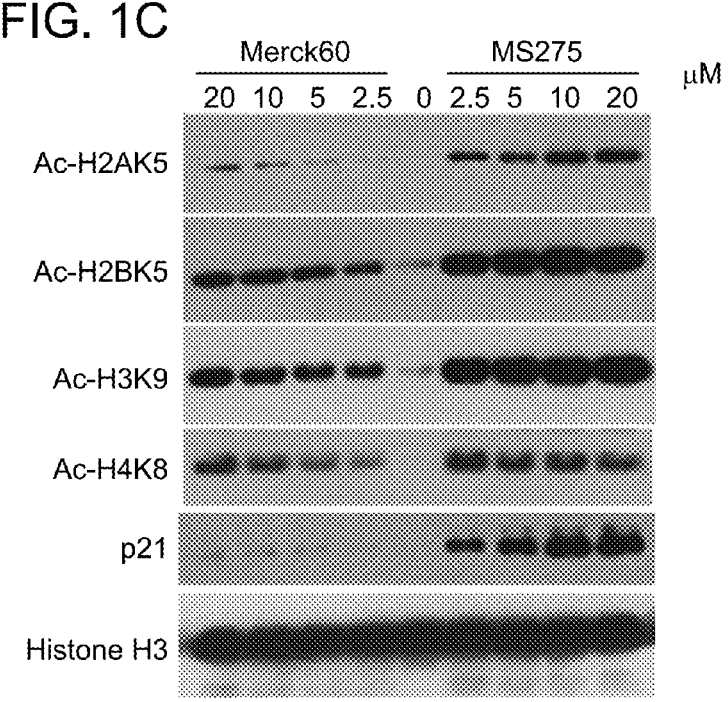
FIG. 1C is a Western blot of whole cell lysates from RPMI8226 cells treated with Merck60 or MS275 for 12 h to determine acetylation of various proteins.

MS275 in a dose-dependent manner more potently induced acetylation of histones (H2A, H2B, H3 and H4) and increased p21WAF1 expression than Merck60 (FIG. 1C). These results show that HDAC3 plays an important role in MM cell growth and/or survival.

Example 3: HDAC3 Knockdown Inhibits MM Cell Growth

Figure 2A:
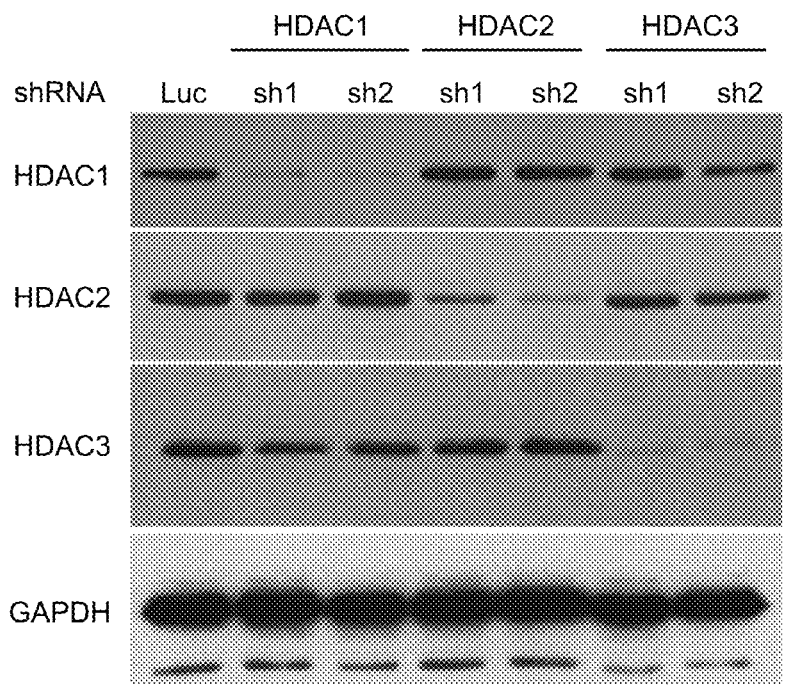
FIG. 2A is a Western blot of whole cell lysates of PMI8226 cells treated with shRNAs to determine HDAC1, 2 and 3 expression.

Experiments were performed to determine whether HDAC3 selective knockdown inhibits MM cell growth. MS275, a HDAC1, 2, and 3 inhibitor, triggered significant MM cell growth inhibition. To determine whether the MM cell growth inhibitory effect of MS275 is predominantly due to HDAC3 inhibition, a knockdown of HDAC isoforms (HDAC 1, 2, and 3) using a lentiviral shRNA infection system was performed. RPMI8226 cells were infected with either luciferase (Luc, as control), HDAC1 (sh1, sh2), HDAC2 (sh1, sh2) or HDAC3 (sh1 or sh2) shRNAs. Isoform-specific HDAC1, 2, or 3 knockdown in RPMI8226 MM cells was confirmed by immunoblotting (FIG. 2A).

Figure 2B:
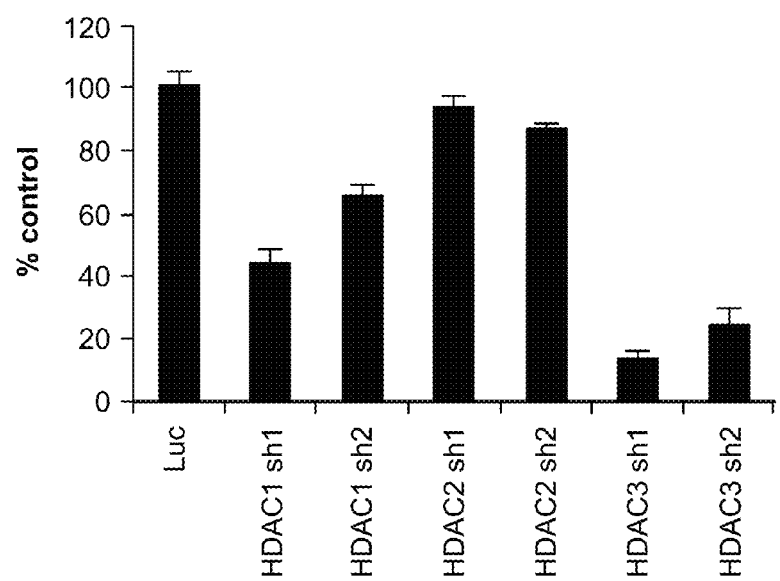
FIG. 2B is a graph showing proliferation of shRNA treated cells by the $^3$[H]-thymidine uptake assay.
Figure 2C:
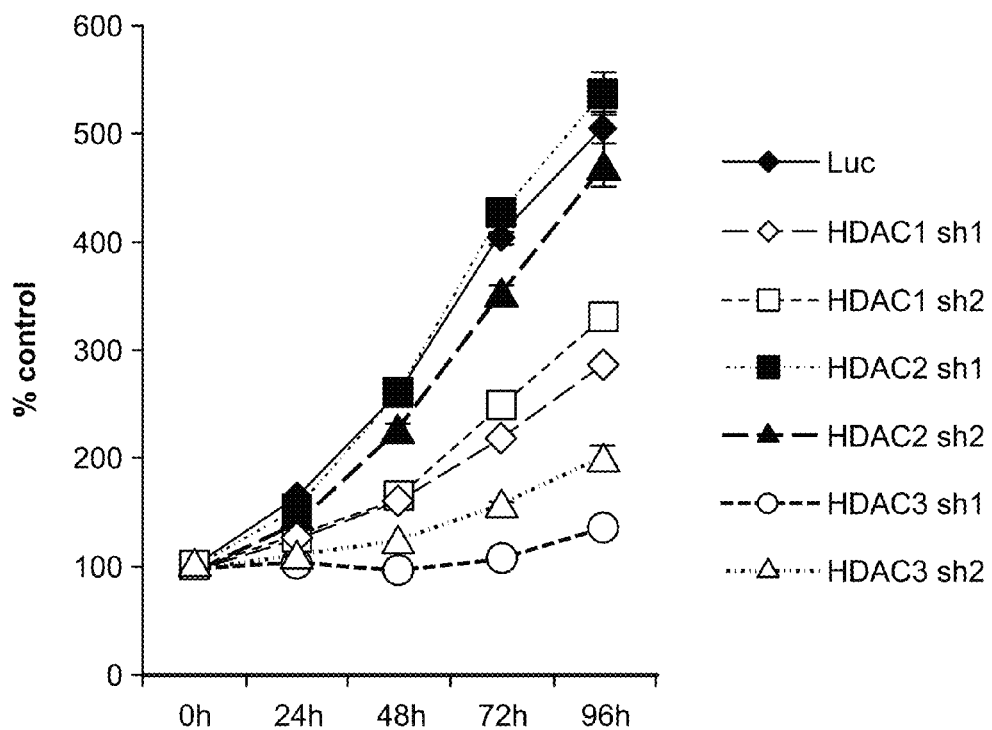
FIG. 2C is a graph showing cell growth of shRNA treated cells by the MTT assay.
Figure 2D:
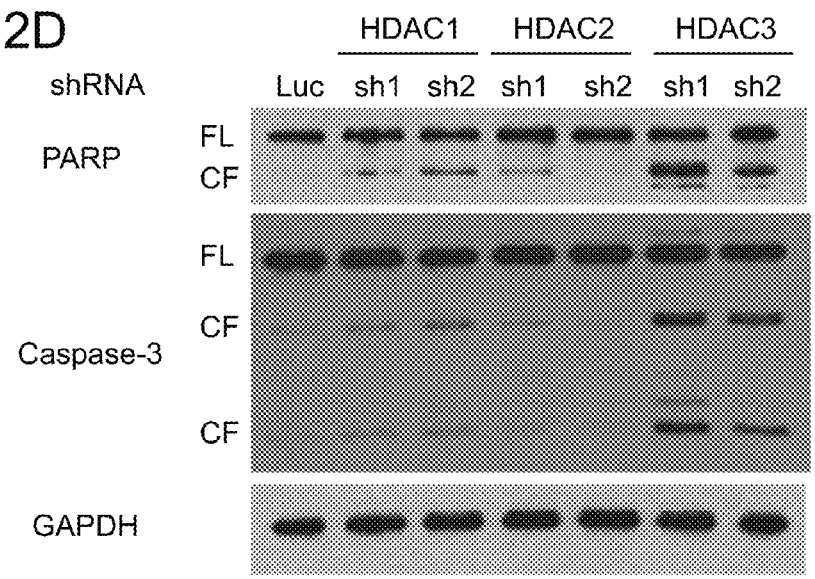
FIG. 2D is a Western blot of whole cell lysates from shRNA treated cells subjected to immunoblotting with anti-caspase-3, -PARP, and -GAPDH antibodies. FL and CF indicate full-length and cleaved form, respectively.
Figure 2F:
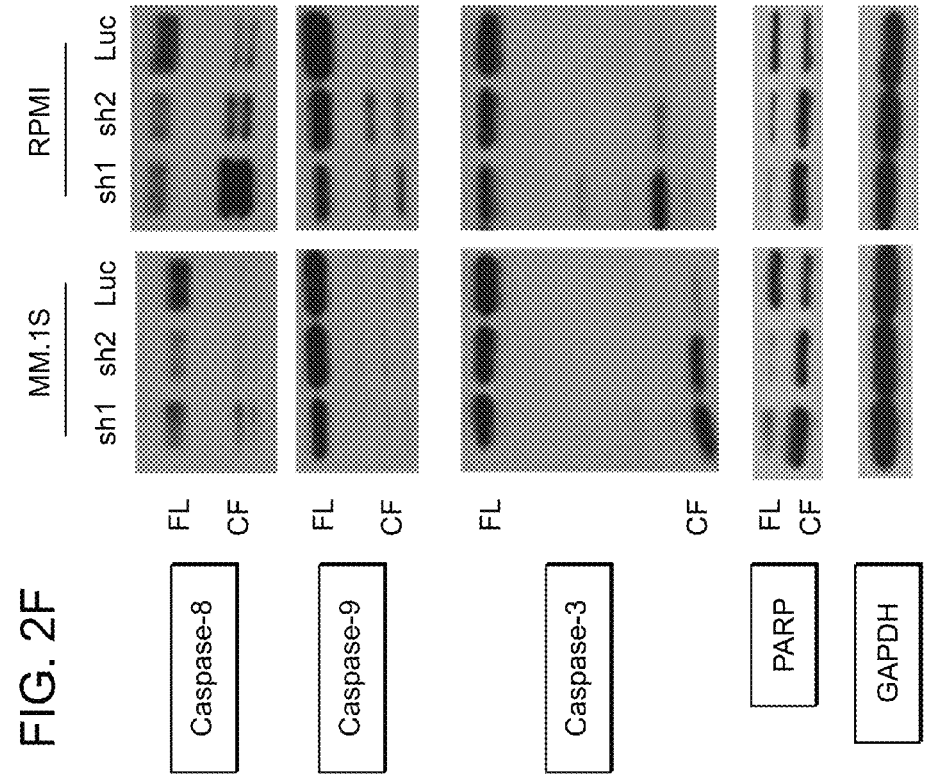
FIG. 2F is a Western blot of whole cell lysates of HDAC3-knockdown cells subjected to immunoblotting by caspase-8, caspase-9, caspase-3, and PARP antibodies.
Figure 2E:
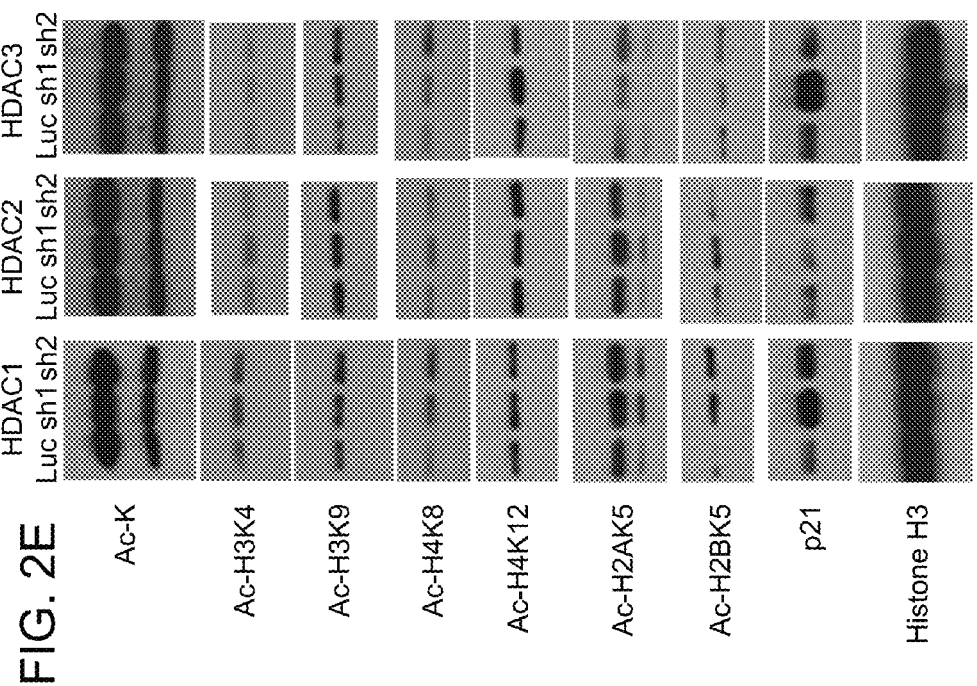
FIG. 2E is a Western blot of whole cell lysates from shRNA treated cells subjected to immunoblotting with anti-Ac-K, -Ac-H3K4, -Ac-H3K9, -Ac-H4K8, -Ac-H4K12, -Ac-H2AK5, -Ac-H2 BK5 and -histone H3 antibodies.

HDAC3 knockdown triggered the most significant growth inhibitory effect in RPMI8226 cells, assessed by both [³H]-thymidine uptake (an assay for DNA synthesis, which reflects cell proliferation rates) (FIG. 2B) and MTT assay (an assay for cell viability and proliferation) (FIG. 2C). In contrast, HDAC1 knockdown induced only modest growth inhibition, and no growth inhibitory effect was observed after HDAC2 knockdown. These findings confirm that HDAC3 plays a crucial role in MM cell growth and survival. The molecular mechanism whereby HDAC3 knockdown triggers MM cell growth inhibition was further examined. HDAC3, but not HDAC1 or 2, knockdown induced caspase-3 and PARP cleavage (FIG. 2D). The effects of HDAC1, HDAC2 or HDAC3 knockdown on acetylation of histones in RPMI8226 cells were also examined. As shown in FIG. 2E, there was no significant difference in the pattern of histone lysine acetylation between isoform-specific HDAC 1, 2 or 3 knockdown cells.

In addition, the effect of HDAC3 knockdown on apoptosis was examined. RPMI8226 and MM.1S cells were infected with either luciferase (Luc, as control), or HDAC3 (sh1 or sh2) lentiviral shRNAs. Western blotting to assess apoptosis was done using caspase-8, -9, -3, and PARP antibodies. Cleavage of caspase-8, caspase-9, and PARP in HDAC3 knockdown cells indicates that HDAC3 knockdown-induced growth inhibition is triggered by apoptosis via both intrinsic and extrinsic apoptotic pathways (FIG. 2F).

Figure 3B:
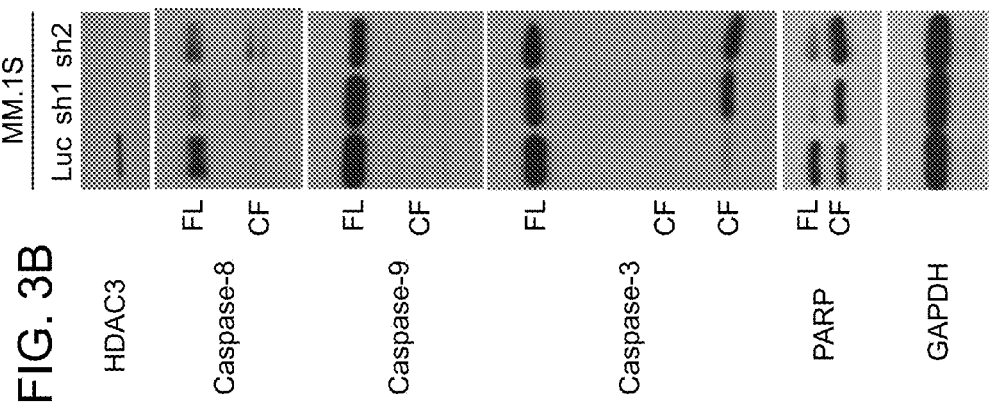
FIG. 3B is a Western blot against caspase-8, -9, -3 and PARP in the shRNA treated cells.
Figure 3A:
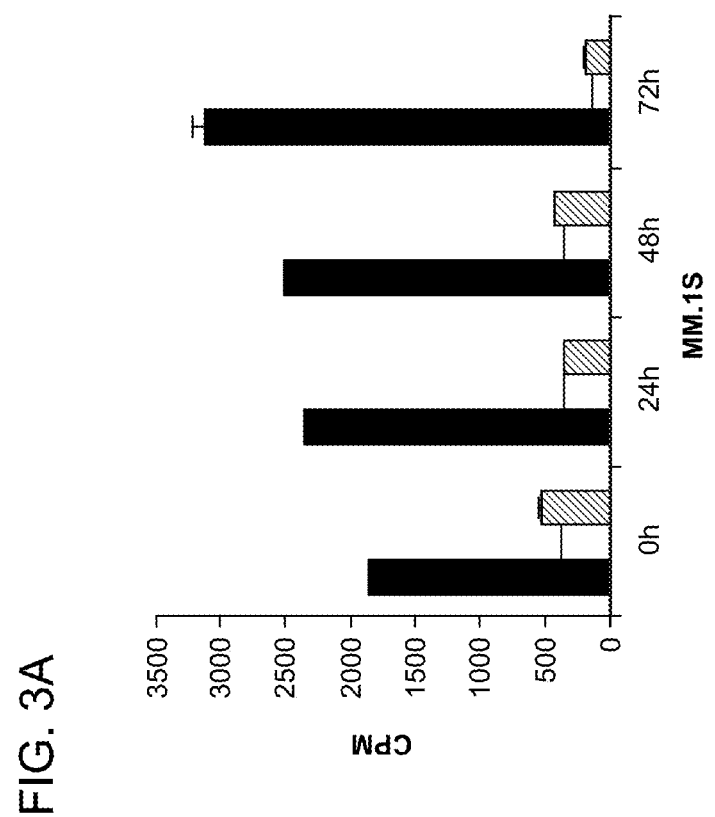
FIG. 3A is a graph depicting the counts per minute (CPM) by the [$^3$H]-thymidine uptake assay of MM.1S cells treated with Luciferase (Luc) control (black bars), or shRNA against HDAC3 (sh1, sh2) (white and gray bars).

Similar results were also observed in MM.1S cells. In particular, experiments were conducted to determine the effect of HDAC3 knockdown in MM.1S cells on their proliferation rate. The proliferation rate was assayed by a ³[H]-thymidine uptake, with a higher CPM indicating greater DNA synthesis (and thus, higher rate of cell proliferation). As shown in FIG. 3A, MM.1S cells knocked down in HDAC3 had a lower cell proliferation rate. Also, the effect of HDAC3 knockdown on apoptosis was examined in MM.1S cells. MM.1S cells were infected with either luciferase (Luc, as control), or HDAC3 (sh1 or sh2) lentiviral shRNAs. Western blotting to assess apoptosis was done using caspase-8, -9, -3, and PARP antibodies. Cleavage of caspase-8, caspase-9, and PARP in HDAC3 knockdown MM.1S cells indicates that HDAC3 knockdown-induced growth inhibition is triggered by apoptosis via both intrinsic and extrinsic apoptotic pathways (FIG. 3B). Taken together, these results show that HDAC3 knockdown induces growth arrest and apoptosis in multiple MM cell types.

Example 4: HDAC3 Modulates JAK/STAT3 Pathway in MM Cells

The BM microenvironment induces MM cell proliferation, survival, drug resistance, and migration. See, e.g., Hideshima et al. Nat. Rev. Cancer. 2002. 2:927-937; and Hideshima et al. Nat. Rev. Cancer. 2007. 7:585-598. The JAK2/STAT3 pathway mediates MM cell survival by regulating anti-apoptotic proteins including Mcl-1, Bcl-xL, and survivin. See, e.g., Nelson et al. Blood 2008, 112:5095-

5102. Therefore, experiments were performed to examine whether the non-selective HDAC inhibitor LBH589 modulated P-STAT3 in MM cells.

Figure 4A:
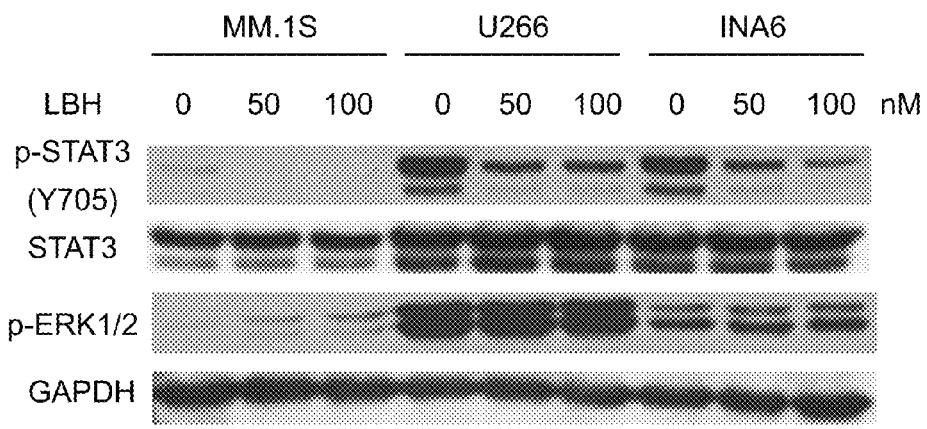
FIG. 4A is a Western blot of whole cell lysates from cells treated with LBH subjected to immunoblotting with anti-STAT3, -pSTAT3 (Tyr705), -pERK1/2, and -GAPDH antibodies.

MM.1S, U266, and INA6 cells were cultured with DMSO control or LBH589 (50 and 100 nM) for 8 h. Whole cell lysates were subjected to immunoblotting with anti-STAT3, -pSTAT3 (Tyr705), -pERK1/2, and -GAPDH Abs. p-STAT3 was significantly inhibited by LBH589 treatment in MM.1S, U266, and INA-6 cells (FIG. 4A).

Figure 4B:
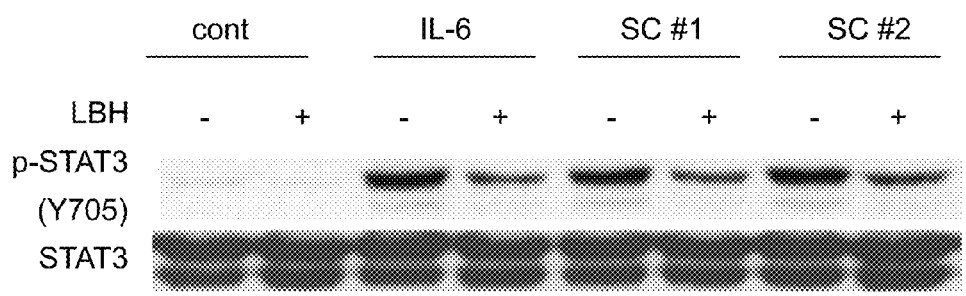
FIG. 4B is a Western blot of whole cell lysates of MM.1S cells treated with 50 nM LBH and then with IL-6 (10 ng/mL) or BMSC culture supernatants (#1 and #2) for 15 minutes subjected to immunoblotting with anti-pSTAT3 (Tyr705) and -STAT3 antibodies.

Since p-STAT3 can be upregulated in the context of the BM microenvironment, experiment were conducted to examine whether inhibition of p-STAT3 by LBH589 treatment of MM.1S cells was maintained even in the presence of exogenous IL-6 or BMSC culture supernatants. MM.1S cells pretreated with or without 50 nM LBH589 for 8 hours were then treated with IL-6 (10 ng/mL) or BMSC culture supernatants (#1 and #2) for 15 minutes. Whole cell lysates were subjected to immunoblotting with anti-pSTAT3 (Tyr705) and STAT3 Abs. Both IL-6 and BMSC culture supernatants markedly upregulated P-STAT3, which was blocked by LBH589 (FIG. 4B).

Figure 4C:
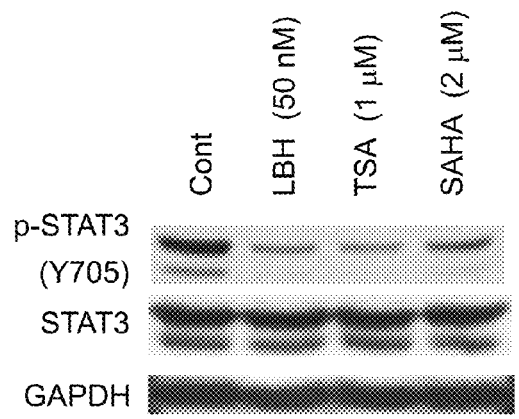
FIG. 4C is a Western blot of whole cell lysates from INA-6 cells treated with various agents subjected to immunoblotting with anti-pSTAT3 (Tyr705), -STAT3, and -GAPDH antibodies.

In addition, INA-6 cells were cultured with DMSO control, LBH589 (50 nM), TSA (1 µM) or SAHA (2 µM) for 8 hours. Whole cell lysates were subjected to immunoblotting with anti-pSTAT3 (Tyr705), STAT3, and GAPDH Abs. Thus, other non-selective HDAC inhibitors (e.g., TSA, SAHA) also downregulated p-STAT3 (FIG. 4C).

Figure 4D:
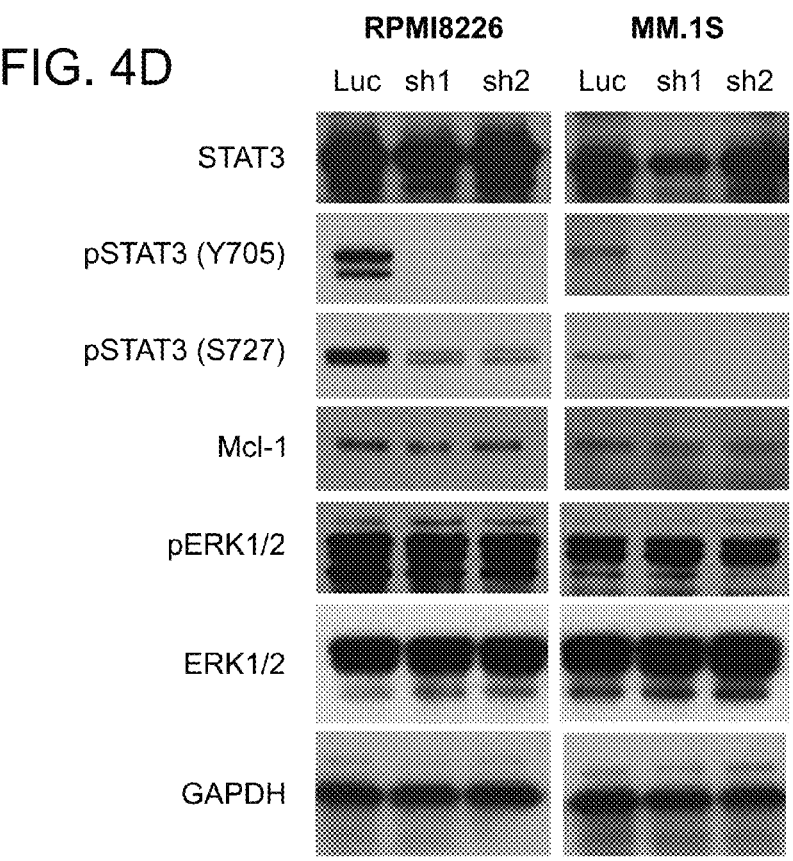
FIG. 4D is a Western blot of whole cell lysates from RPMI8226 and MM.1S cells treated with shRNAs subjected to immunoblottting with anti-STAT3, -pSTAT3 (Tyr705), -pSTAT3 (Ser727), -pERK1/2, -ERK1/2, and -GAPDH antibodies.

To determine whether downregulation of p-STAT3 induced by non-selective HDAC inhibitors is mediated via HDAC3 inhibition, p-STAT3 was examined in HDAC3 knockdown MM cells. RPMI8226 (left panel) and MM.1S (right panel) cells were infected with either Luc or HDAC3 (#1 and #2) shRNAs. Whole cell lysates were subjected to immunoblotting with anti-STAT3, -pSTAT3 (Tyr705), -pSTAT3 (Ser727), -pERK1/2, -ERK1/2, and -GAPDH Abs. Both tyrosine (Y705) and serine (S727) phosphorylation of STAT3 were markedly downregulated in HDAC3 knockdown cells, without inhibition of p-ERK (FIG. 4D).

Figure 4E:
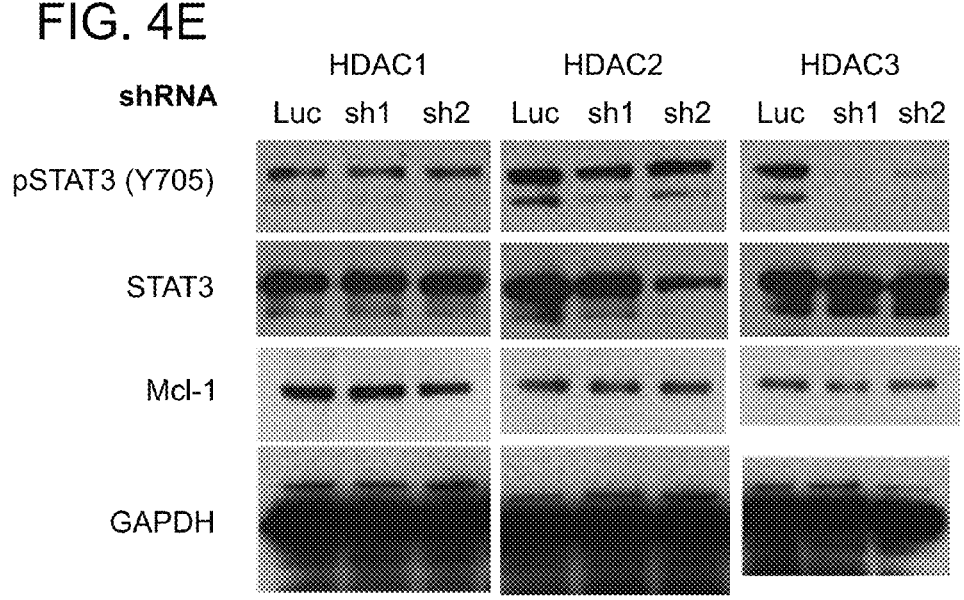
FIG. 4E is a Western blot showing STAT3 phosphorylation in RPMI8226 cells treated with shRNAs.

In addition, RPMI8226 cells were infected with Luc or HDAC1 (#1 and #2), HDAC2 (#1 and #2) or HDAC3 (#1 and #2) shRMAs. W hole cell lysates were subjected to immunoblotting with anti-pSTAT3 (Tyr705), -STAT3 and -GAPDB Abs.No downregulation of p(Y705)-STAT3 was observed in HDAC1 or HDAC2 knockdown cells (FIG. 4E), further confirming that HDAC3 specifically modulates STAT3 phosphorylation in MM cells.

Figure 4F:
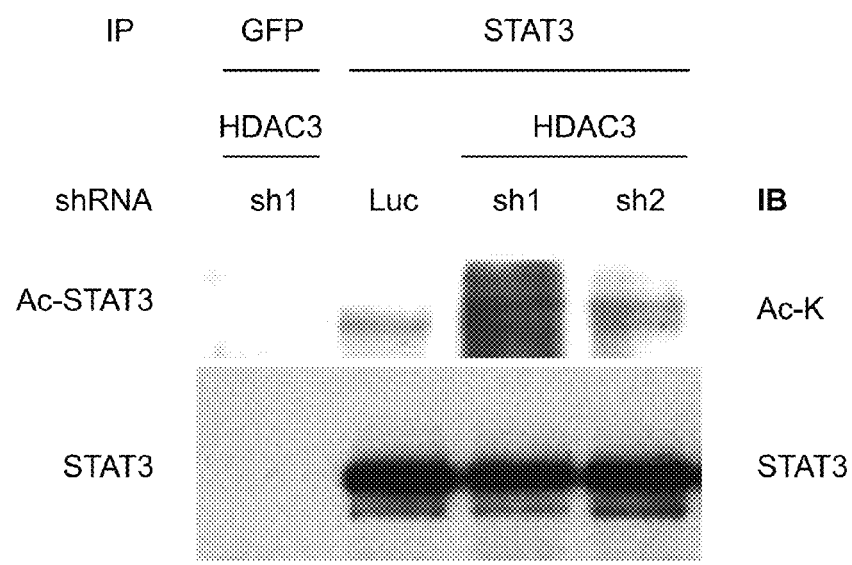
FIG. 4F is a Western blot showing STAT3 acetylation and JAK2 phosphorylation in RPMI8226 celss treated with shRNAs.
Figure 4F:
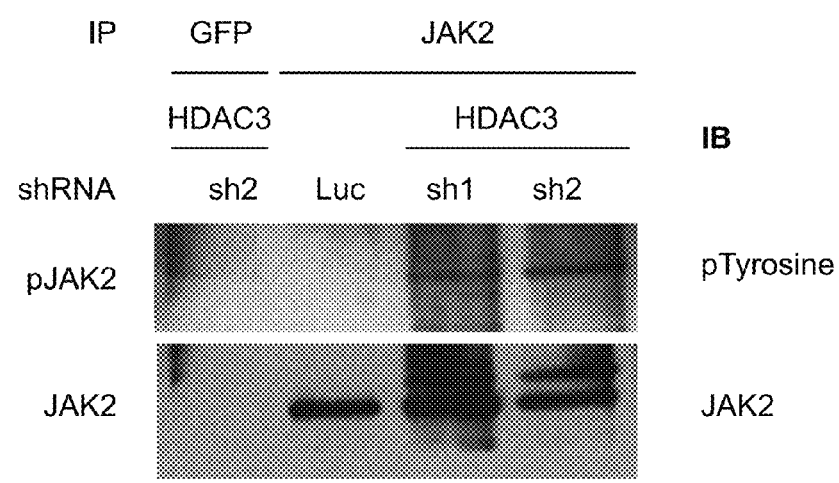

Since STAT3 can be acetylated at lysine 685 (see, e.g., Yuan, et al. Science 2005. 307:269-273), further experiments were conducted to determine whether HDAC3 knockdown affects STAT3 acetylation. RPMI8226 cells were infected with either Luc or HDAC3 (#1 and #2) shRNAs. Whole cell lysates were immunoprecipitated with (FIG. 4F, left panel) anti-GFP or -STAT3 or (FIG. 4F, right panel) -JAK2 Abs. Immunoprecipitates were subjected to SDS-PAGE and immunoblotted with (FIG. 4F, left panel) Ac-lysine and STAT3 or (FIG. 4F, right panel) p-tyrosine and JAK2 Abs. As shown in FIG. 4F (left panel), STAT3 was hyperacetylated in HDAC3 knockdown RPMI8226 cells. In addition, phosphorylation of JAK2, an upstream molecule of STAT3, was upregulated in HDAC3 knockdown cells (FIG. 4F, right panel), suggesting a positive feedback loop associated with downregulated p-STAT3. These results provide evidence that HDAC3 knockdown directly inhibits phosphorylation on both Y705 and S727 of STAT3.

Example 5: Design of HDAC Inhibitors

The design of HDAC inhibitors considers both the sterical requirements and the coordination sphere of the catalytic zinc; this is distinct from other metalloproteases. For hydroxamate based inhibitors, the pKa of the zinc binding group is a critical feature with a significant impact on ligand affinity. The seemingly subtle differences between HDAC enzymes with high structural homology allows for the development of inhibitors with high isoform specificity. To explore and exploit this feature, a set of aminoanilide-derived DAC inhibitors (based on CI-994 and MS-275) were designed and synthesized that explore electron-rich and electron-poor (hetero) aromatic residues in place of the common benzamide-scaffold.

Exemplary inhibitors are shown in Table 1.

Example 6: Inhibitory Activity ($IC_{50}$ Values) of Compounds of the Invention Towards HDAC1, 2, 3, and 6

HDAC inhibitor compounds designed and synthesized in accordance with the present invention were tested for their inhibitor activity against several different HDAC isoforms. The inhibitory activity ($IC_{50}$ values) against HDAC 1, 2, 3, and 6 was determined. The IC50 values are shown in Table 2.

TABLE 2

| DFCI Compound | Compound | HDAC1 [µM] | HDAC2 [µM] | HDAC3 [µM] | HDAC6 [µM] |
| --- | --- | --- | --- | --- | --- |
| BG23 | 1 | 4.495 | 3.849 | 0.5244 | 74.34 |
| BG24 | 2 | 2.82 | 2.336 | 0.3676 | >100 |
| BG25 | 3 | 1.521 | 2.356 | 0.3459 | >100 |
| BG26 | 17 | 1.394 | 1.365 | 0.2126 | >100 |
| BG31 | 5 | 10.48 | 3.666 | 3.32 | >100 |
| BG32 | 6 | 5.766 | 1.912 | 1.987 | >100 |
| BG33 | 7 | 12.43 | 4.106 | 3.623 | >100 |
| BG34 | 8 | 0.7349 | 1.211 | 0.1694 | >100 |
| BG40 | 9 | 3.275 | 2.592 | 0.2799 | >100 |
| BG45 | 10 | 0.922 | 1.489 | 0.1396 | 78.99 |
| BG50 | 11 | <0.01 | 0.06042 | 0.8431 | >100 |
| BG51 | 12 | 1.231 | 0.7601 | 0.07021 | >100 |
| BG52 | 13 | 26.97 | 13.39 | 1.963 | >100 |
| BG53 | 14 | 4.124 | 2.316 | 0.296 | >100 |
| BG54 | 15 | 13.65 | 5.521 | 2.345 | >100 |
| CI-994 | 16 | 0.101 | 0.2695 | 0.0576 | >100 |

Example 7: Synthesis of Compounds of the Invention

Compounds of the invention can be synthesized using the exemplary procedure described below. For example, the small molecule HDAC3 inhibitor Compound 10 (listed as "4" in Scheme 1) was synthesized using the following procedure.

Scheme:1

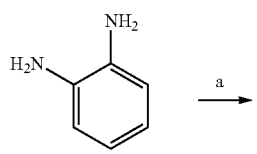

1

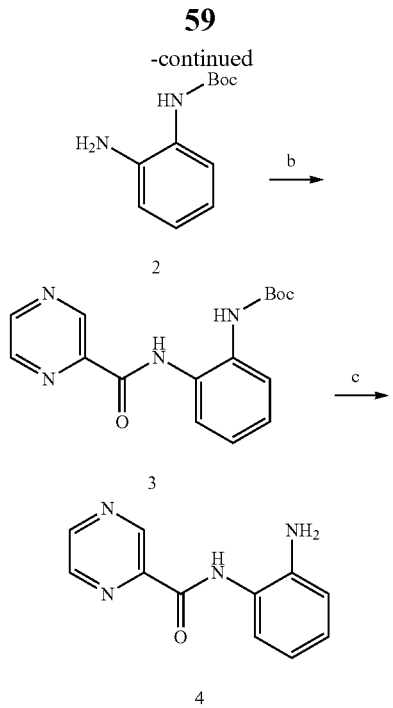

Reagents & conditions: (a) Boc₂O, 4-DMAP, THF, 2 h, RT
(b) pyrazine-2-carboxylic acid, EDCI, 4-DMAP(cat), DCM:pyridine (1:1), RT, 2 h
(c) DCM:THF (1:1), RT, 30 min

Synthesis of tert-butyl (2-aminophenyl)carbamate (2)

To a stirring solution of benzene-1,2-diamine (1.0 g, 9.247 mmol) and 4-dimethylminopyridine (DMAP, 50 mg) in THF (20 mL), a solution of di-tert-butyl dicarbonate (Boc₂O; 1.009 g, 4.6236 mmol) in dichloromethane (20 mL) was added drop wise at room temperature. The reaction mixture was evaporated in a rotary evaporator and purified by column chromatography using hexane and ethylacerate solvent mixture (80:20) to obtain the desired mono-Boc protected compound 2 (0.380 g, 20% yield)

Synthesis of tert-butyl (2-(pyrazine-2-carboxamido)phenyl)carbamate (3)

Compound 3 was synthesized following aromatic acid and aromatic amine coupling reactions, where pyrazine-2-carboxylic acid (0.03 g, 0.242 mmol) was dissolved in dichloromethane/pyridine (1:1) mixture, and EDCI (0.051 g, 0.266 mmol) was added and stirred for 10 min. Tert-butyl (2-aminophenyl)carbamate (0.061 g, 0.29 mmol) and catalytic amounts of 4-DMAP were added at room temperature, and stirring was continued to 2 h. The reaction mixture was evaporated, and crude mixture was resuspended into ethyl acetate and extracted from aqueous NaHCO₃ solution. After evaporating the EtOAc layer, the titled compounds were purified by column chromatography using ethyl acetate methanol (9:1) solvent system to obtain the desired compound 3 (0.024 g, 31.6% yield)

Synthesis of N-(2-aminophenyl)pyrazine-2-carboxamide (4) (Compound 10)

The final compound is made by deprotection of Boc group from tert-butyl (2-(pyrazine-2-carboxamido)phenyl)carbamate using dichloromethane and trifluoroacetic acid (1:1) mixture at room temperature for 30 min, which was then made free base by suspending the crude mixture into aqNaHCO₃ solution and extraction into dichloromethane. The organic layer was evaporated to obtain the pure final compound with quantitative yield (0.016 g). Inhibitory activity of Compound 10 against individual HDAC isoform was determined as previously described. See, e.g., Bradner et al. Nat. Chem. Biol. 2010. 6:238-243.

Figure 5:
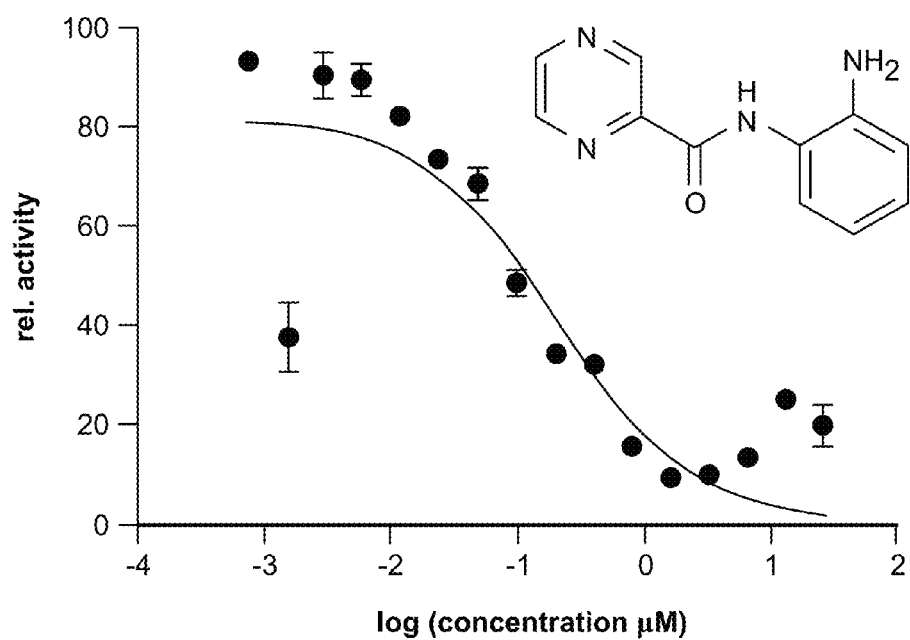
FIG. 5 is a graph showing inhibition of HDAC3 by a compound of the present invention, Compound 10, and its chemical structure.

Example 8: HDAC3 Selective Inhibitor Triggers Significant MM Cell Growth Inhibition The ortho-amino anilide Compound 10 was validated to be an HDAC class I inhibitor with specificity for HDAC3 ($IC_{50}$=289 nM) over HDAC1, 2, and 6 (FIG. 5A, FIG. 5B, and Table 3). See also, Bradner et al. Nat. Chem. Biol. 2010. 6:238-243.

TABLE 3

| $IC_{50}$ values of Compound 10 against the deacetylase activity of HDACs1-3 and 6 | | | |
|---|---|---|---|
| HDAC1 | HDAC2 | HDAC3 | HDAC6 |
| 2.0 μM | 2.2 μM | 289 μM | >20 μM |

The effect of Compound 10 on MM cell growth was assessed. Various cell lines, MM.1S (□), RPMI8226 (●), U266 (▲), OPM1 (–), and H929 (■) cells were cultured with or without Compound 10 (1.875-30 μM) for 48 h (left panel) and 72 h (right panel). Cell growth was assessed by MTT assay. All experiments were performed 3 times in quadruplicate. Data represent mean±SD. Compound 10 significantly inhibited MM cell growth in a dose-dependent fashion (FIG. 6A).

Figure 6B:
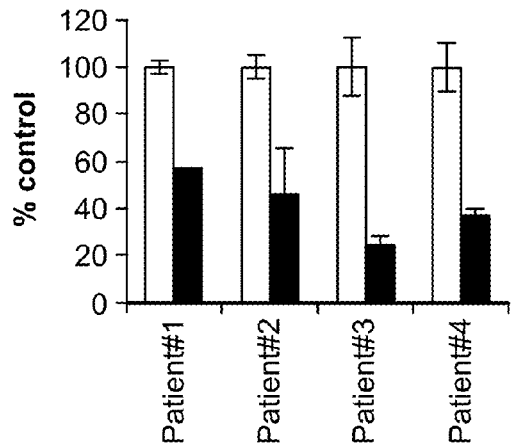
FIG. 6B is a graph depicting primary tumor cell growth when treated with (30 μM, ■) or without (□) Compound 10 for 72 hours by the MTT assay.
Figure 6C:
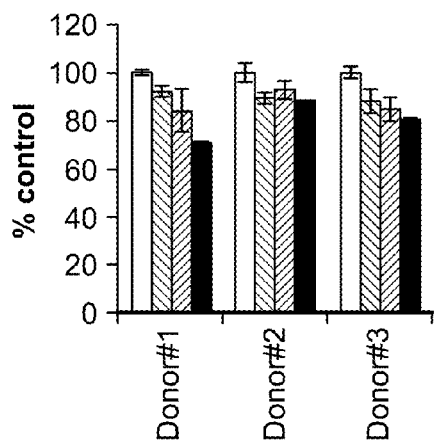
FIG. 6C is a graph depicting PBMC growth with 0 μM (□), 7.5 μM (※), 15 μM (✻) or 30 μM (■) Compound 10 for 72 hours by the MTT assay.

The effect of Compound 10 on primary tumor cells from MM patients was also assessed. Primary tumors from MM patients were treated with (30 μM, ■) or without (□) Compound 10 for 72 hours. Cell growth was then assessed by MTT assay. Data represents mean±SD from triplicates cultures (FIG. 6B). Also, PBMCs were cultured with 0 μM (□), 7.5 μM (※), 15 μM (※) or 30 μM (■) Compound 10 for 72 hours. Cell growth was assessed by MTT assay. The data represents mean±SD from triplicate cultures (FIG. 6C). Compound 10 also triggered a potent growth inhibitory effect against patient-derived MM cells (FIG. 6B), without affecting normal donor PBMCs (FIG. 6C). These results show that Compound 10 selectively targets MM cells.

Figure 6D:
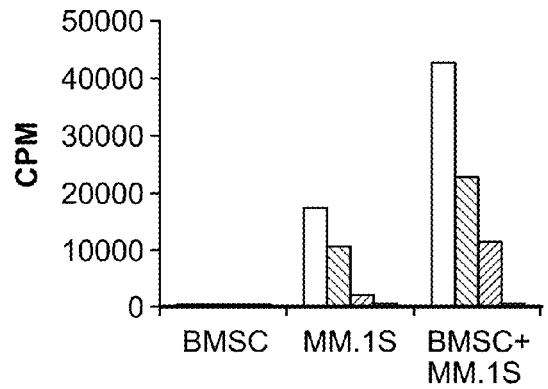
FIG. 6D is a graph depicting MM.1S cell proliferation when co-cultured with BMSCs and treated with 0 μM (□), 7.5 μM (※), 15 μM (✻) or 30 μM (■) Compound 10 for 48 hours by $^3$[H]-thymidine incorporation assay.
Figure 6E:
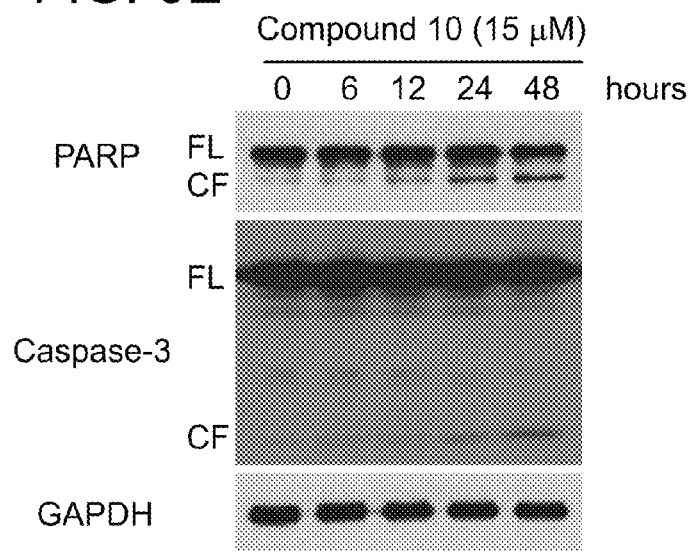
FIG. 6E is a Western blot showing PARP and caspase-3 cleavage in MM.1s cells in the presence of Compound 10.

Next, experiments were performed to determine whether Compound 10 overcomes the anti-apoptotic effect of BMSCs. See, e.g., Hideshima et al. Nat. Rev. Cancer. 2002. 2:927-937. MM.1S cells co-cultured with BMSCs were treated with 0 μM (□), 7.5 μM (※), 15 μM (※) or 30 μM (■) Compound 10 for 48 hours. Cell proliferation was measured by 3[H]-thymidine incorporation assay. Data represent mean±SD from quadruplicate cultures (FIG. 6D). Also, MM.1S cells were cultured with or without Compound 10 (15 μM) for the indicated time periods. Whole cell lysates were subjected to immunoblotting with anti-Caspase-3, -PARP and -GAPDH Abs. FL and CF indicate full-length and cleaved forms, respectively (FIG. 6E). Compound 10 in a dose-dependent fashion markedly inhibited MM cell growth even in the presence of BMSCs (FIG. 6D), and associated with caspase-3/PARP cleavage (FIG. 6E). These results show that Compound 10 induces caspase-dependent apoptosis in MM cells.

Figure 6F:
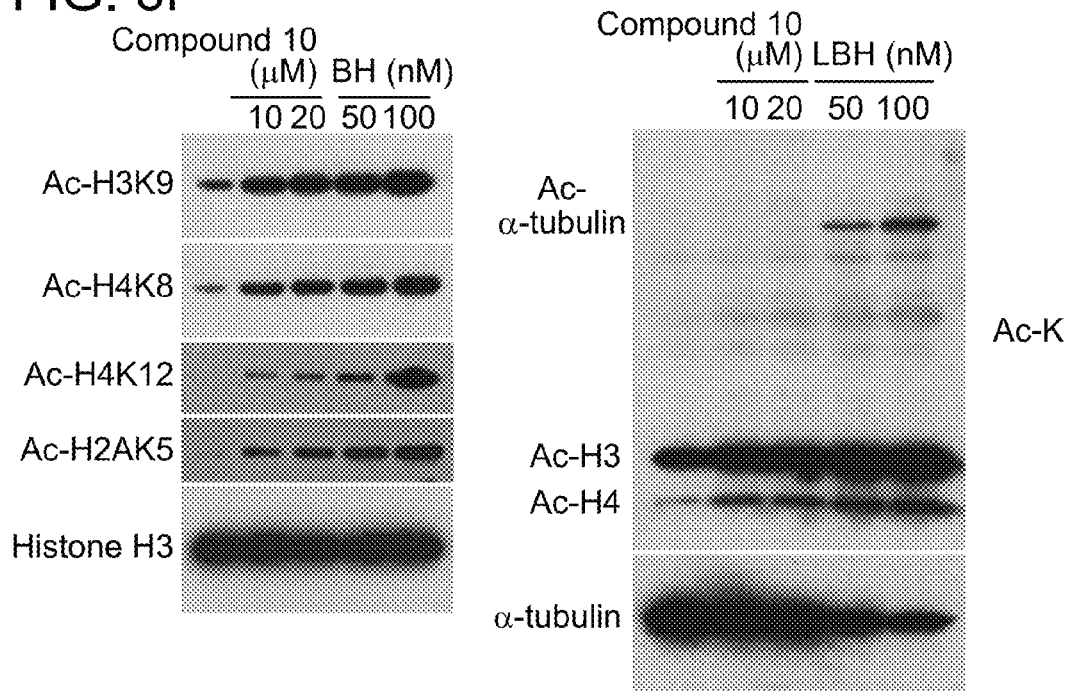
FIG. 6F is a set of Western blots depicting histone acetylation and tubulin acetylation in cells treated with Compound 10 or LBH for 12 hours.

In addition, the mechanism of the HDAC inhibitory effect by Compound 10 was determined by profiling its effect on historic acetylation in MM cells. MM.1S cells were cultured with Compound 10 (10 and 20 µM) or LBH589 (50 and 100 nM) for 12 h. Whole cell lysates were then subjected to immunoblotting with anti-Ac-H3K9, -Ac-H4K8, -Ac-H4K12, -Ac-H2AK5, -and Ac-H3 Abs (FIG. 6F, left panel), as well as Ac-lysine and Ac-α-tubulin Abs (FIG. 6F, right panel). Compound 10 in a dose-dependent fashion significantly induced acetylation of histone H2A, H3, and H4 in MM.1S cells (FIG. 6F, left panel). In contrast, Compound 10 treatment, did not increase α-tubulin acetylation, a biomarker of HDAC6 inhibition (FIG. 6F, right panel), further indicating its specificity against HDAC3. In contrast, the non-selective HDAC inhibitor LBH589 significantly triggered both histone and α-tubulin acetylation.

Figure 6G:
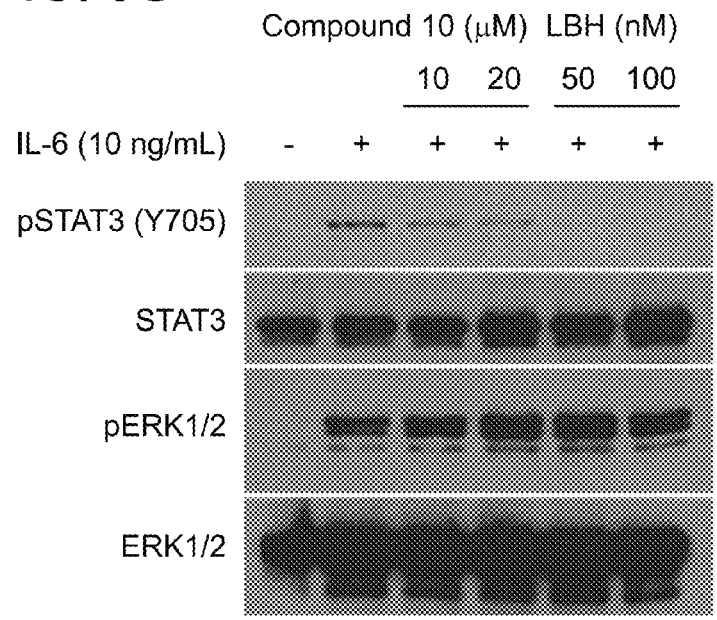
FIG. 6G is a Western blot showing STAT and ERK phosphorylation in cells treated with Compound 10 or LBH for 10 hours and then stimulated with IL-6 (10 ng/mL) for 4 hours.

Then, experiments were conducted to determine the impact of Compound 10 on STAT3 phosphorylation in MM.1S cells. MM.1S cells were cultured with or without Compound 10 (10 and 20 µM) or LBH589 (50 and 100 nM) for 10 hours and then stimulated with IL-6 (10 ng/mL) for 4 hours. Whole cell lysates were subjected to immunoblotting with anti-pSTAT3 (Tyr705), -STAT3, -pERK1/2 (Thr202/204), and -ERK1/2 Abs (FIG. 6G). Compound 10 in a dose-dependent fashion markedly downregulated p-STAT3, without affecting p-ERK1/2 (FIG. 6G).

Figure 6H:
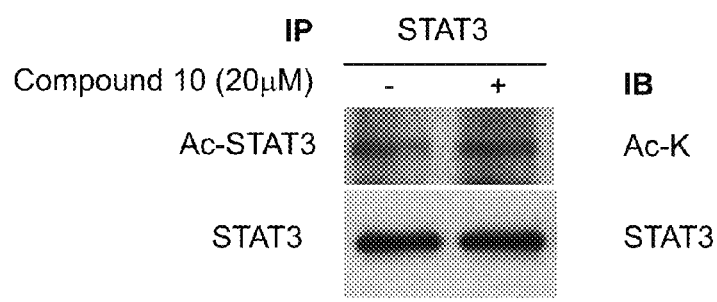
FIG. 6H is a Western blot showing STAT3 acetylation in the presence of Compound 10 for 18 hours.

In addition, MM.1S cells were treated with or without Compound 10 (20 µM) for 18 hours. Whole cell lysates were immunoprecipitated with anti-STAT3 Ab. Immunoprecipitates were then subjected to SDS-PAGE and immunoblotted with anti-Ac-K and -STAT3 Abs. As shown in FIG. 6H, Compound 10 also increased acetylation of STAT3 in MM.1S cells. Taken together, these results demonstrate that the selective HDAC3 inhibitor Compound 10-induced MM cell toxicity is associated with hyperacetylation of histones and STAT3, as well as downregulation of p-STAT3.

Example 9: HDAC3 Inhibition Synergistically Enhances Bortezomib-Induced Cytotoxicity Non-selective HDAC inhibitors show only modest anti-MM activities as single agents, which can be markedly enhanced in combination with bortezomib. See, e.g., Hideshima et al. Proc Natl Acad Sci USA 2005. 102:8567-8572; and Santo et al. Blood. 2012. 119:2579-2589. Selective HDAC6 inhibitors tubacin and ACY1215 synergistically augment bortezomib-induced cytotoxicity due to dual blockade of proteasomal and aggresomal protein degradation, evidenced by accumulation of ubiquitinated proteins. See, e.g., Hideshima et al, Proc Natl Acad Sci USA 2005, 102:8567-8572; and Santo et al. Blood, 2012. 119:2579-2589. However, the mechanism underlying the synergistic effect of bortezomib combined with class-I HDAC inhibitors was not clearly defined before the present invention.

Figure 7A:
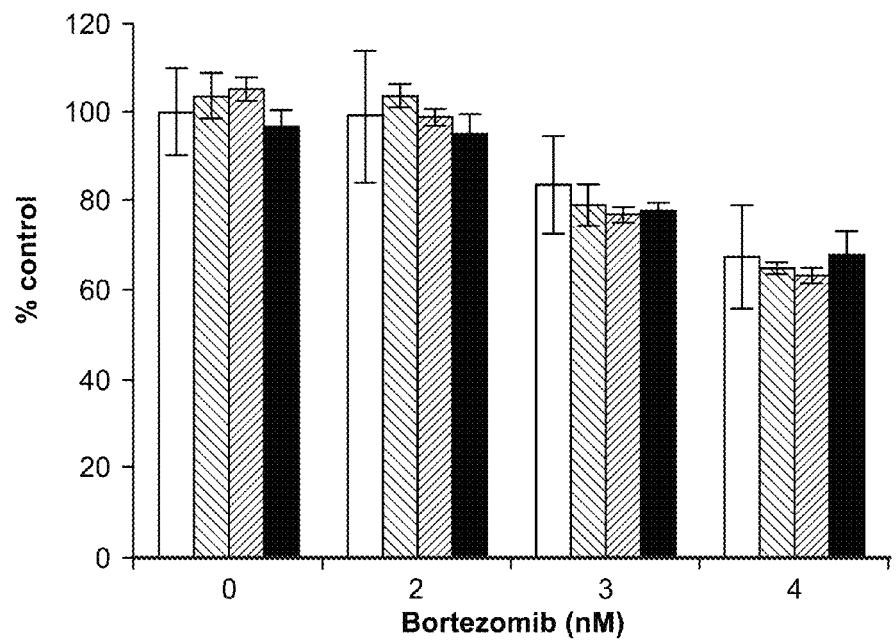
FIG. 7A is a set of graphs showing cell growth in the presence of 0 μM (□), 1 μM (□), 2 μM (※) or 3 μM (■) Merck60 or MS275 in combination with bortezomib for 24 hours.
Figure 7A:
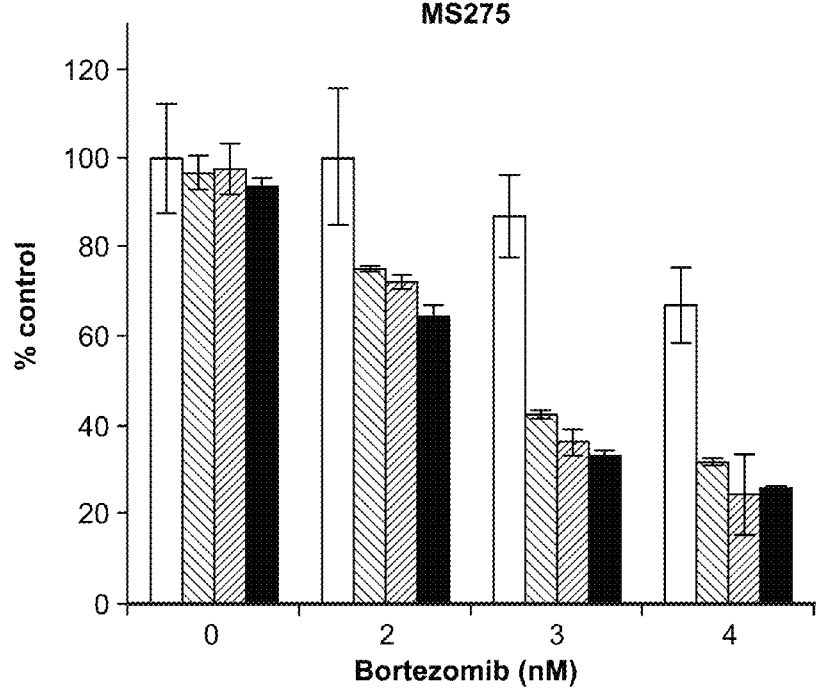

Thus, combination treatment of RPMI8226 cells with bortezomib and either Merck60 or MS275 was tested. RPMI8226 cells were treated with bortezomib (0-4 nM) in combination with 0 µM (□), 1 µM (□), 2 µM (※) or 3 µM (■) Merck60 (left panel) or MS275 (right panel) for 24 hours. There was synergistic cytotoxicity triggered by bortezomib in combination with MS275, but not with Merck60 (FIG. 7A and Table 4).

Figure 7B:
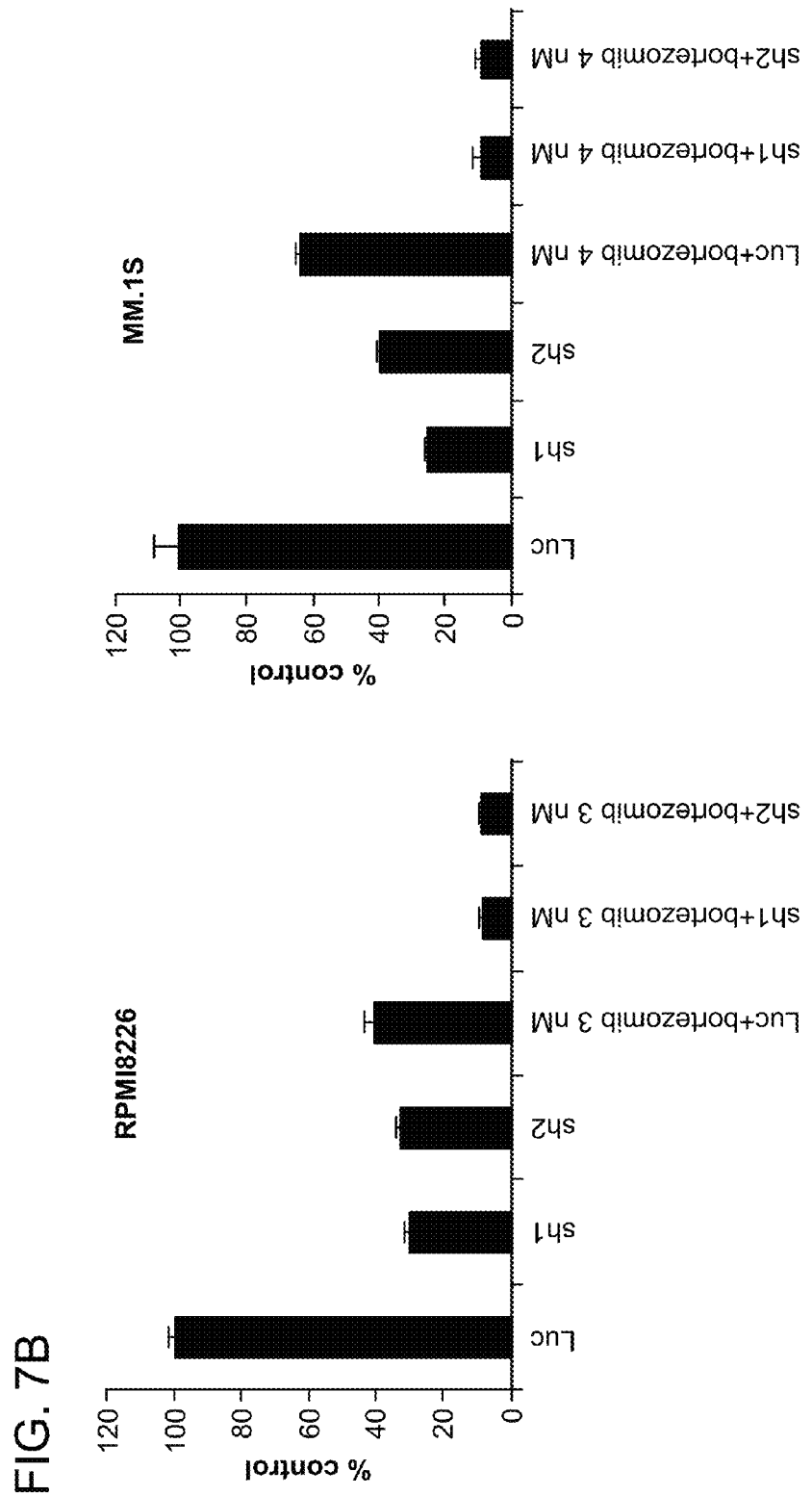
FIG. 7B is a set of graphs showing the effect of bortezomib on HDAC3 knockdown cell growth.

In addition, the effect of bortezomib on HDAC3 knockdown cells was examined. RPMI8226 (FIG. 7B, left panel) and MM.1S (FIG. 7B, right panel) cells were infected with Luc or HDAC3 (#1 and #2) shRNAs. Cells were then cultured with or without bortezomib (3 nM) for 48 hours and cell growth was assessed by MTT assay. Data represent mean±SD from triplicate cultures. As shown in FIG. 7B, bortezomib significantly enhances cytotoxicity in HDAC3 knockdown cells, indicating that HDAC3 has a key role in mediating the synergistic anti-MM activity induced by class-I HDAC inhibitors with bortezomib.

Figure 7C:
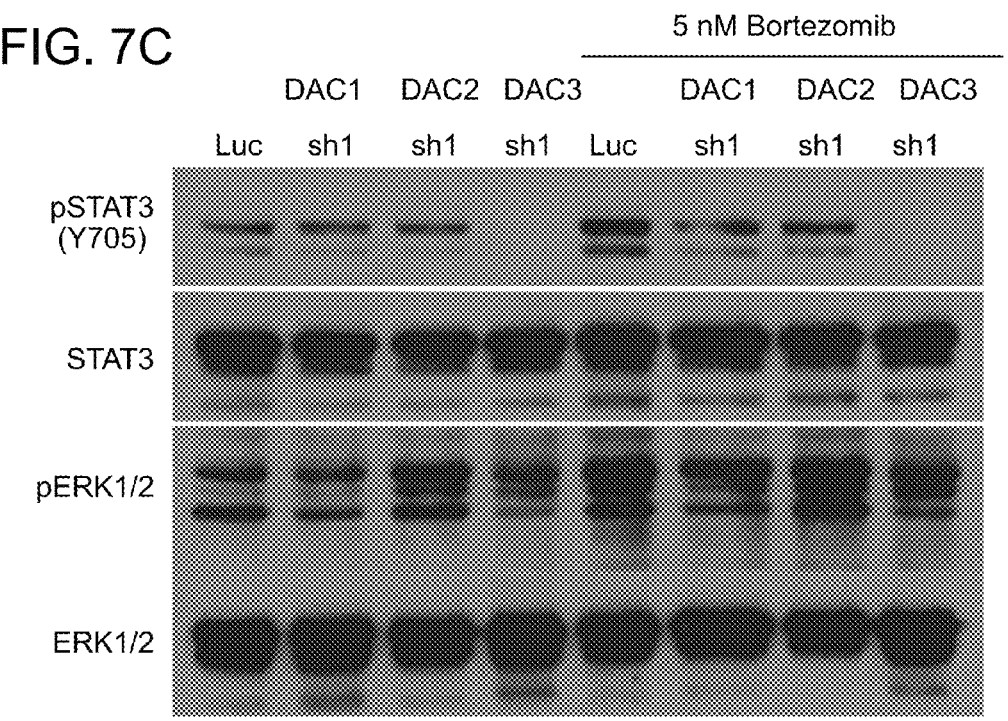
FIG. 7C is a Western blot showing the effect of bortezomib on p-STAT3 in cells treated wife shRNAs.

Bortezomib upregulates Akt activity, which can be inhibited by Akt inhibitor perifosine, and that combined therapy with bortezomib and perifosine tiggers synergistic cytotoxicity in MM cells. See, e.g., Hideshima et al. Blood. 2006, 107:4053-4062. Since bortezomib upregulates activated STAT3 in head and neck squamous cell carcinoma (see, e.g., Li et al. Mol Cancer Ther 2009. 8:2211-2220), experiments were conducted to test whether bortezomib enhances p-STAT3 in MM cells. RPMI8226 cells were infected with Luc, HDAC1 (sh1), HDAC2 (sh1) or HDAC3 (sh1) shRNAs and then treated with or without bortezomib (5 nM) for 6 hours. Whole cell lysates were subjected to immunoblotting with anti-STAT3, -pSTAT3 (Tyr705), -pERK1/2 (Thr202/204) and -ERK1/2 Abs. As shown in FIG. 7C, bortezomib upregulated p-STAT3, which is completely abrogated in HDAC3, but not in HDAC1 or HDAC2, knockdown cells. These results show that the synergistic cytotoxicity induced by combined HDAC3 knockdown with bortezomib is mediated, at least in part, by inhibition of STAT3 activity.

Figure 7D:
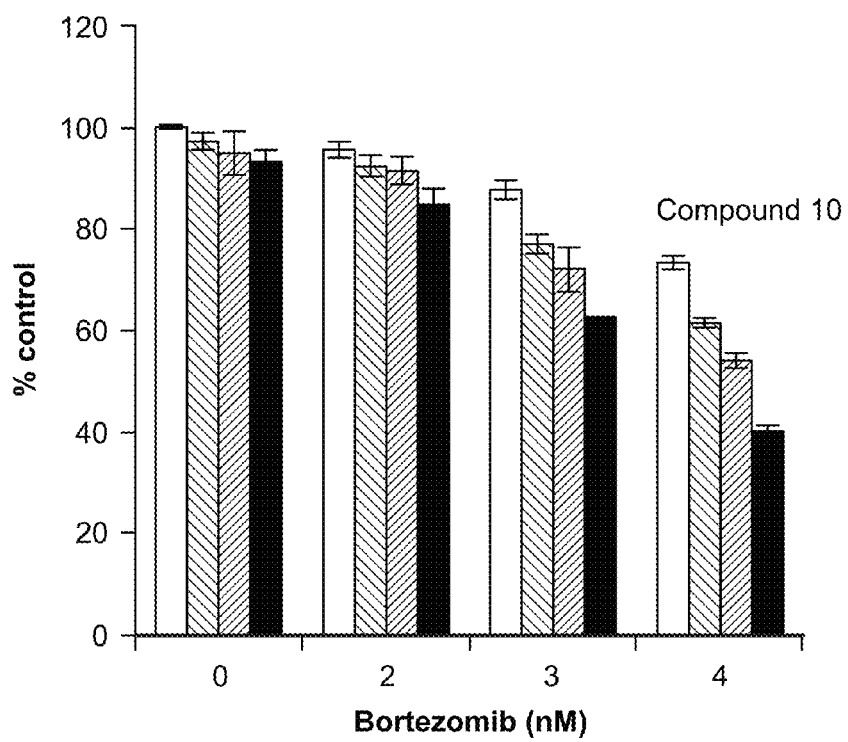
FIG. 7D is a graph depicting cell growth in the presence of 0 μM (□), 5 μM (※), 10 μM (✻) or 20 μM (■) Compound 10 and bortezomib for 24 h.
Figure 8A:
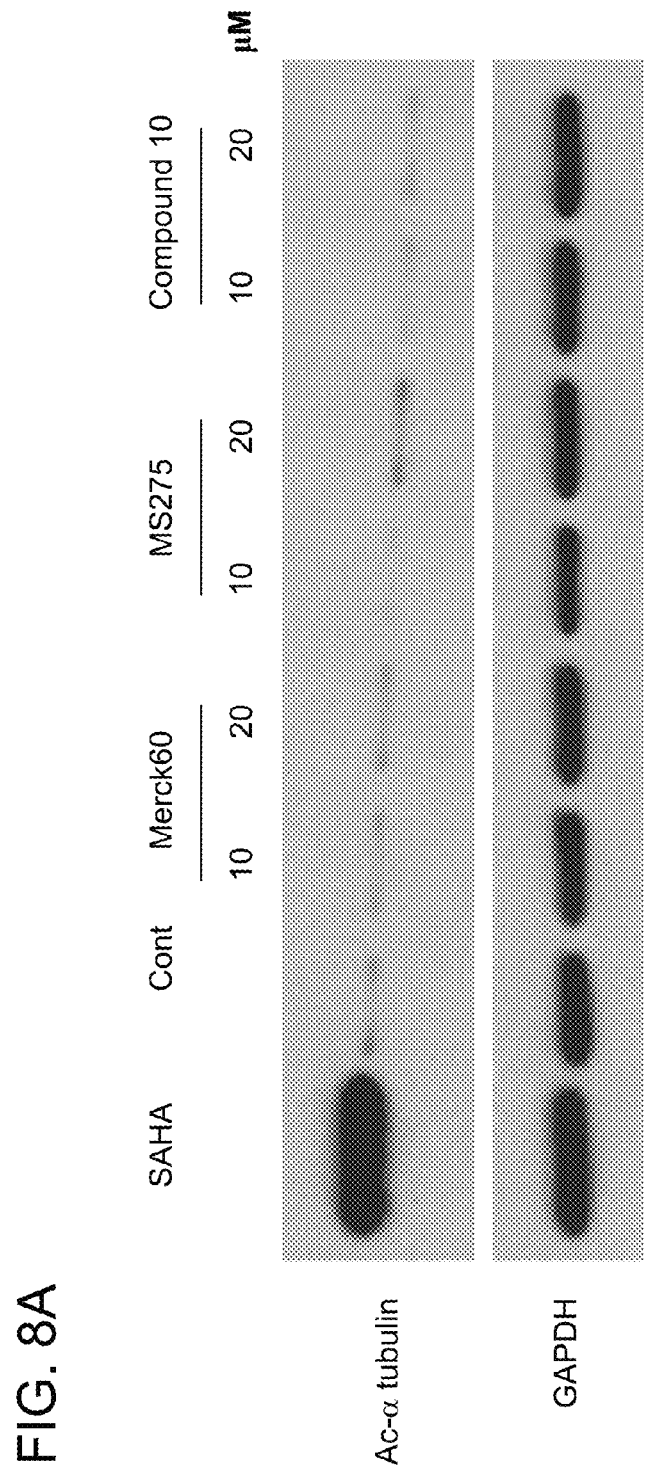
FIG. 8A is a Western blots showing the presence of acetylated-alpha-tubulin in the presence of various agents.

Also, the combination effect of bortezomib with selective HDAC3 inhibitor Compound 10 was assessed. RPMI8226 cells were treated with bortezomib (2-4 nM) in the presence of 0 µM (□), 5 µM (※), 10 µM (※) or 20 µM (■) Compound 10 for 24 h, and cell growth was then assessed by MTT assay. All experiments were performed 3 times in quadruplicate. Data represent mean±SD (FIG. 7D). Also, the level of inhibition of HDAC6, as determined by Western blot to for acetylated alpha-tubulin, by Compound 10 was determined and compared with that of suberoylanilide hydroxamic acid (SAHA), Merck60, and MS275. GAPDH was used as a loading control. Each inhibitor was added to cells at 10 or 20 um (FIG. 8A). Compound 10 did not inhibit HDAC6 evidenced by hyperacetylation of α-tubulin (FIG. 8A). Consistent with HDAC3 knockdown data, Compound 10 in a dose-dependent fashion also synergistically enhanced bortezomib-induced cytotoxicity (FIG. 7D, Table 4C).

Figure 8B:
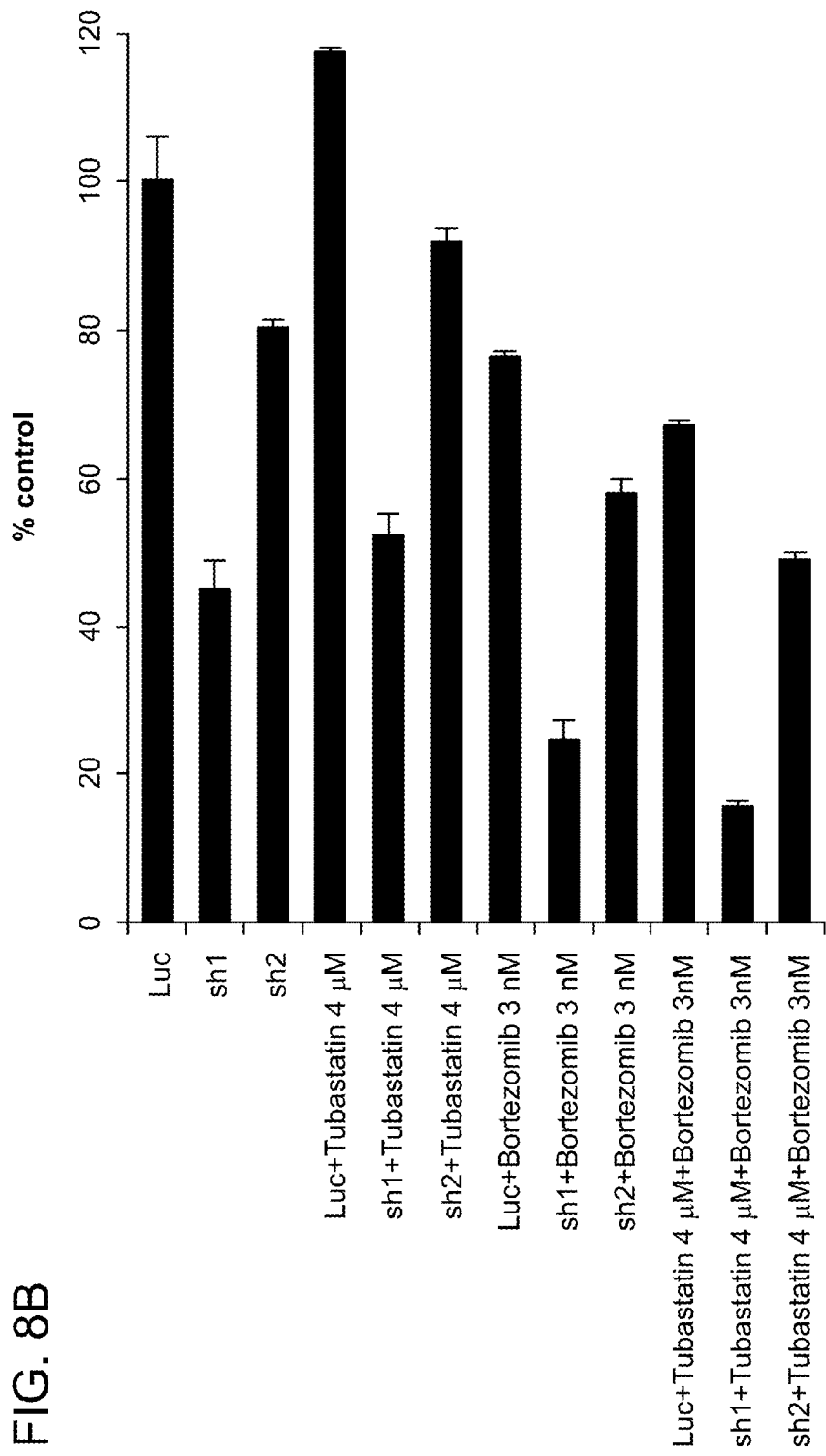
FIG. 8B is a graph depicting cell growth in the presence of various combinations of HDAC3 knockdown, tubastatin-A, and botezomib.

Also, experiments were conducted to determine whether dual inhibition of both HDAC3 and HDAC6 was more cytotoxic than either HDAC3 or HDAC6 when combined with bortezomib. Cell growth was assayed by MTT assay in the presence of Luc (control), sh1 or sh2 shRNAs against HDAC3 alone, or in combination with a selective HDAC6 inhibitor—tubastatin-A, or in combination with both tubastatin-A and bortezomib. As shown in FIG. 8B, the selective HDAC6 inhibitor tubastatin-A further enhanced cytotoxicity induced by combined HDAC3 knockdown with bortezomib.

TABLE 4

MS275 and Compound 10 with bortezomib triggers synergistic cytotoxicity in RPMI8226 cells

A

| Merck60 (µM) | Bortezomib (nM) | CI |
|---|---|---|
| 1 | 2 | 1.95 |
| 1 | 3 | 1.06 |
| 1 | 4 | 1.19 |

TABLE 4-continued

MS275 and Compound 10 with bortezomib triggers
synergistic cytotoxicity in RPMI8226 cells

| 2 | 2 | 1.54 |
| 2 | 3 | 1.21 |
| 2 | 4 | 1.34 |
| 3 | 2 | 1.45 |
| 3 | 3 | 1.4 |
| 3 | 4 | 1.55 |

B

| MS275 (μM) | Bortezomib (nM) | CI |
|---|---|---|
| 1 | 3 | 0.57 |
| 1 | 3 | 0.66 |
| 1 | 4 | 0.81 |
| 2 | 2 | 0.56 |
| 2 | 3 | 0.63 |
| 2 | 4 | 0.76 |
| 3 | 2 | 0.53 |
| 3 | 3 | 0.62 |
| 3 | 4 | 0.77 |

C

| BG45 (μM) | Bortezomib (nm) | CI |
|---|---|---|
| 5 | 2 | 1.04 |
| 5 | 3 | 0.83 |
| 5 | 4 | 0.84 |
| 10 | 2 | 1.19 |
| 10 | 3 | 0.78 |
| 10 | 4 | 0.77 |
| 20 | 2 | 0.91 |
| 20 | 3 | 0.67 |
| 20 | 4 | 0.63 |

RPMI8226 cells were treated with Merck60 or MS275 or BG45 and/or bortezomib.
Cytotoxicity was assessed by MTT assay (mean ± SD; n = 3).
Combination index (CI) was calculated using CompuSyn software.
CI < 1 indicates synergistic effects.

Figure 9A:
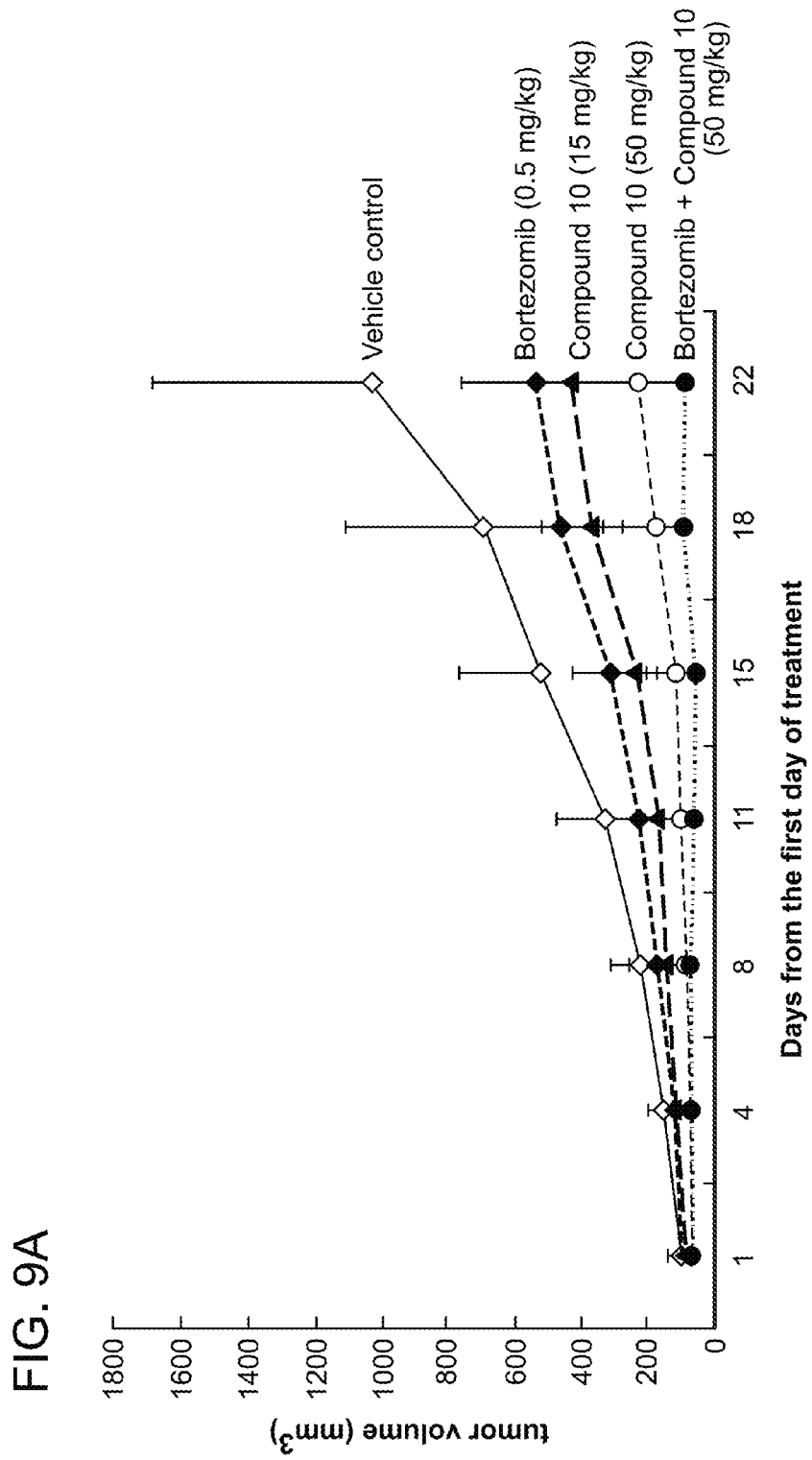
FIG. 9A is a graph depicting tumor volume in mice treated with Compound 10 and/or bortezomib.

Example 10: Compound 10 Demonstrates Significant Anti-MM Activities in a Murine Xenograft Model To evaluate the in vivo impact of Compound 10 alone or in combination with bortezomib, the subcutaneous MM.1S xenograft model of human MM in mice was used. These SCID mice were subcutaneously injected with $5 \times 10^6$ MM.1S cells. After development of measurable tumors, cohorts were treated for 3 weeks with vehicle control, 15 mg/kg Compound 10, 50 mg/kg Compound 10, 0.5 mg bortezomib, or 50 mg/kg Compound 10 with bortezomib for 3 weeks. Tumor volume was calculated from caliper measurements twice weekly, and data represent mean±SD (FIG. 9A). Compound 10 significantly inhibited MM tumor growth in the treatment versus control group in a dose-dependent fashion. Significant differences were observed in control versus Compound 10 15 mg/kg, control versus Compound 10 50 mg/kg, and Compound 10 15 mg/kg versus Compound 10 50 mg/kg at day 22 (p<0.05, FIG. 9A). Moreover, Compound 10 50 mg/kg in combination with bortezomib further enhanced either single agent activity (p<0.05).

Figure 9B:
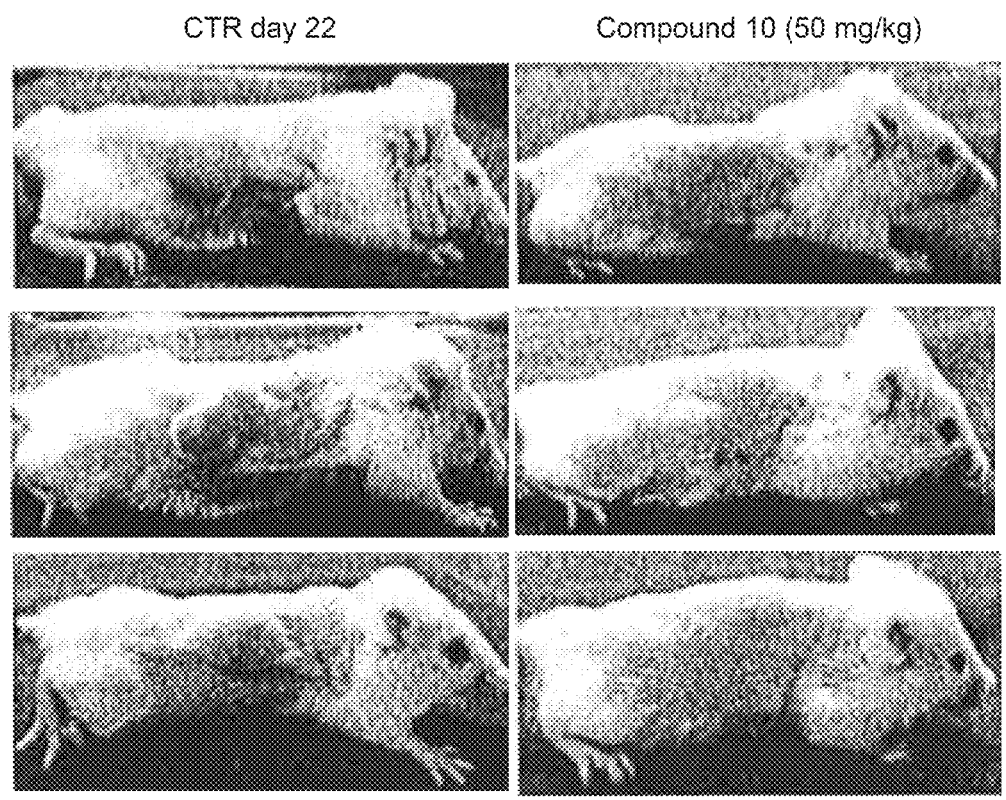
FIG. 9B are representative whole-body images showing tumors in mice after 3-week treatment.

In addition, representative whole-body images from vehicle control (FIG. 9B, left panel) and Compound 10 (50 mg/kg; FIG. 9B, right panel) groups were taken after the 3-week treatment. These results confirm that Compound 10 triggers in vivo anti-MM activities.

Figure 10:
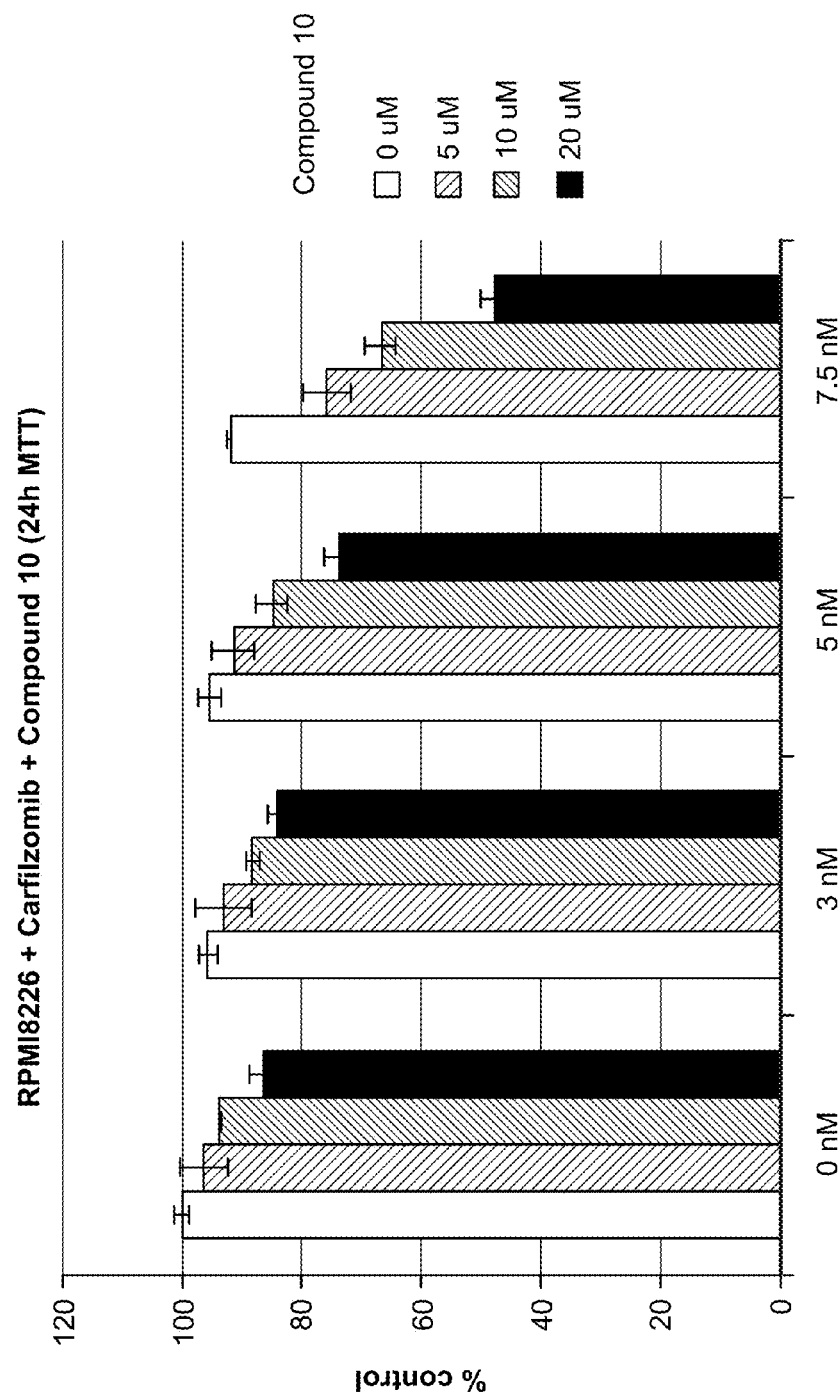
FIG. 10 is a graph showing the effect of Compound 10 on cytotoxicity induced by carfilzomib.

Example 11: Effect of Combined Compound 10 and Carfilzomib Treatment on MM Cell Cytotoxicity Experiments were conducted to determine whether Compound 10 enhances cytotoxicity induced by carfilzomib (a proteasome inhibitor). RPMI8226 cells were cultured with increased concentrations of Compound 10 (5, 10 and 20 um) in the presence of 0 nM (□), 3 nM (※), 5 nM (⁂), or 7.5 nM (■) carfilzomib for 24 h, and cell growth was then assessed by MTT assay (FIG. 10). All experiments were performed 3 times in quadruplicate. Data represent mean+/−SD (FIG. 10). The y-axis (% control) indicates the relative number of viable cells after each treatment. As shown in FIG. 10, Compound 10 enhanced the cytotoxicity of carfilzomib.

EQUIVALENTS

Those skilled in the art will recognize, or be able to ascertain using no more than routine experimentation, many equivalents to the specific embodiments and methods described herein. Such equivalents are intended to be encompassed by the scope of the present invention.

All patents, patent applications, and literature references cited herein are hereby expressly incorporated by reference.

The invention claimed is:

1. A compound of formula Ia1, Ia2, Ia3, Ia4, Ia5, Ia6, Ib, or Ic:

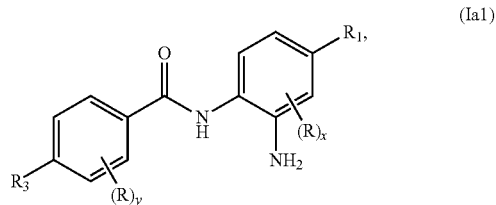

(Ia1)

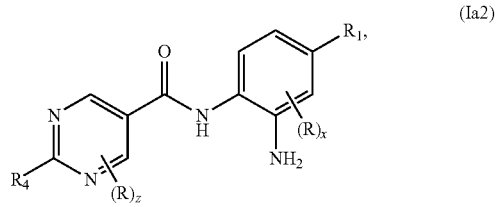

(Ia2)

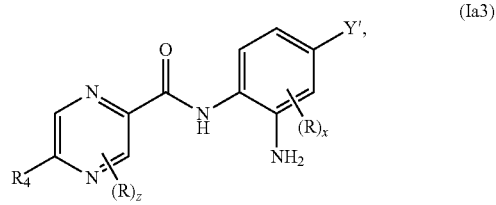

(Ia3)

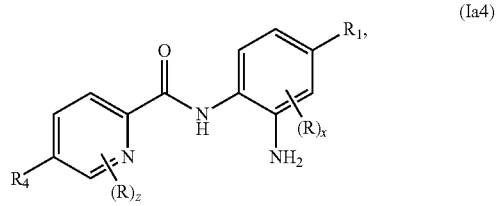

(Ia4)

-continued

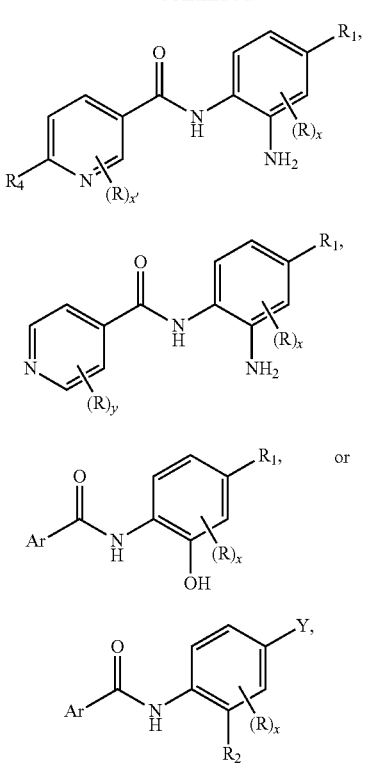

wherein:
Ar is unsubstituted or substituted phenyl, unsubstituted or substituted pyrazinyl, unsubstituted or substituted pyrimidinyl, unsubstituted or substituted pyridinyl, unsubstituted or substituted quinolinyl, unsubstituted or substituted isoquinolinyl, unsubstituted or substituted quinazolinyl, or unsubstituted or substituted quinoxalinyl;
$R_1$ and $R_2$ are each independently H, hydroxyl, cyano, halogen, unsubstituted or substituted amino, unsubstituted or substituted $C_1$-$C_6$ alkyl, or unsubstituted or substituted $C_1$-$C_6$ alkoxy;
each R is independently hydroxyl, cyano, halogen, unsubstituted or substituted amino, unsubstituted or substituted $C_1$-$C_6$ alkyl, unsubstituted or substituted $C_1$-$C_6$ alkoxy, or unsubstituted or substituted $C_6$-$C_{10}$ aryl;
Y' is hydroxyl, cyano, halogen, unsubstituted or substituted amino, unsubstituted or substituted $C_1$-$C_6$ alkyl, or unsubstituted or substituted $C_1$-$C_6$ alkoxy;
Y is halogen;
x is 0, 1, 2, or 3;
x' is 0, 1, 2, or 3;
y is 0, 1, 2, 3, or 4;
z is 0, 1, or 2:
$R_3$ is H, unsubstituted $C_1$-$C_6$ alkyl, halogen, or $NT_{n1}T_{n2}$;
$T_{n1}$ and $T_{n2}$ are each independently H, unsubstituted $C_1$-$C_6$ alkyl, or $C(O)X_1$;
$R_4$ is H, unsubstituted or substituted $C_1$-$C_6$ alkyl, halogen, or $NT_{n3}T_{n4}$;
$T_{n3}$ and $T_{n4}$ are each independently H, unsubstituted or substituted $C_1$-$C_6$ alkyl, unsubstituted or substituted $C_6$-$C_{10}$ aryl, or $C(O)X_1$; and
$X_1$ is unsubstituted or substituted $C_1$-$C_6$ alkyl,
provided that when Ar is unsubstituted pyrazinyl, x is not 0,
provided that when $R_4$ is H and x' is 0, x is not 0, and
provided the compound is not 4-(acetylamino)-N-(2-aminophenyl)benzamide or pyridin-3-ylmethyl N-[[4-[(2-aminophenyl)carbamoyl]phenyl]methyl]carbamate,
or a pharmaceutically acceptable salt or ester thereof.

2. The compound of claim 1, wherein
the compound is a compound of formula Ia1, and $R_3$ is unsubstituted $C_1$-$C_6$ alkyl, halogen, or $NT_{n1}T_{n2}$; or
the compound is a compound of formula Ib or Ic, and Ar is substituted phenyl.

3. The compound of claim 1, wherein
the compound is a compound of formula Ia4, Ia5, or Ia6; or
the compound is a compound of formula Ib or Ic, and Ar is unsubstituted or substituted pyridin-2-yl, pyridin-3-yl, or pyridin-4-yl.

4. The compound of claim 1, wherein
the compound is a compound of formula Ia2; or
the compound is a compound of formula Ib or Ic, and Ar is unsubstituted or substituted pyrimidin-5-yl.

5. The compound of claim 1, wherein
the compound is a compound of formula Ia3; or
the compound is a compound of formula Ib or Ic, and Ar is unsubstituted or substituted pyrazinyl.

6. The compound of claim 1, wherein
the compound is a compound of formula Ia1, Ia2, Ia4, Ia5, Ia6, or Ib, and $R_1$ is H; or
the compound is a compound of formula Ic, and $R_2$ is hydroxyl or unsubstituted or substituted amino.

7. The compound of claim 1, wherein
the compound is a compound of formula Ia1, Ia2, Ia4, Ia5, Ia6, or Ib, and $R_1$ is halogen; or
the compound is a compound of formula Ic, and $R_2$ is hydroxyl or unsubstituted or substituted amino.

8. The compound of claim 1, wherein
the compound is a compound of formula Ic, $R_2$ is H; or
the compound is a compound of formula Ia1, Ia2, Ia4, Ia5, Ia6, or Ib, and $R_1$ is halogen.

9. The compound of claim 1, wherein x is 1, 2, or 3.

10. The compound of claim 1, wherein:
the compound is a compound of formula Ib or Ic; and
Ar is unsubstituted or substituted phenyl, unsubstituted or substituted pyrazinyl, unsubstituted or substituted pyrimidinyl, or unsubstituted or substituted pyridinyl.

11. A pharmaceutical composition comprising a compound of claim 1 or a pharmaceutically acceptable salt or ester thereof, and a pharmaceutically acceptable carrier.

12. A method of treating a hematological cell proliferative disorder in a subject, comprising administering to the subject an effective amount of a compound of claim 1 or a pharmaceutically acceptable salt or ester thereof, and a pharmaceutically acceptable carrier.

13. The method of claim 12, wherein the hematological cell proliferative disorder is a multiple myeloma.

14. The method of claim 13, further comprising administering to the subject a second therapeutic agent.

15. The method of claim 14, wherein the second therapeutic agent is selected from the group consisting of an HDAC inhibitor, a proteasomal inhibitor, a deubiquitinase inhibitor, a demethylase inhibitor, an endoplasmic reticulum (ER) stressor, a JNK inhibitor, and a caspase inhibitor.

16. The method of claim 15, wherein the second therapeutic agent is a proteasomal inhibitor.

17. The method of claim 16, wherein the proteasomal inhibitor is bortezomib.

18. The compound of claim 1, wherein the compound is a compound of formula Ia1, Ia2, Ia3, Ia4, Ia5, Ia6, Ib, or Ic, or a pharmaceutically acceptable salt or solvate thereof.

19. A pharmaceutical composition comprising a compound of claim 1 or a pharmaceutically acceptable salt thereof, and a pharmaceutically acceptable carrier.

20. A method of treating a hematological cell proliferative disorder in a subject, comprising administering to the subject an effective amount of a compound of claim 1 or a pharmaceutically acceptable salt thereof, and a pharmaceutically acceptable carrier.

21. A compound selected from the group consisting of

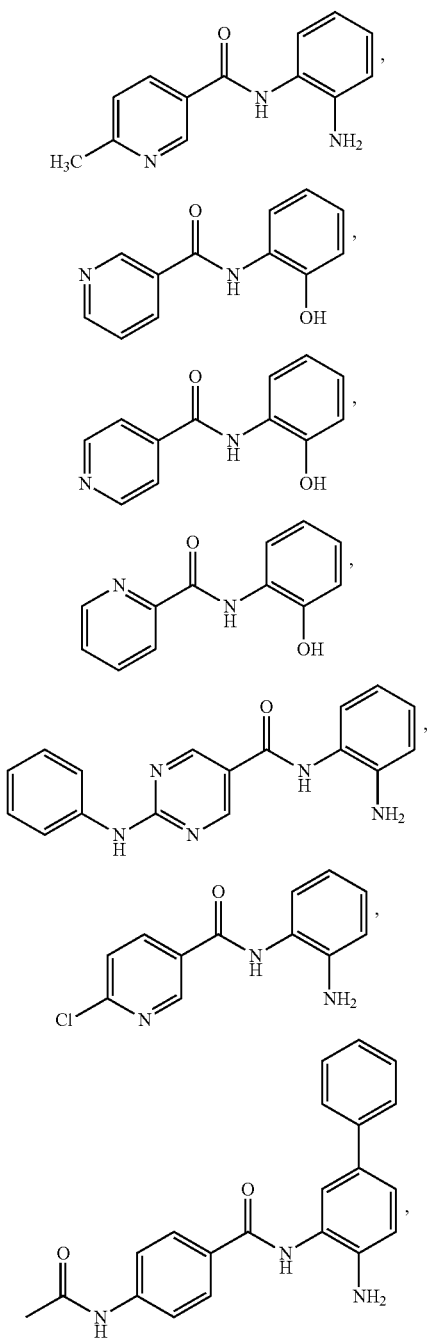

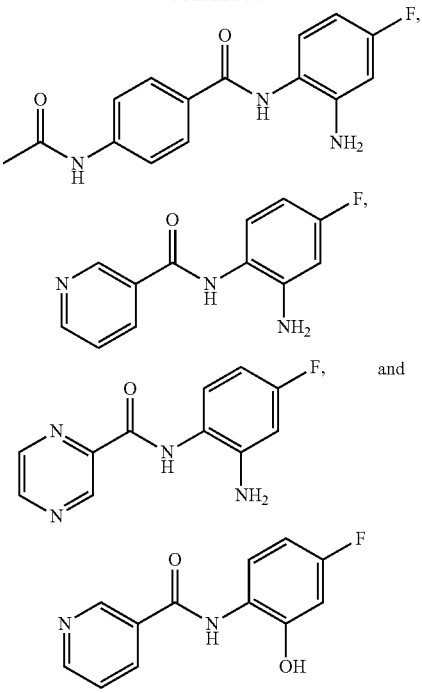

or a pharmaceutically acceptable salt or ester, solvate, or prodrug thereof.

22. The compound of claim 21, wherein the compound is selected from the group consisting of

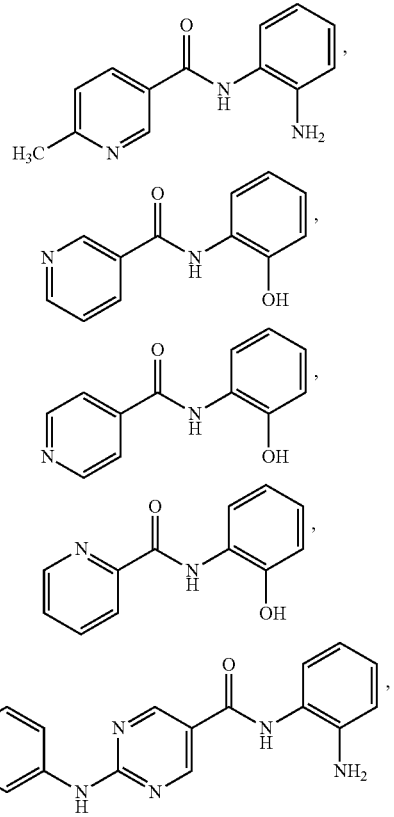

-continued
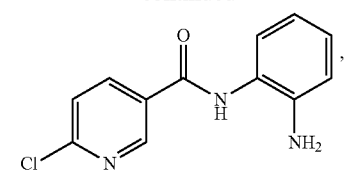
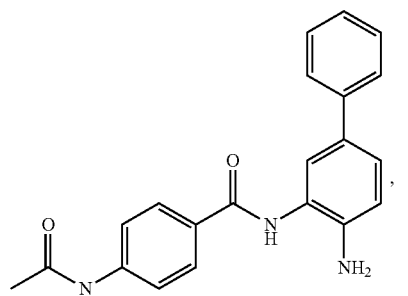
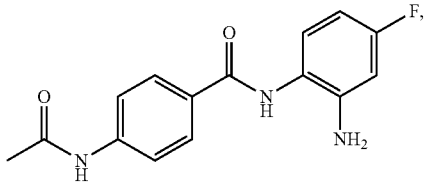
-continued
or a pharmaceutically acceptable salt thereof.
* * * * *

UNITED STATES PATENT AND TRADEMARK OFFICE
CERTIFICATE OF CORRECTION

PATENT NO. : 9,988,343 B2
APPLICATION NO. : 15/034276
DATED : June 5, 2018
INVENTOR(S) : Ralph Mazitschek et al.

Page 1 of 1

It is certified that error appears in the above-identified patent and that said Letters Patent is hereby corrected as shown below:

In the Specification

At Column 1, Lines 12-19, (approx.) under Government Support, please replace:
"This invention was made with government support under Grant Nos. SPORE-P50100707, P01 CA78378, R01 CA50947, RO1 DA02830, and P50CA086355, awarded by the National Institutes of Health. The U.S. government has certain rights in the invention. This statement is included solely to comply with 37 C.F.R. § 401.14(a)(f)(4) and should not be taken as an assertion or admission that the application discloses and/or claims only one invention."

With:
-- This invention was made with government support under grant numbers P01 CA078378, R01 CA050947, R01 DA028303, P50 CA086355, and P50 CA100707 awarded by The National Institutes of Health. The government has certain rights in the invention. --

Signed and Sealed this
Seventeenth Day of September, 2019

Andrei Iancu
*Director of the United States Patent and Trademark Office*